United States Patent
Woods et al.

(10) Patent No.: US 11,702,637 B2
(45) Date of Patent: *Jul. 18, 2023

(54) SYSTEM AND METHOD FOR EXTRACTION AND CRYOPRESERVATION OF BONE MARROW

(71) Applicant: Ossium Health, Inc., San Francisco, CA (US)

(72) Inventors: Erik John Woods, Carmel, IN (US); Brian H. Johnstone, Fishers, IN (US); Dongsheng Gu, Indianapolis, IN (US); Aubrey Marie Sherry, Carmel, IN (US); Kelsey Gwen Musall, Avon, IN (US); John R. Woods, Indianapolis, IN (US); James Hardin, Columbia, SC (US); Alan Hooks, Commerce City, CO (US)

(73) Assignee: Ossium Health, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,395

(22) Filed: Sep. 4, 2020

(65) Prior Publication Data
US 2020/0399606 A1  Dec. 24, 2020

Related U.S. Application Data

(63) Continuation of application No. 16/734,713, filed on Jan. 6, 2020.

(60) Provisional application No. 62/938,480, filed on Nov. 21, 2019, provisional application No. 62/834,087, filed on Apr. 15, 2019.

(51) Int. Cl.
*C12N 5/0775* (2010.01)
*A61B 17/16* (2006.01)
*A01N 1/02* (2006.01)
*A61B 17/00* (2006.01)

(52) U.S. Cl.
CPC ......... *C12N 5/0663* (2013.01); *A01N 1/0221* (2013.01); *A61B 17/1611* (2013.01); *A61B 2017/00831* (2013.01)

(58) Field of Classification Search
CPC .............................. C12N 5/0663; A61K 35/28
See application file for complete search history.

(56) References Cited

U.S. PATENT DOCUMENTS

| 4,674,184 A | 6/1987 | Anderson |
|---|---|---|
| 4,710,472 A | 12/1987 | Saur et al. |
| 5,474,687 A | 12/1995 | Van Vlasselaer |
| 5,672,346 A | 9/1997 | Srour et al. |
| 5,766,944 A | 6/1998 | Ruiz |
| 5,840,580 A | 11/1998 | Terstappen et al. |
| 5,858,782 A | 1/1999 | Long et al. |
| 6,739,112 B1 | 5/2004 | Marino |
| 6,900,029 B1 | 5/2005 | Coulter et al. |
| 7,470,538 B2 | 12/2008 | Laughlin et al. |
| 7,547,210 B1 | 6/2009 | Valen |
| 7,794,705 B2 | 9/2010 | Pecora et al. |
| 7,915,043 B2 | 3/2011 | Caligiuri et al. |
| 7,927,785 B2 | 4/2011 | Milhem et al. |
| 8,048,618 B2 | 11/2011 | Luk et al. |
| 8,088,370 B2 | 1/2012 | Pecora et al. |
| 8,343,485 B2 | 1/2013 | Pecora et al. |
| 8,425,899 B2 | 4/2013 | Pecora et al. |
| 8,637,005 B2 | 1/2014 | Pecora et al. |
| 8,709,403 B2 | 4/2014 | Pecora et al. |
| 8,956,862 B2 | 2/2015 | Pal et al. |
| 9,034,316 B2 | 5/2015 | Pecora et al. |
| 9,078,429 B2 | 7/2015 | McGann et al. |
| 9,192,695 B2 | 11/2015 | Shi |
| 9,241,959 B2 | 1/2016 | Tang |
| 9,402,377 B2 | 8/2016 | Flavell et al. |
| 9,409,906 B2 | 8/2016 | Sauvageau et al. |
| 9,499,792 B2 | 11/2016 | Chretien et al. |
| 9,504,717 B2 | 11/2016 | Strober et al. |
| 9,533,010 B2 | 1/2017 | Pecora et al. |
| 9,534,202 B2 | 1/2017 | Pecora et al. |
| 9,561,253 B2 | 2/2017 | Strober et al. |
| 9,675,643 B2 | 6/2017 | Weston et al. |
| 9,675,644 B2 | 6/2017 | Weston et al. |
| 9,687,511 B2 | 6/2017 | Weston et al. |
| 9,808,558 B2 | 11/2017 | Shi |
| 9,814,803 B2 | 11/2017 | Shi |
| 9,828,586 B2 | 11/2017 | Tom et al. |

(Continued)

FOREIGN PATENT DOCUMENTS

| CN | 107012119 A | 8/2017 |
|---|---|---|
| EP | 3107995 B1 | 10/2019 |

(Continued)

OTHER PUBLICATIONS

Gorantla et al.: Development and validation of a procedure to isolate viable bone marrow cells from the vertebrae of cadaveric organ donors for composite organ grafting. Cytotherapy, 2012. 14(1): p. 104-13. (Year: 2012).*

(Continued)

*Primary Examiner* — Teresa E Knight

(74) *Attorney, Agent, or Firm* — Wilson Sonsini Goodrich & Rosati

(57) ABSTRACT

Methods are provided for extracting bone marrow cells from bone obtained from deceased donors, for preparing the bone marrow for cryopreservation and for obtaining desired cells from cryopreserved and fresh bone marrow.

21 Claims, 26 Drawing Sheets

(56) References Cited

U.S. PATENT DOCUMENTS

| | | |
|---|---|---|
| 9,945,854 B2 | 4/2018 | Altman et al. |
| 9,963,678 B2 | 5/2018 | Tom et al. |
| 9,974,807 B2 | 5/2018 | Strober et al. |
| 10,047,344 B2 | 8/2018 | Poon et al. |
| 10,076,113 B2 | 9/2018 | Chretien et al. |
| 10,076,542 B2 | 9/2018 | Strober et al. |
| 10,080,769 B2 | 9/2018 | Strober et al. |
| 10,143,562 B2 | 12/2018 | Malinin |
| 10,159,694 B2 | 12/2018 | Strober et al. |
| 10,183,043 B2 | 1/2019 | Strober et al. |
| 10,258,648 B2 | 4/2019 | Strober et al. |
| 10,286,112 B2 | 5/2019 | Govil |
| 10,400,218 B2 | 9/2019 | Itescu et al. |
| 10,472,608 B2 | 11/2019 | Bader et al. |
| 10,513,690 B2 | 12/2019 | Ganey et al. |
| 10,550,369 B2 | 2/2020 | Tom et al. |
| 10,603,340 B2 | 3/2020 | Strober et al. |
| 10,645,921 B2 | 5/2020 | Temple et al. |
| 10,660,329 B2 | 5/2020 | Ivanovic et al. |
| 10,660,954 B2 | 5/2020 | Mitchell et al. |
| 10,669,528 B2 | 6/2020 | Rossi et al. |
| 2002/0039786 A1 | 4/2002 | Reid et al. |
| 2002/0182186 A1 | 12/2002 | Loeb |
| 2003/0082158 A1 | 5/2003 | Symonds et al. |
| 2004/0072347 A1 | 4/2004 | Schuler et al. |
| 2004/0258670 A1 | 12/2004 | Laughlin et al. |
| 2005/0233299 A1 | 10/2005 | Sawa et al. |
| 2007/0036734 A1 | 2/2007 | Tahara et al. |
| 2007/0224587 A1 | 9/2007 | Forsell et al. |
| 2010/0178279 A1 | 7/2010 | Cunningham-Rundles et al. |
| 2010/0260721 A1 | 10/2010 | McGonagie et al. |
| 2010/0310535 A1 | 12/2010 | Nakamura et al. |
| 2010/0310536 A1 | 12/2010 | Nakamura et al. |
| 2012/0052049 A1 | 3/2012 | Woods et al. |
| 2012/0276581 A1 | 11/2012 | Arav et al. |
| 2012/0276628 A1 | 11/2012 | Khan et al. |
| 2013/0011376 A1 | 1/2013 | Peled et al. |
| 2013/0216495 A1 | 8/2013 | Motlagh et al. |
| 2013/0236433 A1 | 9/2013 | Webster |
| 2013/0302293 A1 | 11/2013 | Webster |
| 2015/0216911 A1 | 8/2015 | Vines et al. |
| 2016/0000062 A1 | 1/2016 | Chen et al. |
| 2016/0089401 A1 | 3/2016 | Woods et al. |
| 2016/0101134 A1 | 4/2016 | Tang |
| 2017/0035935 A1 | 2/2017 | Uveges et al. |
| 2017/0151287 A1 | 6/2017 | Von Maltzahn et al. |
| 2017/0198257 A1 | 7/2017 | Bader et al. |
| 2017/0239390 A1 | 8/2017 | Ganey et al. |
| 2017/0240862 A1 | 8/2017 | Ganey et al. |
| 2017/0247659 A1 | 8/2017 | Ganey et al. |
| 2018/0169301 A1 | 6/2018 | Temple et al. |
| 2018/0221410 A1 | 8/2018 | Strober et al. |
| 2018/0243337 A1 | 8/2018 | Strober et al. |
| 2018/0282762 A1 | 10/2018 | Gori |
| 2018/0326122 A1 | 11/2018 | Ganey et al. |
| 2018/0334655 A1 | 11/2018 | Ganey et al. |
| 2018/0353541 A1 | 12/2018 | Delaney |
| 2019/0000877 A1 | 1/2019 | Strober et al. |
| 2019/0083530 A1 | 3/2019 | Strober et al. |
| 2019/0091262 A1 | 3/2019 | Strober et al. |
| 2019/0151506 A1 | 5/2019 | Ganey et al. |
| 2019/0191694 A1 | 6/2019 | Temple et al. |
| 2019/0192561 A1 | 6/2019 | Strober et al. |
| 2019/0192562 A1 | 6/2019 | Strober et al. |
| 2019/0298762 A1 | 10/2019 | Strober et al. |
| 2019/0336528 A1 | 11/2019 | Strober et al. |
| 2019/0343112 A1 | 11/2019 | Woods et al. |
| 2019/0345450 A1 | 11/2019 | Radtke et al. |
| 2019/0358257 A1 | 11/2019 | Strober et al. |
| 2020/0016198 A1 | 1/2020 | Jongen et al. |
| 2020/0254015 A1 | 8/2020 | Strober et al. |
| 2020/0325451 A1 | 10/2020 | Woods et al. |
| 2020/0337648 A1 | 10/2020 | Saripalli et al. |
| 2020/0399608 A1 | 12/2020 | Woods et al. |
| 2021/0214688 A1 | 7/2021 | Johnstone et al. |
| 2022/0241342 A1 | 8/2022 | Woods et al. |

FOREIGN PATENT DOCUMENTS

| | | |
|---|---|---|
| WO | WO-9307824 A1 | 4/1993 |
| WO | WO-03024215 A1 | 3/2003 |
| WO | WO-2011069117 A1 | 6/2011 |
| WO | WO-2011151452 A1 | 12/2011 |
| WO | WO-2016210292 A1 | 12/2016 |
| WO | WO-2017127755 A1 | 7/2017 |
| WO | WO-2017216775 A3 | 2/2018 |
| WO | WO-2017218948 A3 | 2/2018 |
| WO | WO-2018022651 A1 | 2/2018 |
| WO | WO-2019006328 A1 | 1/2019 |
| WO | WO-2020047236 A1 | 3/2020 |
| WO | WO-2020058324 A1 | 3/2020 |
| WO | WO-2020061180 A1 | 3/2020 |
| WO | WO-2020214400 A1 | 10/2020 |
| WO | WO-2022020210 A1 | 1/2022 |
| WO | WO-2022081909 A1 | 4/2022 |

OTHER PUBLICATIONS

Rybka et al.: Hematopoietic progenitor cell content of vertebral body marrow used for combined solid organ and bone marrow transplantation. Transplantation, 1995. 59(6): p. 871-4. (Year: 1995).*

Michalova et al. Hematopoietic Stem Cells Survive Circulation Arrest and Reconstitute Hematopoiesis in Myeloablated Mice, 2011, Biology of Blood and Bone Marrow Transplantation 17(9): 1273-1281 (Year: 2011).*

Soderdahl et al. Cadaveric bone marrow and spleen cells for transplantation, 1998 Bone Marrow Transplantation 21: 79-84 (Year: 1998).*

Urso et al. "Short-term Preservation of Mouse Bone Marrow at Refrigeration and Room Temperature for Irradiation Experiments" (1957), J App Physiol, vol. 10(2): 314-316. (Year: 1957).*

Saegeman et al. "Influence of postmordem time on the outcome of blood cultures among cadaveric tissue donors" (2009) Eur J Microbiol Infect Dis, vol. 28: 161-168. (Year: 2009).*

Brubaker et al. "Tissue recovery practices and biouburden: a systemic review" (2016) Cell Tissue Bank, vol. 17, 561-571. (Year: 2016).*

Delloyd's Lab Tech. Standard sieves and Mesh sizes. Online publication. http://delloyd.50megs.com/moreinfo/mesh.html. pp. 2-3 (2018).

Du et al.: Rational Design of a Fluorescent Hydrogen Peroxide Probe Based on the Umbelliferone Fluorophore. Tetrahedron Letters. 49(19):3045-3048 (2008) DOI:10.1016/j.tetlet.2008.03.063.

Eagle et al.: Assessment of an improved bone washing protocol for deceased donor human bone. Cell Tissue Bank. 16:83-90 (2014) DOI:10.1007/s10561-014-9443-z.

Fresenius Kabi AG. 510(k) Summary. Bone Marrow Collection Stand. (2017) https://www.fda.gov/media/106490/download.

Hemacare Corporation. Isolation of Peripheral Blood Mononuclear Cells (PBMCs) Using a Density Gradient Reagent. Technical Protocol. PROT-IPBMC-V1.1 1018 (2016).

Oetjen et al.: Human bone marrow assessment by single-cell RNA sequencing, mass cytometry, and flow cytometry. JCI Insight. 3(23):7 e124928 (2018) DOI:https://doi.org/10.1172/jci.insight.124928.

PCT/US2020/025778 International Search Report and Written Opinion dated Sep. 16, 2020.

Yescom. All Steel PEX Pipe Tube Cpvc Tubing Cutter up to 1-5/8" Hose Ratchet Style New. Publication [online], https:\\www.amazon.com/Steel-Tubing-Cutter-Ratchet-Style/dp/BOOLSEHSSE. p. 1 (2014).

AATB. Guidance Document, in Evaluation of Body Cooling at Standard D5.400. 2013. American Association of Tissue Banks: McLean, VA. p. 13.

Ahrens et al.: Mesenchymal stem cell content of human vertebral bone marrow. Transplantation, 2004. 78(6): p. 925-929.

(56) References Cited

OTHER PUBLICATIONS

Banfi et al.: Replicative aging and gene expression in long-term cultures of human bone marrow stromal cells. Tissue Eng, 2002. 8(6): p. 901-10.
Bara et al.: Concise review: Bone marrow-derived mesenchymal stem cells change phenotype following in vitro culture: implications for basic research and the clinic. Stem Cells, 2014. 32(7): p. 1713-23.
Baxter et al.: Study of telomere length reveals rapid aging of human marrow stromal cells following in vitro expansion. Stem Cells, 2004. 22(5): p. 675-82.
Bender et al.: Impact of freeze-thaw on isolation of viable CD34+ cells from human cadaveric bone marrow. The FASEB Journal. 34(S1) (2020) Abstract.
Bensidhoum et al.: Homing of in vitro expanded Stro-1- or Stro-1 + human mesenchymal stem cells into the NOD/SCID mouse and their role in supporting human CD34 cell engraftment. Blood, 2004. 103(9): p. 3313-9.
Blashki et al.: Mesenchymal stem cells from cortical bone demonstrate increased clonal incidence, potency, and developmental capacity compared to their bone marrow-derived counterparts. J Tissue Eng, 2016. 7: p. 2041731416661196.
Bork et al.: DNA methylation pattern changes upon long-term culture and aging of human mesenchymal stromal cells. Aging Cell, 2010. 9(1): p. 54-63.
Bruder et al.: Growth kinetics, self-renewal, and the osteogenic potential of purified human mesenchymal stem cells during extensive subcultivation and following cryopreservation. J Cell Biochem, 1997. 64(2): p. 278-94.
Chilima et al.: Designing the optimal manufacturing strategy for an adherent allogeneic cell therapy. BioProcess International, 2016. 14(9): p. 24-32 https://bioprocessintl.com/manufacturing/cell-therapies/designing-optimal-manufacturing-strategy-adherent-allogeneic-cell-therapy/.
Chinnadurai et al.: Immune dysfunctionality of replicative senescent mesenchymal stromal cells is corrected by IFNgamma priming. Blood Adv, 2017. 1(11): p. 628-643.
Choi et al.: Dissecting Cellular Heterogeneity Using Single-Cell RNA Sequencing. Mol Cells, 2019. 42(3): p. 189-199.
ClinicalTrials.gov Identifier: NCT01459107 (2011).
Co-pending U.S. Appl. No. 17/013,379, filed Sep. 4, 2020.
Co-pending U.S. Appl. No. 17/013,389, filed Sep. 4, 2020.
Co-pending U.S. Appl. No. 17/013,400, filed Sep. 4, 2020.
Co-pending U.S. Appl. No. 17/013,407, filed Sep. 4, 2020.
Cox et al.: High abundance of CD271(+) multipotential stromal cells (MSCs) in intramedullary cavities of long bones. Bone, 2012. 50(2): p. 510-7.
CRYO2018: The 55th Annual Meeting of The Society for Cryobiology. CSIC (2018) p. 1-2 Abstract.
CRYO2019: The 56th Annual Meeting of The Society for Cryobiology. CSIC (2019) p. 1-6 Abstracts.
Dennis et al.: The STRO-1+ marrow cell population is multipotential. Cells Tissues Organs, 2002. 170(2-3): p. 73-82.
Digirolamo et al.: Propagation and senescence of human marrow stromal cells in culture: a simple colony forming assay identifies samples with the greatest potential to propagate and differentiate. Br J Haematol, 1999. 107(2): p. 275-81.
Dominici et al.: Minimal criteria for defining multipotent mesenchymal stromal cells. The International Society for Cellular Therapy position statement. Cytotherapy, 2006. 8(4): p. 315-7.
Donnenberg et al.: Clinical implementation of a procedure to prepare bone marrow cells from cadaveric vertebral bodies. Regen Med, 2011. 6(6): p. 701-6.
Dykstra et al.: Concise Review: Fat and Furious: Harnessing the Full Potential of Adipose-Derived Stromal Vascular Fraction. Stem Cells Trans! Med, 2017. 6(4): p. 1096-1108.
Eckardt et al.: Comparison of engraftment and acute GVHD in patients undergoing cryopreserved or fresh allogeneic BMT. Bone Marrow Transplant, 1993. 11(2): p. 125-31.
Ferrari et al.: Beta regression for modeling rates and proportions. J. Applied Statistics, 2004. 31(7): p. 799-815.
Flood et al.: Does practice make perfect? Part 1: The relations between hospital volume and outcomes for selected diagnostic categories. Medical Care, 1984. 22(2): p. 98-114.
Flood et al.: Does practice make perfect? Part II: The relation between vols. and other hospital characteristics. Medical Care, 1984. 22(2): p. 115-125.
Galipeau et al.: International Society for Cellular Therapy perspective on immune functional assays for mesenchymal stromal cells as potency release criterion for advanced phase clinical trials. Cytotherapy, 2016. 18(2): p. 151-9.
Galipeau et al.: Mesenchymal Stromal Cells: Clinical Challenges and Therapeutic Opportunities. Cell Stem Cell, 2018. 22(6): p. 824-833.
Gronthos et al.: Molecular and cellular characterisation of highly purified stromal stem cells derived from human bone marrow. J Cell Sci, 2003. 116(Pt 9): p. 1827-35.
Harrel Jr.: Regression modeling strategies with applications to linear models, logistic regression, and survival analysis. 2nd ed. Springer Series in Statistics. 2001, New York: Springer. 582.
Harrison et al.: Cell therapy-processing economics: small-scale microfactories as a stepping stone toward large-scale macrofactories. Regen Med, 2018. 13(2): p. 159-173.
Heathman et al.: Characterization of human mesenchymal stem cells from multiple donors and the implications for large scale bioprocess development. Biochemical Engineering Journal, 2016. 108: p. 14-23.
Hotta et al.: Long-term Nonhuman Primate Renal Allograft Survival Without Ongoing Immunosuppression in Recipients of Delayed Donor Bone Marrow Transplantation. Transplantation, 2018. 102(4): p. e128-e136.
Hwang et al.: Single-cell RNA sequencing technologies and bioinformatics pipelines. Exp Mol Med, 2018. 50(8): p. 96.
Johnstone: Edit Identification and Characterization of a Large Source of Primary Mesenchymal Stem Cells Tightly Adhered to Bone Surfaces of Human Vertebral Body Marrow Cavities. ISSCR Abstract (2020).
Johnstone et al.: Identification and characterization of a large source of primary mesenchymal stem cells tightly adhered to bone surfaces of human vertebral body marrow cavities. Cytotherapy. (2020) 1-12.
Johnstone et al.: Identification and characterization of a large source of primary mesenchymal stem cells tightly adhered to bone surfaces of human vertebral body marrow cavities. Reprint https://doi.org/10.1101/2020.05.04.076950 (2020) 40 pages.
Jones et al.: Large-scale extraction and characterization of CD271+ multipotential stromal cells from trabecular bone in health and osteoarthritis: implications for bone regeneration strategies based on uncultured or minimally cultured multipotential stromal cells. Arthritis Rheum, 2010. 62(7): p. 1944-54.
Jossen et al.: Manufacturing human mesenchymal stem cells at clinical scale: process and regulatory challenges. Appl Microbiol Biotechnol, 2018. 102(9): p. 3981-3994.
Kawai et al.: Long-term results in recipients of combined HLA-mismatched kidney and bone marrow transplantation without maintenance immunosuppression. Am J Transplant, 2014. 14(7): p. 1599-611.
Knebel et al.: Allocation of scarce resources after a nuclear detonation: setting the context. Disaster Med Public Health Prep, 2011. 5 Suppl 1: p. S20-31.
Lechanteur et al.: Large-scale clinical expansion of mesenchymal stem cells in the GMP-compliant, closed automated Quantum(R) cell expansion system: Comparison with expansion in traditional T-flasks. Stem Cell Research & Therapy, 2014. 4(8): p. 1-11.
Li et al.: Therapeutic Delivery Specifications Identified Through Compartmental Analysis of a Mesenchymal Stromal Cell-Immune Reaction. Sci Rep, 2018. 8(1): p. 6816.
Lioznov et al.: Transportation and cryopreservation may impair haematopoietic stem cell function and engraftment of allogeneic PBSCs, but not BM. Bone Marrow Transplant, 2008. 42(2): p. 121-8.

(56) References Cited

OTHER PUBLICATIONS

Lipsitz et al.: A roadmap for cost-of-goods planning to guide economic production of cell therapy products. Cytotherapy, 2017. 19(12): p. 1383-1391.
Lockhart et al.: Use of Freshly Isolated Human Adipose Stromal Cells for Clinical Applications. Aesthet Surg J, 2017. 37(suppl_3): p. S4-S8.
Mendicino et al.: MSC-based product characterization for clinical trials: an FDA perspective. Cell Stem Cell, 2014. 14(2): p. 141-5.
Miller et al.: Phenotypic and Functional Equivalency of Digested Bone Marrow Mesenchymal Stem Cells to Aspirated Bone Marrow Mesenchymal Stem Cells. The FASEB Journal. 33(S1) (2019) Abstract.
Mizukami et al.: Technologies for large-scale umbilical cord-derived MSC expansion: Experimental performance and cost of g000ds analysis. Biochemical Engineering Journal, 2018. 135: p. 36-48.
Moravcikova et al.: Proteomic Profiling of Native Unpassaged and Culture-Expanded Mesenchymal Stromal Cells (MSC). Cytometry A, 2018. 93(9): p. 894-904.
Muraglia et al.: Clonal mesenchymal progenitors from human bone marrow differentiate in vitro according to a hierarchical model. J Cell Sci, 2000. 113 ( Pt 7): p. 1161-6.
Olsen et al.: Peak MSC—Are We There Yet? Front Med (Lausanne), 2018. 5: p. 178.
Pennington et al.: Evaluation of a Sterling Cycle Controlled Rate Freezing Device for Simultaneous Cryopreservation of Multiple Units. Cryobiology. 91:146-197 (2019) Abstract.
Pereira et al.: Impact of allogeneic stem cell manufacturing decisions on cost of goods, process robustness and reimbursement. Biochemical Engineering Journal, 2018. 137: p. 132-151.
Picard et al.: Cook, Cross-validation of regression models. J . Am. Stat. Assoc, 1984. 79(428):9 pages.
Pittenger et al.: Multilineage potential of adult human mesenchymal stem cells. Science, 1999. 284(5411): p. 143-7.
Quah et al.: Monitoring lymphocyte proliferation in vitro and in vivo with the intracellular fluorescent dye carboxyfluorescein diacetate succinimidyl ester. Nat Protoc, 2007. 2(9): p. 2049-56.
Redaelli et al.: From cytogenomicto epigenomic profiles: monitoring the biologic behavior of in vitro cultured human bone marrow mesenchymal stem cells. Stem Cell Res Ther, 2012. 3(6): p. 47.
Schneeberger et al.: Upper-extremity transplantation using a cell-based protocol to minimize immunosuppression. Ann Surg, 2013. 257(2): p. 345-51.
Schwartz et al.: Explanatory and pragmatic attitudes in therapeutical trials. J Chronic Dis, 1967. 20(8): p. 637-48.
Sherry et al.: The Influence of Warm Ischemic Time on the Viability of Deceased Organ Donor Derived Bone Marrow. The FASEB Journal. 32(S1) Abstract (2018).
Siclari et al.: Mesenchymal progenitors residing close to the bone surface are functionally distinct from those in the central bone marrow. Bone, 2013. 53(2): p. 575-86.
Simaria et al.: Allogeneic cell therapy bioprocess economics and optimization: single-use cell expansion technologies. Biotechnol Bioeng, 2014. 111(1): p. 69-83.
Simmons et al.: Identification of stromal cell precursors in human bone marrow by a novel monoclonal antibody, STRO-1. Blood, 1991. 78(1): p. 55-62.
Spitzer et al.: Twenty Year Follow Up of Histocompatibility Leukocyte Antigen-Matched Kidney and Bone Marrow Co-Transplantation for Multiple Myeloma with End Stage Renal Disease: Lessons Learned. Transplantation, 103(11): 2366-2372 (2019).
Squillaro et al.: Clinical Trials With Mesenchymal Stem Cells: An Update. Cell Transplant, 2016. 25(5): p. 829-48.
Stockschlader et al.: Long-term follow-up of leukaemia patients after related cryopreserved allogeneic bone marrow transplantation. British Journal of Haematology. 96:382-386 (1997).
Stockschlader et al.: Use of cryopreserved bone marrow in allogeneic bone marrow transplantation. Bone Marrow Transplant, 1995. 15(4): p. 569-72.
Stockschlader et al.: Use of cryopreserved bone marrow in unrelated allogeneic transplantation. Bone Marrow Transplant, 1996. 17(2): p. 197-9 (Abstract).
Sutherland et al.: The ISHAGE guidelines for CD34+ cell determination by flow cytometry. International Society of Hematotherapy and Graft Engineering. J Hemather, 1996. 5(3): p. 213-26.
Thompson et al.: Time and Temperature Dependent Ficoll Separation of Aged Whole Blood Neutrophils. The FASEB Journal. 33(S1) Abstract (2019).
Weinstock et al.: Radiologic and nuclear events: contingency planning for hematologists/oncologists. Blood, 2008. 111(12): p. 5440-5.
Woods et al.: Ischemia considerations for the development of an organ and tissue donor derived bone marrow bank. Journal of Translational Medicine. 18:300 (2020) 11 pages.
Woods et al.: Off the shelf cellular therapeutics: Factors to consider during cryopreservation and storage of human cells for clinical use. Cytotherapy, 2016. 18(6): p. 697-711.
Woods et al.: The learning curve and the cost of heart transplantation. Health Sery Res, 1992. 27(2): p. 219-38.
Wright, T., Factors affecting the cost of airplanes. J Aeronautical Sciences, 1936. 3(2): p. 122-128.
Wuchter et al.: Standardization of Good Manufacturing Practice-compliant production of bone marrow-derived human mesenchymal stromal cells for immunotherapeutic applications. Cytotherapy, 2014. 17(2): p. 128-39.
Yamada et al.: Overcoming memory T-cell responses for induction of delayed tolerance in nonhuman primates. Am J Transplant, 2012. 12(2): p. 330-40.
Yusop et al.: Isolation and Characterisation of Mesenchymal Stem Cells from Rat Bone Marrow and the Endosteal Niche: A Comparative Study. Stem Cells Int, 2018. 2018: p. 6869128.
Baumert et al.: Bone marrow of multiorgan donors underutilized: implications for improvement of accessibility of hematopoietic cells for transplantations. Transplantation 93(2):165-171 (2012).
Berz et al.: Cryopreservation of hematopoietic stem cells. Am J Hematol 82(6):463-472 (2007).
Blazar et al.: Successful donor cell engraftment in a recipient of bone marrow from a cadaveric donor. Blood 67(6):1655-1660 (1986).
Hunt. Cryopreservation of Human Stem Cells for Clinical Application: A Review. Transfus Med Hemother 38(2):107-123 (2011).
Kenyon et al.: Effect of depletion of class II bright cells on the immunogenicity and stem cell content of human vertebral body bone marrow. Transplant Proc 27(6):3419 (1995).
Morgenstern et al.: Post-thaw viability of cryopreserved peripheral blood stem cells (PBSC) does not guarantee functional activity: important implications for quality assurance of stem cell transplant programmes. Br J Haematol 174(6):942-951 (2016).
Shu et al.: Development of a reliable low-cost controlled cooling rate instrument for the cryopreservation of hematopoietic stem cells. Cytotherapy 12(2):161-169 (2010).
Thomas et al.: Intravenous infusion of bone marrow in patients receiving radiation and chemotherapy. N Engl J Med 257(11):491-496 (1957).
U.S. Appl. No. 17/013,407 Restriction Requirement dated Nov. 10, 2020.
Bieback et al.: Human Alternatives to Fetal Bovine Serum for the Expansion of Mesenchymal Stromal Cells from Bone Marrow. Stem Cells. 27(9):2331-2341 (2009).
Oseni et al.: Optimization of chondrocyte isolation and characterization for large-scale cartilage tissue engineering. Journal of Surgical Research. 181:41-48 (2013).
Stenn et al.: Dispase, a Neutral Protease From Bacillus Polymyxa, Is a Powerful Fibronectinase and Type IV Collagenase. J Invest Dermatol. 93(2):287-290 (1989).
Suire et al.: Isolation of the stromal-vascular fraction of mouse bone marrow markedly enhances the yield of clonogenic stromal progenitors. Blood. 119(11):e86-e95 (2012).
Thompson: Preparing Skeletons for Research and Teaching from Preserved Human Specimens. Thesis. pp. 1-162 (2015).
U.S. Appl. No. 17/013,379 Restriction Requirement dated Dec. 14, 2020.

(56) References Cited

OTHER PUBLICATIONS

U.S. Appl. No. 17/013,389 First Action Interview dated Dec. 11, 2020.
U.S. Appl. No. 17/013,400 First Action Interview dated Dec. 28, 2020.
U.S. Appl. No. 17/013,407 Office Action dated Dec. 18, 2020.
Warwick et al.: Collagenase Clostridium histolyticum: emerging practice patterns and treatment advances. Journal of Plastic Surgery and Hand Surgery. 50(5):251-326 (2016).
Aimuhem et al.: University of Cincinnati. Cryopreservation and Hyopthermal Storage of Hematopoietic Stem Cells. (2013).
Busilacchi et al.: A novel method to evaluate prethawing viability of cryopreserved CD34+ hematopoietic stem cells for autologous transplantation. The Journal of AABB. Transfusion. 60(7):1529-1535 (2020).
Donnenberg, Ph.D.: Working with Bone Marrow on a Grand Scale. McGowan Retreat. Mar. 2011.
Ferrebee et al.: The Collection, Storage and Preparation of Viable Cadaver Marrow for Intravenous Use. Blood. 14(2):140-147 (1959).
GE Healthcare Life Sciences. Cell Separation Media Reference (2014).
Han et al.: Optimization of human umbilical cord mesenchymal stem cell isolation and culture methods. Cytotechnology. 65(5):819-827 (2013).
Hibino et al.: Comparison of Human Bone Marrow Mononuclear Cells Isolation Methods for Creating Tissue-Engineered Vascular Grafts: Novel Filter System Versus Traditional Density Centrifugation Method. Tissue Engineering. Part C:17(10) (2011).
Johnstone et al.: Identification and characterization of a large source of primary mesenchymal stem cells tightly adhered to bone surfaces of human vertebral body marrow cavities. ScienceDirect. Cytotherapy. 22:617-628 (2020).
Long et al.: Accumulation of CD11b+ Gr-1+ cells in the lung, blood and bone marrow of mice infected with highly pathogenic H5N1 and H1N1 influenza viruses. Archives of Virology. 158(6):1305-1322 (2013).
Miltenyi Biotec: Isolation of Mononuclear Cells from human bone marrow aspirates by density gradient centrifugation. (2008).
U.S. Appl. No. 17/013,379 Office Action dated Feb. 18, 2021.
U.S. Appl. No. 17/013,389 Final Office Action dated Feb. 19, 2021.
U.S. Appl. No. 17/013,389 Non-Final Office Action dated Apr. 7, 2021.
U.S. Appl. No. 17/013,400 Non-Final Office Action dated Apr. 13, 2021.
Walter et al.: Molecular and Functional Phenotypes of Human Bone Marrow-Derived Mesenchymal Stromal Cells Depend on Harvesting Techniques. International Journal of Molecular Sciences. 23.4382:1-12 (2020).
Linch et al.: Bone marrow processing and cryopreservation. Journal of Clinical Pathology. 35(2):186-190 (1982).
PCT/US2020/025778 International Preliminary Report on Patentability dated Oct. 28, 2021.
PCT/US2021/055081 International Search Report and Written Opinion dated Jan. 20, 2021.
U.S. Appl. No. 17/013,400 Final Office Action dated Sep. 2, 2021.
Woods et al.: Packaging considerations for biopreservation. Transfusion Medicine and Hemotherapy 38(2):149-156 (2011).
Chiang et al.: Allogeneic Mesenchymal Stem Cells in Combination with Hyaluronic Acid for the Treatment of Osteoarthritis in Rabbits. PLOS One. 11 (2):e0149835 pp. 1-15 (2016).
U.S. Appl. No. 17/696,779 Office Action dated Jul. 18, 2022.
U.S. Appl. No. 17/199,376 Office Action dated Nov. 17, 2022.
U.S. Appl. No. 17/684,259 Final Office Action dated Sep. 30, 2022.
U.S. Appl. No. 17/684,259 Office Action dated Jun. 13, 2022.
Gorantla et al.: 2007-05-R11A Procedure for preparation of bone marrow cells from cadaveric vertebral bodies. University of Pittsburgh Medical Center. pp. 1-11 (2007).
Eurasian Application No. 202192714 Office Action dated Mar. 30, 2023.
Michalova et al.: Cadaveric bone marrow as potential source of hematopoietic stem cells for transplantation. Chimerism. 2(3):86-87 (2011).

\* cited by examiner

Without Body Cooling: BCT is constant = 0 hours, WIT and CIT vary from their observed minimum to maximum values.

| WIT | CIT=8.93 %Viable CD34 | Total Ischemia | CIT=18.00 %Viable CD34 | Total Ischemia | CIT=24.32 %Viable CD34 | Total Ischemia | CIT=35.84 %Viable CD34 | Total Ischemia | CIT=67.75 %Viable CD34 | Total Ischemia |
|---|---|---|---|---|---|---|---|---|---|---|
| 0.05 | 94.09% | 8.98 | 88.54% | 18.05 | 84.75% | 24.37 | 80.90% | 35.89 | 94.80% | 67.80 |
| 0.51 | 94.03% | 9.44 | 88.44% | 18.51 | 84.63% | 24.83 | 80.75% | 36.35 | 94.75% | 68.30 |
| 0.97 | 93.97% | 9.90 | 88.34% | 18.97 | 84.51% | 25.29 | 80.61% | 36.81 | 94.70% | 68.80 |
| 1.43 | 93.92% | 10.36 | 88.24% | 19.43 | 84.38% | 25.75 | 80.46% | 37.27 | 94.64% | 69.30 |
| 1.89 | 93.86% | 10.82 | 88.14% | 19.89 | 84.25% | 26.21 | 80.31% | 37.73 | 94.59% | 69.80 |
| 2.35 | 93.80% | 11.28 | 88.04% | 20.35 | 84.13% | 26.67 | 80.16% | 38.19 | 94.54% | 70.47 |
| 2.81 | 93.73% | 11.74 | 87.94% | 20.81 | 84.00% | 27.13 | 80.01% | 38.65 | | |
| 3.27 | 93.67% | 12.20 | 87.83% | 21.27 | 83.87% | 27.59 | 79.86% | 39.11 | | |
| 3.73 | 93.61% | 12.66 | 87.73% | 21.73 | 83.74% | 28.05 | 79.71% | 39.57 | | |
| 4.19 | 93.55% | 13.12 | 87.63% | 22.19 | 83.61% | 28.51 | 79.56% | 40.03 | | |
| 4.65 | 93.49% | 13.58 | 87.52% | 22.65 | 83.48% | 28.97 | 79.40% | 40.49 | | |
| 5.11 | 93.42% | 14.04 | 87.42% | 23.11 | 83.35% | 29.43 | 79.25% | 40.95 | | |
| 5.57 | 93.36% | 14.50 | 87.31% | 23.57 | 83.22% | 29.89 | 79.09% | 41.41 | | |
| 6.03 | 93.30% | 14.96 | 87.20% | 24.03 | 83.09% | 30.35 | 78.94% | 41.87 | | |
| 6.49 | 93.23% | 15.42 | 87.09% | 24.49 | 82.95% | 30.81 | 78.78% | 42.33 | | |
| 6.95 | 93.17% | 15.88 | 86.98% | 24.95 | 82.82% | 31.27 | 78.62% | 42.79 | | |
| 7.41 | 93.10% | 16.34 | 86.87% | 25.41 | 82.68% | 31.73 | 78.47% | 43.25 | | |
| 7.87 | 93.03% | 16.80 | 86.76% | 25.87 | 82.55% | 32.19 | 78.31% | 43.71 | | |
| 8.33 | 92.97% | 17.26 | 86.65% | 26.33 | 82.41% | 32.65 | 78.15% | 44.17 | | |
| 8.79 | 92.90% | 17.72 | 86.54% | 26.79 | 82.27% | 33.11 | 77.99% | 44.63 | | |
| 9.25 | 92.83% | 18.18 | 86.43% | 27.25 | 82.13% | 33.57 | 77.82% | 45.09 | | |
| 9.71 | 92.77% | 18.64 | 86.32% | 27.71 | 81.99% | 34.03 | 77.66% | 45.55 | | |
| 10.17 | 92.70% | 19.10 | 86.20% | 28.17 | 81.85% | 34.49 | 77.50% | 46.01 | | |
| 10.63 | 92.63% | 19.56 | 85.38% | 28.63 | 81.71% | 34.95 | 77.34% | 46.47 | | |
| 11.09 | 92.56% | 20.02 | 85.27% | 29.09 | 81.57% | 35.41 | 77.17% | 46.93 | | |
| 11.55 | 92.49% | 20.48 | 85.15% | 29.55 | 81.43% | 35.87 | 77.01% | 47.39 | | |
| 12.01 | 92.42% | 20.94 | 85.04% | 30.01 | 81.28% | 36.33 | 76.84% | 47.85 | | |
| 12.47 | 92.35% | 21.40 | 84.92% | 30.47 | 81.14% | 36.79 | 76.67% | 48.31 | | |
| 12.93 | 92.27% | 21.86 | 84.81% | 30.93 | 81.00% | 37.25 | 76.50% | 48.77 | | |
| 13.40 | 92.20% | 22.33 | 84.69% | 31.40 | 80.85% | 37.72 | 76.33% | 49.24 | | |

FIG. 12A

With Body Cooling: WIT is constant at its minimum = 0.05 hours, BCT and CIT vary from their observed minimum to maximum values.

| CIT | BCT=1.07 %Viable CD34 | Total Ischemia | BCT=1.62 %Viable CD34 | Total Ischemia | BCT=2.20 %Viable CD34 | Total Ischemia | BCT=3.39 %Viable CD34 | Total Ischemia | BCT=6.00 %Viable CD34 | Total Ischemia |
|---|---|---|---|---|---|---|---|---|---|---|
| 7.40 | 93.74% | 8.52 | 93.11% | 9.07 | 92.43% | 9.65 | 90.98% | 10.84 | 87.80% | 13.45 |
| 8.90 | 92.80% | 10.02 | 92.10% | 10.57 | 91.34% | 11.15 | 89.73% | 12.34 | 86.22% | 14.95 |
| 10.40 | 91.82% | 11.52 | 91.04% | 12.07 | 90.20% | 12.65 | 88.42% | 13.84 | 84.57% | 16.45 |
| 11.90 | 90.78% | 13.02 | 89.93% | 13.57 | 89.01% | 14.15 | 87.07% | 15.34 | 82.89% | 17.95 |
| 13.40 | 89.72% | 14.52 | 88.79% | 15.07 | 87.78% | 15.65 | 85.68% | 16.84 | 81.17% | 19.45 |
| 13.55 | 89.61% | 14.67 | 88.67% | 15.22 | 87.66% | 15.80 | 85.53% | 16.99 | 81.00% | 19.60 |
| 14.90 | 88.63% | 16.02 | 87.62% | 16.57 | 86.53% | 17.15 | 84.27% | 18.34 | 79.45% | 20.95 |
| 16.40 | 87.52% | 17.52 | 86.44% | 18.07 | 85.28% | 18.65 | 82.85% | 19.84 | 77.74% | 22.45 |
| 17.90 | 86.42% | 19.02 | 85.27% | 19.57 | 84.03% | 20.15 | 81.45% | 21.34 | 76.07% | 23.95 |
| 19.40 | 85.34% | 19.62 | 84.11% | 20.17 | 82.80% | 20.75 | 80.08% | 21.94 | 74.44% | 24.55 |
| 20.90 | 84.28% | 20.52 | 82.99% | 21.07 | 81.60% | 21.65 | 78.76% | 22.84 | 72.89% | 25.45 |
| 22.40 | 83.26% | 20.63 | 81.91% | 21.18 | 80.46% | 21.76 | 77.50% | 22.95 | 71.42% | 25.56 |
| 23.90 | 82.29% | 22.02 | 80.89% | 22.57 | 79.39% | 23.15 | 76.31% | 24.34 | 70.04% | 26.95 |
| 25.40 | 81.39% | 23.52 | 79.94% | 24.07 | 78.38% | 24.65 | 75.22% | 25.84 | 68.78% | 28.45 |
| 26.90 | 80.57% | 25.02 | 79.07% | 25.57 | 77.47% | 26.15 | 74.22% | 27.34 | 67.65% | 29.95 |
| 28.40 | 79.83% | 25.84 | 78.29% | 26.39 | 76.66% | 26.97 | 73.33% | 28.16 | 66.64% | 30.77 |
| 29.90 | 79.19% | 26.52 | 77.62% | 27.07 | 75.95% | 27.65 | 72.56% | 28.84 | 65.77% | 31.45 |
| 31.40 | 78.65% | 28.02 | 77.05% | 28.57 | 75.35% | 29.15 | 71.92% | 30.34 | 65.05% | 32.95 |
| 32.90 | 78.22% | 29.52 | 76.60% | 30.07 | 74.88% | 30.65 | 71.41% | 31.84 | 64.48% | 34.45 |
| 34.40 | 77.91% | 31.02 | 76.27% | 31.57 | 74.53% | 32.15 | 71.03% | 33.34 | 64.06% | 35.95 |
| 35.90 | 77.71% | 32.52 | 76.06% | 33.07 | 74.31% | 33.65 | 70.79% | 34.84 | 63.79% | 37.45 |
| 37.40 | 77.62% | 32.73 | 75.97% | 33.28 | 74.22% | 33.86 | 70.70% | 35.05 | 63.69% | 37.66 |
| 38.90 | 77.66% | 34.02 | 76.01% | 34.57 | 74.27% | 35.15 | 70.74% | 36.34 | 63.74% | 38.95 |
| 40.40 | 77.82% | 35.52 | 76.18% | 36.07 | 74.44% | 36.65 | 70.93% | 37.84 | 63.94% | 40.45 |
| 41.90 | 78.09% | 37.02 | 76.47% | 37.57 | 74.74% | 38.15 | 71.25% | 39.34 | 64.31% | 41.95 |

FIG. 12B

With Body Cooling: CIT is constant at its minimum = 7.4 hours, BCT and WIT vary from their observed minimum to observed maximum values.

| BCT | WIT=0.05 %Viable CD34 | Total Ischemia | WIT=1.95 %Viable CD34 | Total Ischemia | WIT=2.48 %Viable CD34 | Total Ischemia | WIT=3.30 %Viable CD34 | Total Ischemia | WIT=8.95 %Viable CD34 | Total Ischemia |
|---|---|---|---|---|---|---|---|---|---|---|
| 1.07 | 93.74% | 8.52 | 93.49% | 10.42 | 93.41% | 10.95 | 93.30% | 11.77 | 92.47% | 17.42 |
| 1.81 | 92.89% | 9.26 | 92.61% | 11.16 | 92.53% | 11.69 | 92.40% | 12.51 | 91.49% | 18.16 |
| 2.55 | 92.01% | 10.00 | 91.70% | 11.90 | 91.61% | 12.43 | 91.47% | 13.25 | 90.47% | 18.90 |
| 3.29 | 91.10% | 10.74 | 90.76% | 12.64 | 90.67% | 13.17 | 90.52% | 13.99 | 89.43% | 19.64 |
| 4.03 | 90.19% | 11.48 | 89.82% | 13.38 | 89.72% | 13.91 | 89.56% | 14.73 | 88.38% | 20.38 |
| 4.77 | 89.28% | 12.22 | 88.88% | 14.12 | 88.77% | 14.65 | 88.60% | 15.47 | 87.34% | 21.12 |
| 5.51 | 88.38% | 12.96 | 87.96% | 14.86 | 87.84% | 15.39 | 87.66% | 16.21 | 86.31% | 21.86 |
| 6.25 | 87.51% | 13.70 | 87.06% | 15.60 | 86.94% | 16.13 | 86.74% | 16.95 | 85.33% | 22.60 |
| 6.99 | 86.68% | 14.44 | 86.21% | 16.34 | 86.08% | 16.87 | 85.87% | 17.69 | 84.39% | 23.34 |
| 7.73 | 85.90% | 15.18 | 85.41% | 17.08 | 85.27% | 17.61 | | | 83.51% | 24.08 |
| 8.47 | 85.18% | 15.92 | 84.67% | 17.82 | 84.53% | 18.35 | | | | |
| 9.21 | 84.53% | 16.66 | 84.01% | 18.56 | 83.86% | 19.09 | | | | |
| 9.95 | 83.97% | 17.40 | 83.43% | 19.30 | 83.28% | 19.83 | | | | |
| 10.69 | 83.50% | 18.14 | 82.95% | 20.04 | 82.80% | 20.57 | | | | |
| 11.43 | 83.12% | 18.88 | 82.57% | 20.78 | 82.41% | 21.31 | | | | |
| 12.17 | 82.85% | 19.62 | 82.29% | 21.52 | 82.13% | 22.05 | | | | |
| 12.91 | 82.69% | 20.36 | 82.12% | 22.26 | | | | | | |
| 13.65 | 82.63% | 21.10 | | | | | | | | |
| 14.39 | 82.68% | 21.84 | | | | | | | | |
| 15.13 | 82.84% | 22.58 | | | | | | | | |
| 15.87 | 83.11% | 23.32 | | | | | | | | |
| 16.61 | 83.48% | 24.06 | | | | | | | | |
| 17.35 | 83.94% | 24.80 | | | | | | | | |
| 18.09 | 84.50% | 25.54 | | | | | | | | |
| 18.83 | 85.14% | 26.28 | | | | | | | | |
| 19.57 | 85.85% | 27.02 | | | | | | | | |
| 20.31 | 86.63% | 27.76 | | | | | | | | |
| 21.05 | 87.46% | 28.50 | | | | | | | | |
| 21.79 | 88.33% | 29.24 | | | | | | | | |
| 22.50 | 89.19% | 29.95 | | | | | | | | |

FIG. 12C

Without Body Cooling: BCT = 0 hours, WIT and CIT are varied from their observed minimum to maximum values.

| WIT | CIT=11.70 CFU-TOTAL | Total Ischemia | CIT=23.75 CFU-TOTAL | Total Ischemia | CIT=27.41 CFU-TOTAL | Total Ischemia | CIT=39.75 CFU-TOTAL | Total Ischemia | CIT=67.75 CFU-TOTAL | Total Ischemia |
|---|---|---|---|---|---|---|---|---|---|---|
| 1.08 | 693.630 | 12.78 | 639.001 | 24.83 | 622.416 | 28.49 | 566.465 | 40.83 | 439.527 | 68.83 |
| 1.83 | 686.798 | 13.53 | 632.170 | 25.58 | 615.585 | 29.24 | 559.634 | 41.58 | 432.696 | 69.58 |
| 2.58 | 679.967 | 14.28 | 625.339 | 26.33 | 608.754 | 29.99 | 552.803 | 42.33 | 425.865 | 70.33 |
| 3.33 | 673.136 | 15.03 | 618.507 | 27.08 | 601.922 | 30.74 | 545.972 | 43.08 | | |
| 4.08 | 666.305 | 15.78 | 611.676 | 27.83 | 595.091 | 31.49 | 539.140 | 43.83 | | |
| 4.83 | 659.474 | 16.53 | 604.845 | 28.58 | 588.260 | 32.24 | 532.309 | 44.58 | | |
| 5.58 | 652.642 | 17.28 | 598.014 | 29.33 | 581.429 | 32.99 | 525.478 | 45.33 | | |
| 6.33 | 645.811 | 18.03 | 591.183 | 30.08 | 574.598 | 33.74 | 518.647 | 46.08 | | |
| 7.08 | 638.980 | 18.78 | 584.351 | 30.83 | 567.766 | 34.49 | 511.816 | 46.83 | | |
| 7.83 | 632.149 | 19.53 | 577.520 | 31.58 | 560.935 | 35.24 | 504.984 | 47.58 | | |
| 8.58 | 625.318 | 20.28 | 570.689 | 32.33 | 554.104 | 35.99 | 498.153 | 48.33 | | |
| 9.33 | 618.486 | 21.03 | 563.858 | 33.08 | 547.273 | 36.74 | 491.322 | 49.13 | | |
| 10.08 | 611.655 | 21.78 | 557.027 | 33.83 | 540.442 | 37.49 | | | | |
| 10.83 | 604.824 | 22.53 | 550.195 | 34.58 | 533.610 | 38.24 | | | | |
| 11.58 | 597.993 | 23.28 | 543.364 | 35.33 | 526.779 | 38.99 | | | | |
| 12.33 | 591.162 | 24.03 | 536.533 | 36.08 | 519.948 | 39.74 | | | | |
| 13.40 | 581.416 | 25.10 | 526.787 | 37.15 | 510.202 | 40.81 | | | | |

FIG. 13A

With Body Cooling: WIT is constant at its minimum (0.05 hours), while BCT and CIT are varied from their observed minimum to maximum values.

| CIT | BCT=1.07 CFU-TOTAL | Total Ischemia | BCT=6.54 CFU-TOTAL | Total Ischemia | BCT=9.78 CFU-TOTAL | Total Ischemia | BCT=15.00 CFU-TOTAL | Total Ischemia | BCT=22.50 CFU-TOTAL | Total Ischemia |
|---|---|---|---|---|---|---|---|---|---|---|
| 7.40 | 624.773 | 8.52 | | | | | | | | |
| 8.90 | 617.973 | 10.02 | | | | | | | | |
| 10.40 | 611.173 | 11.52 | | | | | | | | |
| 11.90 | 604.372 | 13.02 | | | | | | | | |
| 13.40 | 597.572 | 14.52 | | | | | | | | |
| 14.90 | 590.772 | 16.02 | | | | | | | | |
| 16.40 | 583.972 | 17.52 | | | | | | | | |
| 17.90 | 577.171 | 19.02 | 248.787 | 13.99 | | | | | | |
| 19.40 | 570.371 | 20.52 | 241.987 | 15.49 | | | | | | |
| 20.90 | 563.571 | 22.02 | 235.187 | 16.99 | | | | | | |
| 22.40 | 556.771 | 23.52 | 228.386 | 18.49 | | | | | | |
| 23.90 | 549.970 | 25.02 | 221.586 | 19.99 | 123.613 | 17.23 | | | | |
| 25.40 | 543.170 | 26.52 | 214.786 | 21.49 | 116.813 | 18.73 | | | | |
| 26.90 | 536.370 | 28.02 | 207.986 | 22.99 | 110.012 | 20.23 | | | | |
| 28.40 | 529.570 | 29.52 | 201.185 | 24.49 | 103.212 | 21.73 | | | | |
| 29.90 | 522.769 | 31.02 | 194.385 | 25.99 | 96.412 | 23.23 | 74.566 | 22.45 | | |
| 31.40 | 515.969 | 32.52 | 187.585 | 27.49 | | | | | | |
| 32.90 | 509.169 | 34.02 | 180.785 | 28.99 | | | | | | |
| 34.40 | | | 173.984 | 30.49 | | | | | 333.801 | 29.95 |
| 35.90 | | | 167.184 | 31.99 | | | | | 327.001 | 31.45 |
| 37.40 | | | | | | | | | 320.201 | 32.95 |
| 38.90 | | | | | | | | | 313.400 | 34.45 |
| 41.03 | | | | | | | | | 306.600 | 35.95 |
| | | | | | | | | | 299.800 | 37.45 |
| | | | | | | | | | 293.000 | 38.95 |
| | | | | | | | | | 286.199 | 40.45 |
| | | | | | | | | | 279.399 | 41.95 |

FIG. 13B

With Body Cooling: CIT is constant at its minimum value = 7.4 hours, BCT and WIT are varied from their observed minimum to observed maximum values.

| BCT | WIT=0.05 CFU-TOTAL | Total Ischemia | WIT=1.96 CFU-TOTAL | Total Ischemia | WIT=2.48 CFU-TOTAL | Total Ischemia | WIT=3.42 CFU-TOTAL | Total Ischemia | WIT=8.95 CFU-TOTAL | Total Ischemia |
|---|---|---|---|---|---|---|---|---|---|---|
| 1.07 | 624.77 | 8.52 | 607.38 | 10.43 | 602.64 | 10.95 | 594.08 | 11.89 | 543.71 | 17.42 |
| 2.07 | 540.59 | 9.52 | 523.19 | 11.43 | 518.46 | 11.95 | | | 459.53 | 18.42 |
| 3.07 | 463.32 | 10.52 | 445.92 | 12.43 | 441.18 | 12.95 | | | 382.25 | 19.42 |
| 4.07 | 392.96 | 11.52 | 375.56 | 13.43 | 370.82 | 13.95 | | | 311.89 | 20.42 |
| 5.07 | 329.51 | 12.52 | 312.11 | 14.43 | 307.37 | 14.95 | | | 248.44 | 21.42 |
| 6.07 | 272.97 | 13.52 | 255.57 | 15.43 | 250.84 | 15.95 | | | 191.91 | 22.42 |
| 7.07 | 223.35 | 14.52 | 205.95 | 16.43 | 201.21 | 16.95 | | | | |
| 8.07 | 180.64 | 15.52 | 163.24 | 17.43 | 158.50 | 17.95 | | | | |
| 9.07 | 144.83 | 16.52 | 127.44 | 18.43 | 122.70 | 18.95 | | | | |
| 10.07 | 115.95 | 17.52 | | | | | | | | |
| 11.07 | 93.97 | 18.52 | | | | | | | | |
| 12.07 | 78.91 | 19.52 | | | | | | | | |
| 13.07 | 70.76 | 20.52 | | | | | | | | |
| 14.07 | 69.52 | 21.52 | | | | | | | | |
| 15.07 | 75.19 | 22.52 | | | | | | | | |
| 16.07 | 87.77 | 23.52 | | | | | | | | |
| 17.07 | 107.27 | 24.52 | | | | | | | | |
| 18.07 | 133.68 | 25.52 | | | | | | | | |
| 19.07 | 167.00 | 26.52 | | | | | | | | |
| 20.07 | 207.23 | 27.52 | | | | | | | | |
| 21.07 | 254.37 | 28.52 | | | | | | | | |
| 22.50 | 333.80 | 29.95 | | | | | | | | |

FIG. 13C

Without Body Cooling: BCT is constant = 0 hours, WIT and CIT are varied from their observed minimum to observed maximum values.

| WIT | CIT=11.70 CFU-GEM | Total Ischemia | CIT=23.75 CFU-GEM | Total Ischemia | CIT=27.00 CFU-GEM | Total Ischemia | CIT=40.50 CFU-GM | Total Ischemia | CIT=67.75 CFU-GM | Total Ischemia |
|---|---|---|---|---|---|---|---|---|---|---|
| 1.08 | 96.457 | 12.78 | 97.503 | 24.58 | 97.814 | 28.08 | 99.012 | 41.58 | 101.429 | 68.83 |
| 1.68 | 91.589 | 13.38 | 92.636 | 25.18 | 92.946 | 28.68 | 94.144 | 42.18 | 96.561 | 69.43 |
| 2.28 | 86.721 | 13.98 | 87.768 | 25.78 | 88.078 | 29.28 | 89.276 | 42.78 | 91.694 | 70.03 |
| 2.88 | 81.853 | 14.58 | 82.900 | 26.38 | 83.211 | 29.88 | 84.408 | 43.38 | 86.826 | 70.63 |
| 3.48 | 76.985 | 15.18 | 78.032 | 26.98 | 78.343 | 30.48 | 79.541 | 43.98 | 81.958 | 71.23 |
| 4.08 | 72.118 | 15.78 | 73.165 | 27.58 | 73.475 | 31.08 | 74.673 | 44.58 | 77.090 | 71.83 |
| 4.68 | 67.250 | 16.38 | 68.297 | 28.18 | 68.607 | 31.68 | 69.805 | 45.18 | | |
| 5.28 | 62.382 | 16.98 | 63.429 | 28.78 | 63.740 | 32.28 | 64.937 | 45.78 | | |
| 5.88 | 57.514 | 17.58 | 58.561 | 29.38 | 58.872 | 32.88 | 60.069 | 46.38 | | |
| 6.48 | 52.647 | 18.18 | 53.693 | 29.98 | 54.004 | 33.48 | 55.202 | 46.98 | | |
| 7.08 | 47.779 | 18.78 | 48.826 | 30.58 | 49.136 | 34.08 | 50.334 | 47.58 | | |
| 7.68 | 42.911 | 19.38 | 43.958 | 31.18 | 44.268 | 34.68 | 45.466 | 48.18 | | |
| 8.28 | 38.043 | 19.98 | 39.090 | 31.78 | 39.401 | 35.28 | 40.598 | 48.78 | | |
| 8.88 | 33.175 | 20.58 | 34.222 | 32.38 | 34.533 | 35.88 | 35.731 | 49.38 | | |
| 9.48 | 28.308 | 21.18 | 29.355 | 32.98 | 29.665 | 36.48 | 30.863 | 49.98 | | |
| 10.08 | 23.440 | 21.78 | 24.487 | 33.58 | 24.797 | 37.08 | 25.995 | 50.58 | | |
| 10.68 | 18.572 | 22.38 | 19.619 | 34.18 | 19.930 | 37.68 | 21.127 | 51.18 | | |
| 11.28 | 13.704 | 22.98 | 14.751 | 34.78 | 15.062 | 38.28 | 16.260 | 51.78 | | |
| 11.88 | 8.837 | 23.58 | 9.884 | 35.38 | 10.194 | 38.88 | 11.392 | 52.38 | | |
| 12.48 | 3.969 | 24.18 | 5.016 | 35.98 | 5.326 | 39.48 | 6.524 | 52.98 | | |
| 13.04 | 0.000 | 24.74 | 0.473 | 36.54 | 0.783 | 40.04 | 1.981 | 53.54 | | |

FIG. 14A

With Body Cooling: WIT is constant at its minimum value = 0.05 hours, BCT and CIT are varied from their observed minimum to observed maximum values.

| CIT | BCT=1.07 CFU-TOTAL | Total Ischemia | BCT=6.04 CFU-TOTAL | Total Ischemia | BCT=9.78 CFU-TOTAL | Total Ischemia | BCT=13.90 CFU-TOTAL | Total Ischemia | BCT=22.50 CFU-TOTAL | Total Ischemia |
|---|---|---|---|---|---|---|---|---|---|---|
| 7.40 | 98.515 | 8.52 | 71.035 | 13.49 | 50.355 | 17.23 | 27.575 | 21.35 | 0.00 | 29.95 |
| 8.40 | 98.604 | 9.52 | 71.123 | 14.49 | 50.444 | 18.23 | 27.663 | 22.35 | 0.00 | 30.95 |
| 9.40 | 98.692 | 10.52 | 71.212 | 15.49 | 50.533 | 19.23 | 27.752 | 23.35 | 0.00 | 31.95 |
| 10.40 | 98.781 | 11.52 | 71.301 | 16.49 | 50.621 | 20.23 | 27.841 | 24.35 | 0.00 | 32.95 |
| 11.40 | 98.870 | 12.52 | 71.389 | 17.49 | 50.710 | 21.23 | 27.929 | 25.35 | 0.00 | 33.95 |
| 12.40 | 98.959 | 13.52 | 71.478 | 18.49 | 50.799 | 22.23 | 28.018 | 26.35 | 0.00 | 34.95 |
| 13.40 | 99.047 | 14.52 | 71.567 | 19.49 | 50.887 | 23.23 | 28.107 | 27.35 | 0.00 | 35.95 |
| 14.40 | 99.136 | 15.52 | 71.656 | 20.49 | 50.976 | 24.23 | 28.196 | 28.35 | 0.00 | 36.95 |
| 15.40 | 99.225 | 16.52 | 71.744 | 21.49 | 51.065 | 25.23 | 28.284 | 29.35 | | |
| 16.40 | 99.314 | 17.52 | 71.833 | 22.49 | 51.154 | 26.23 | 28.373 | 30.35 | | |
| 17.40 | 99.402 | 18.52 | 71.922 | 23.49 | 51.242 | 27.23 | 28.462 | 31.35 | | |
| 18.40 | 99.491 | 19.52 | 72.010 | 24.49 | 51.331 | 28.23 | 28.550 | 32.35 | | |
| 19.40 | 99.580 | 20.52 | 72.099 | 25.49 | 51.420 | 29.23 | 28.639 | 33.35 | | |
| 20.40 | 99.668 | 21.52 | 72.188 | 26.49 | 51.508 | 30.23 | 28.728 | 34.35 | | |
| 21.40 | 99.757 | 22.52 | 72.277 | 27.49 | 51.597 | 31.23 | 28.817 | 35.35 | | |

FIG. 14B

With Body Cooling: CIT is constant at its minimum value = 7.4 hours, BCT and WIT are varied from their observed minimum to observed maximum values.

| BCT | WIT=0.05 CFU-TOTAL | Total Ischemia | WIT=0.10 CFU-TOTAL | Total Ischemia | WIT=1.54 CFU-TOTAL | Total Ischemia | WIT=1.92 CFU-TOTAL | Total Ischemia | WIT=2.49 CFU-TOTAL | Total Ischemia |
|---|---|---|---|---|---|---|---|---|---|---|
| 1.07 | 98.52 | 8.52 | 98.11 | 8.57 | 86.43 | 10.01 | 83.34 | 10.39 | 78.72 | 10.96 |
| 2.07 | 92.99 | 9.52 | 92.58 | 9.57 | 80.90 | 11.01 | 77.81 | 11.39 | 73.19 | 11.96 |
| 3.07 | 87.46 | 10.52 | 87.05 | 10.57 | 75.37 | 12.01 | 72.29 | 12.39 | 67.66 | 12.96 |
| 4.07 | 81.93 | 11.52 | 81.52 | 11.57 | 69.84 | 13.01 | 66.76 | 13.39 | 62.13 | 13.96 |
| 5.07 | 76.40 | 12.52 | 75.99 | 12.57 | 64.31 | 14.01 | 61.23 | 14.39 | 56.60 | 14.96 |
| 6.07 | 70.87 | 13.52 | 70.46 | 13.57 | 58.78 | 15.01 | 55.70 | 15.39 | 51.07 | 15.96 |
| 7.07 | 65.34 | 14.52 | 64.93 | 14.57 | 53.25 | 16.01 | 50.17 | 16.39 | 45.54 | 16.96 |
| 8.07 | 59.81 | 15.52 | 59.40 | 15.57 | 47.72 | 17.01 | 44.64 | 17.39 | 40.01 | 17.96 |
| 9.07 | 54.28 | 16.52 | 53.88 | 16.57 | 42.19 | 18.01 | 39.11 | 18.39 | 34.49 | 18.96 |
| 10.07 | 48.75 | 17.52 | 48.35 | 17.57 | 36.66 | 19.01 | 33.58 | 19.39 | 28.96 | 19.96 |
| 11.07 | 43.22 | 18.52 | 42.82 | 18.57 | 31.13 | 20.01 | 28.05 | 20.39 | | |
| 12.07 | 37.69 | 19.52 | 37.29 | 19.57 | 25.60 | 21.01 | 22.52 | 21.39 | | |
| 13.07 | 32.16 | 20.52 | 31.76 | 20.57 | 20.08 | 22.01 | 16.99 | 22.39 | | |
| 14.07 | 26.63 | 21.52 | 26.23 | 21.57 | 14.55 | 23.01 | 11.46 | 23.39 | | |
| 15.07 | 21.11 | 22.52 | 20.70 | 22.57 | 9.02 | 24.01 | 5.93 | 24.39 | | |
| 16.07 | 15.58 | 23.52 | 15.17 | 23.57 | 3.49 | 25.01 | 0.40 | 25.39 | | |
| 17.07 | 10.05 | 24.52 | 9.64 | 24.57 | 0.00 | 26.01 | 0.00 | 26.39 | | |
| 18.07 | 4.52 | 25.52 | 4.11 | 25.57 | 0.00 | 27.01 | 0.00 | 27.39 | | |
| 19.07 | 0.00 | 26.52 | 0.00 | 26.57 | 0.00 | 28.01 | 0.00 | 28.39 | | |
| 20.07 | 0.00 | 27.52 | 0.00 | 27.57 | 0.00 | 29.01 | 0.00 | 29.39 | | |
| 21.07 | 0.00 | 28.52 | 0.00 | 28.57 | 0.00 | 30.01 | | | | |
| 22.50 | 0.00 | 29.52 | 0.00 | 30.00 | 0.00 | 31.44 | | | | |

FIG. 14C

FIG. 16A
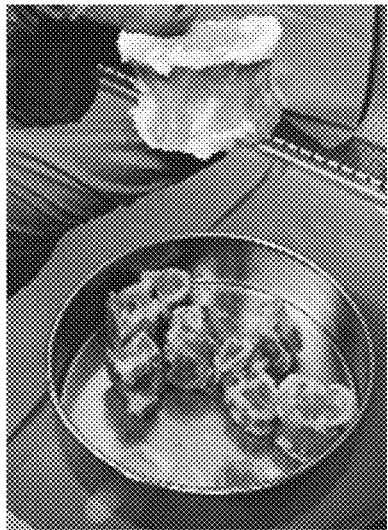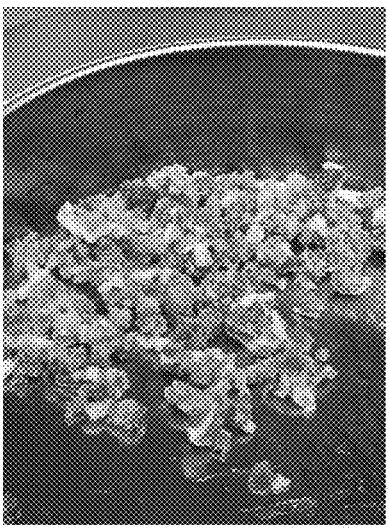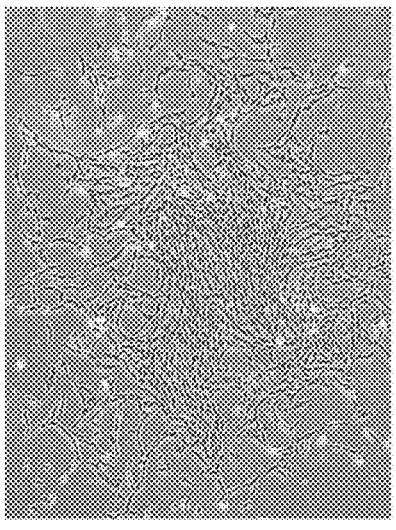
FIG. 16B   FIG. 16C   FIG. 16D

|  | Facility | | | Bone Type | | | Body Cooled? | | |
|---|---|---|---|---|---|---|---|---|---|
|  | A | B | p | VB | IL | p | Yes | No | p |
| Bone Type (%VB) | 27.0% | 100% | —[a] | — | — | — | 64.7% | 79.2% | 0.18 |
| Donor Sex (% Male) | 78.7% | 73.7% | 0.67 | 74.4% | 82.6% | 0.44 | 77.8% | 77.8% | 0.95 |
| Donor Age (yrs) | 41.18 | 42.44 | 0.65 | 41.0 | 42.9 | 0.52 | 40.78 | 43.33 | 0.32 |
| Experience | 26.86 | 12.00 | <0.0000 | 20.9 | 24.1 | 0.45 | 23.74 | 18.0 | 0.12 |
| Warm Ischemia (hrs) | 3.55 | 2.13 | 0.003 | 2.90 | 3.47 | 0.38 | 2.65 | 3.98 | 0.04 |
| Body Cooling (hrs) | 7.95 | 5.09 | 0.08 | 6.32 | 8.51 | 0.09 | 10.28 | 0.0 | — |
| Cold Ischemia (hrs) | 19.55 | 28.38 | 0.004 | 22.85 | 21.68 | 0.66 | 19.51 | 28.83 | 0.009 |
| Total Ischemia (hrs) | 31.04 | 35.60 | 0.07 | 32.07 | 33.66 | 0.56 | 32.44 | 32.82 | 0.91 |
| Outcomes | | | | | | | | | |
| %CD34+ Viability | 79.33 | 76.01 | 0.57 | 80.17 | 73.84 | 0.29 | 72.75 | 89.86 | 0.0001 |
| CFU-TOTAL/$10^5$ TNC | 222.58 | 325.75 | 0.36 | 341.29 | 97.44 | 0.02 | 100.16 | 659.00 | <0.0000 |
| CFU-GM/$10^5$ TNC | 28.38 | 64.31 | 0.04 | 50.46 | 18.03 | 0.04 | 18.52 | 94.85 | <0.0000 |

[a] Significance test cannot be performed because Facility B processed only vertebrae.
VB = Vertebrae, IL = Ilia

| Predictor | Beta Regression Model | | | | Leave-One-Out Bootstrap Cross-Validation | | | | | |
|---|---|---|---|---|---|---|---|---|---|---|
| | Coefficient | Standard Error | p | Odds Ratio | Coefficient | Standard Error | Z | p | 95% C.I. | |
| $\beta_0$ Constant | 3.11504 | 0.71 | <0.0001 | | 3.15149 | 0.86 | 3.66 | <0.0001 | 1.465 | 4.838 |
| $\beta_1$ Experience | -0.02482 | 0.02 | 0.09 | 0.9755 | -0.02282 | 0.02 | -1.05 | 0.29 | -0.065 | 0.020 |
| $\beta_2$ Facility × Experience | 0.03203 | 0.02 | 0.07 | 1.0325 | 0.03023 | 0.02 | 1.51 | 0.13 | -0.009 | 0.070 |
| $\beta_3$ Bone Type (VB=1) | 0.22102 | 0.26 | 0.40 | 1.2473 | 0.21252 | 0.28 | 1.21 | 0.22 | -4.225 | 17.996 |
| $\beta_4$ Warm Ischemia (hrs)$^a$ | -0.03423 | 0.05 | 0.52 | 0.9663 | -0.03775 | 0.06 | -0.63 | 0.53 | -0.156 | 0.080 |
| $\beta_5$ Body Cooling (hrs) | -0.16779 | 0.05 | 0.002 | 0.8455 | -0.17062 | 0.06 | -2.67 | 0.008 | -0.296 | -0.045 |
| $\beta_6$ Body Cooling Squared | 0.00592 | 0.003 | 0.03 | 1.0059 | 0.00609 | 0.003 | 1.84 | 0.06 | 0.004 | 0.012 |
| $\beta_7$ Cold Ischemia (hrs) | -0.09982 | 0.033 | 0.003 | 0.9050 | -0.10165 | 0.05 | -1.87 | 0.06 | -0.208 | 0.005 |
| $\beta_8$ Cold Ischemia Squared | 0.00144 | 0.0005 | 0.005 | 1.0014 | 0.00146 | 0.001 | 1.27 | 0.20 | -0.0008 | 0.004 |

Likelihood Ratio Chi-Square$_{(8)}$ = 25.20, p = 0.001, AIC = -79.07

$^a$ Interpretation: For Warm Ischemia the odds ratio is obtained from the regression coefficient as $e^{\beta} = e^{-0.03423} = 0.966$. The odds ratio indicates that each one-hour increase in warm ischemia reduces the average percentage of viable CD34+ cells to 96.6% of its previous value.

FIG. 24

| Predictor | Linear Regression Model | | | Leave-One-Out Bootstrap Cross-Validation | | | | | |
|---|---|---|---|---|---|---|---|---|---|
| | Coefficient | Standard Error | p | Coefficient | Standard Error | Z | p | 95% C.I. | |
| $\beta_0$ Constant | 160.6034 | 272.50 | 0.56 | 146.9639 | 242.57 | 0.61 | 0.54 | -328.46 | 622.39 |
| $\beta_1$ Experience | 2.60499 | 7.54 | 0.73 | 2.89051 | 5.84 | 0.49 | 0.62 | -8.36 | 14.34 |
| $\beta_2$ Facility × Experience | 5.36988 | 6.46 | 0.41 | 4.84149 | 5.55 | 0.87 | 0.38 | -6.03 | 15.72 |
| $\beta_3$ Bone Type (VB=1) | 206.9969 | 90.04 | 0.025 | 188.5609 | 86.93 | 2.17 | 0.03 | 18.18 | 358.94 |
| $\beta_4$ Warm Ischemia (hrs) | -3.73481 | 19.28 | 0.85 | -0.74672 | 28.98 | -0.03 | 0.98 | -57.54 | 56.05 |
| $\beta_5$ Body Cooling (hrs) | -82.49506 | 18.92 | 0.00005 | -81.81929 | 20.37 | -4.02 | <0.0001 | -121.74 | -41.89 |
| $\beta_6$ Body Cooling Squared | 2.95994 | 0.92 | 0.002 | 2.95785 | 0.97 | 3.06 | 0.002 | 1.06 | 4.85 |
| $\beta_7$ Cold Ischemia (hrs) | 9.55975 | 12.53 | 0.45 | 10.27826 | 14.74 | 0.70 | 0.49 | -18.61 | 39.17 |
| $\beta_8$ Cold Ischemia Squared | -0.12535 | 0.18 | 0.48 | -0.12796 | 0.25 | -0.50 | 0.61 | -0.63 | 0.37 |

Model $F_{(8,38)}$ = 6.51, p = 0.000005, $R^2$ = 0.473, $R^2$adj = 0.40

$^a$ Interpretation: The linear regression coefficient associated with Warm Ischemia indicates that each one-hour increase in warm ischemia reduces the number of CFUs by -3.73/10$^5$ cells. At the average values of warm ischemia (2.99 hours), body cooling (7.81 hours), and cold ischemia (23.14 hours), the expected CFU yield is 93/10$^5$ cells. With body cooling and cold ischemia held constant at their averages, a one-hour increase in warm ischemia from 2.99 hours to 3.99 hours would reduce the expected CFU yield from 93/10$^5$ cells to 83.89/10$^5$ cells (i.e., 93 − 9.11 = 83.89).

FIG. 25

| Predictor | Linear Regression Model | | | Leave-One-Out Bootstrap Cross-Validation | | | | | |
|---|---|---|---|---|---|---|---|---|---|
| | Coefficient | Standard Error | p | Coefficient | Standard Error | Z | p | 95% C.I. | |
| Constant | 88.3589 | 27.92 | 0.002 | 89.92144 | 28.05 | 3.17 | 0.002 | 33.95 | 143.89 |
| Bone Type (VB=1) | 16.71592 | 14.00 | 0.24 | 16.68794 | 12.58 | 1.33 | 0.18 | -7.97 | 41.35 |
| Warm Ischemia (hrs) | -7.19329 | 3.24 | 0.03 | -7.26995 | 2.70 | -2.69 | 0.007 | -12.57 | -1.97 |
| Body Cooling (hrs) | -5.24410 | 1.16 | 0.00003 | -5.28080 | 1.17 | -4.52 | <0.0001 | -7.57 | -2.99 |
| Cold Ischemia (hrs) | 0.10750 | 0.61 | 0.86 | 0.09875 | 0.53 | 0.18 | 0.85 | -0.95 | 1.15 |

Model $F_{(4,42)}$ = 7.77, p < 0.00001, $R^2$ = 0.338, $R^2$adj = 0.294

FIG. 26

|  | Beta Regression Model | | | | Leave-One-Out Bootstrap Cross-Validation | | | | | |
|---|---|---|---|---|---|---|---|---|---|---|
| Predictor | Coefficient | Standard Error | p | Odds Ratio | Coefficient | Standard Error | Z | p | 95% C.I. | |
| $\beta_0$ Constant | 3.5001 | 0.59 | <0.0001 | | 3.5455 | 0.72 | 4.94 | <0.0001 | 2.14 | 4.95 |
| $\beta_1$ Warm Ischemia (hrs)* | -0.01996 | 0.05 | 0.71 | 0.9802 | -0.02085 | 0.06 | -0.37 | 0.709 | -0.130 | 0.089 |
| $\beta_2$ Body Cooling (hrs) | -0.18145 | 0.05 | 0.001 | 0.8341 | -0.18498 | 0.06 | -3.21 | 0.001 | -0.298 | -0.072 |
| $\beta_3$ Body Cooling Squared | 0.00664 | 0.003 | 0.01 | 1.0007 | 0.00680 | 0.003 | 2.26 | 0.02 | 0.0009 | 0.013 |
| $\beta_4$ Cold Ischemia (hrs) | -0.11148 | 0.03 | 0.001 | 0.8945 | -0.11431 | 0.05 | -2.37 | 0.02 | -0.213 | -0.016 |
| $\beta_5$ Cold Ischemia Squared | 0.00148 | 0.0005 | 0.004 | 1.0015 | 0.00106 | 0.001 | 1.44 | 0.15 | 0.0008 | 0.0036 |

Likelihood Ratio Chi-Square$_{(5)}$ = 20.81, p = 0.0009, AIC = -80.68

*Interpretation: For Warm Ischemia, the odds ratio is obtained from the regression coefficient as $e^\beta = e^{-0.019} = 0.98$. The odds ratio indicates that each one-hour increase in warm ischemia reduces the average percentage of viable CD34+ cells by 2% to 98% of its previous value. For example, with body cooling and cold ischemia held constant, a one-hour increase in warm ischemia would reduce the percentage of viable CD34+ cells by ~1.3%, from an expected value of 67.6% to 66.3% (i.e., 0.98 × 67.6% = 66.3%). Odds ratios for the other predictors are obtained in the same way and have the same interpretation.

FIG 27

|  | Linear Regression Model | | | Leave-One-Out Bootstrap Cross-Validation | | | | | |
|---|---|---|---|---|---|---|---|---|---|
| Predictor | Coefficient | Standard Error | p | Coefficient | Standard Error | Z | p | 95% C.I. | |
| $\beta_0$ Constant | 756.5084 | 169.20 | <0.0001 | 713.8019 | 150.49 | 4.74 | <0.0001 | 418.845 | 1008.758 |
| $\beta_1$ Warm Ischemia (hrs) | -9.10826 | 19.98 | 0.65 | -3.67879 | 30.92 | -0.12 | 0.90 | -64.278 | 56.921 |
| $\beta_2$ Body Cooling (hrs) | -93.03639 | 20.02 | <0.0001 | -92.98267 | 23.58 | -3.94 | <0.0001 | -139.204 | -46.761 |
| $\beta_3$ Body Cooling Squared | 3.45603 | 0.98 | 0.0008 | 3.39958 | 1.12 | 3.04 | 0.002 | 1.210 | 5.589 |
| $\beta_4$ Cold Ischemia (hrs) | -4.53349 | 3.99 | 0.26 | -3.81438 | 3.82 | -1.00 | 0.32 | -11.306 | 3.678 |

Model $F_{(4, 62)}$ = 8.28, p = 0.00002, $R^2$ = 0.348, $R^2_{adj}$ = 0.306

*Interpretation: The linear regression coefficient associated with Warm Ischemia indicates that each one-hour increase in warm ischemia reduces the total number of CFUs by -9.11/10$^5$ cells. With body cooling and cold ischemia held constant, a one-hour increase in warm ischemia from would reduce the expected CFU-TOTAL count from 93/10$^5$ to 83.89/10$^5$ (i.e., 93 - 9.11 = 83.89).

FIG. 28

|  | Linear Regression Model | | | Leave-One-Out Bootstrap Cross-Validation | | | | | |
|---|---|---|---|---|---|---|---|---|---|
| Predictor | Coefficient | Standard Error | p | Coefficient | Standard Error | Z | p | 95% C.I. | |
| $\beta_0$ Constant | 104.1805 | 24.66 | <0.00001 | 104.2596 | 26.40 | 3.96 | <0.0001 | -1.027 | 1.181 |
| $\beta_1$ Warm Ischemia (hrs) | -8.11293 | 3.16 | 0.01 | -8.10758 | 2.73 | -2.97 | 0.003 | -13.466 | -2.759 |
| $\beta_2$ Body Cooling (hrs) | -5.52927 | 1.14 | <0.00001 | -5.54669 | 1.17 | -4.74 | <0.0001 | -7.837 | -2.260 |
| $\beta_3$ Cold Ischemia (hrs) | 0.08872 | 0.61 | 0.88 | 0.08278 | 0.56 | 0.14 | 0.89 | -1.027 | 1.180 |

Model $F_{(3, 62)}$ = 9.82, p = 0.00002, $R^2$ = 0.322, $R^2_{adj}$ = 0.289

FIG. 29

SYSTEM AND METHOD FOR EXTRACTION AND CRYOPRESERVATION OF BONE MARROW

CROSS-REFERENCE TO RELATED APPLICATIONS

This application is a continuation application of U.S. Ser. No. 16/734,713, filed Jan. 6, 2020, which claims the benefit of U.S. Provisional Application No. 62/938,480, filed Nov. 21, 2019, and U.S. Provisional Application No. 62/834,087, filed Apr. 15, 2019, each of which is incorporated herein by reference in its entirety.

STATEMENT AS TO FEDERALLY SPONSORED RESEARCH

This invention was made with government support under AI138334, AI129444, and HL142418 awarded by the National Institutes of Health. The government has certain rights in the invention.

BACKGROUND

Bone marrow for clinical purposes is currently harvested from HLA matched siblings or optimally matched unrelated donors. Other graft sources are also now utilized including mismatched haploidentical related or unrelated donors and umbilical cord blood (CB). When transplanted into patients with certain diseases, the hematopoietic stem cells (HSCs) in the donor bone marrow engraft in the patient and reconstitute immune and hematopoietic systems.

Bone marrow is also a good source for mesenchymal stromal/stem cells (MSCs) which are self-renewing, multipotent progenitor cells with multilineage potential to differentiate into cell types of mesodermal origin, such as adipocytes, osteocytes, and chondrocytes. In addition, MSCs can migrate to sites of inflammation and exert potent immunosuppressive and anti-inflammatory effects through interactions between lymphocytes associated with both the innate and adaptive immune system.

Currently bone marrow is typically collected through a hole created in the cortical bone with a trocar needle and then using a bone marrow aspiration needle and a syringe to draw the marrow into the syringe. Multiple syringes are usually necessary to extract all of the marrow from the bone. The syringes are then removed from the sterile field and each syringe is connected to a collection bag containing anticoagulants and the marrow is pushed into the bag. This step is repeated many times, typically in both pelvic bones, and can result in contamination of the aspirate.

It was recognized sixty years ago that banked whole bone marrow (BM) from deceased donors are also a very viable source of HSCs. Recovery of highly functional BM from deceased organ donors is conceptually similar to procurement of organs and tissues that has occurred for decades, leading to more than 30,000 organ transplants and 1 million tissue transplants performed each year in the US alone. Bone marrow HSC are hardier than sensitive organs and most tissues, as these cells naturally have evolved to reside in a hypoxic environment within the BM niche and, thus, are able to withstand prolonged periods of ischemia. HSCs are typically in a quiescent (G0) state, and therefore require little metabolic substrates and produce little waste. The CD34+ HSC and progenitors within deceased organ donor BM have been found to be highly viable. Published values for viability of CD34+ cells isolated from organ donor BM (even with non-optimized and non-validated recovery and processing procedures) was 95.2%, compared to 93.5% for living donor BM. Deceased organ donors are a rich source of viable BM cells and are statistically indistinguishable from living donors by CD34+ viability and total nucleated cells (TNC). Higher yields of CD34+ HSC and larger quantities of BM from organ donors allows banking of multiple BM units (>2 units at ~$2\times10^6$ CD34+ cells/kg, based on a 70 kg patient) for transplanting to multiple recipients as well as enabling certainty of being able to re-transplant in cases of primary graft failure.

Nevertheless, multiple barriers have prevented mainstream use of cadaveric bone marrow. One significant barrier has been in finding a streamlined process for controlled extraction and preservation of deceased donor bone marrow and the cell yields from that bone marrow. Current best-practice BM recovery from cadaveric organ donors involves multiple manual steps requiring several skilled operators. Typically, vertebral bodies (VB) are recovered by the transplant surgeon and initially cleaned in the OR prior to transport to the processing lab, where they are cleaned again very carefully to remove all remnants of tough connective tissue prior to further processing steps. Next the VBs are processed in groups of 3 by first manually cutting the bone into cubes and then feeding the cubes into a bone grinding system. The ground bone is then tumbled and rinsed multiple times, and cells are finally concentrated through centrifugation. Because no more than 3 VBs can be processed at one time, this procedure must be repeated three times per donor. This entirely manual current process typically requires 40 hours of total labor with almost 11 hours of processing time, at a typical cost of over $10,000 per donor.

Another concern regarding the use of cadaveric bone relates to the cryopreservation, banking and recovery of the bone. In particular, the concern relates to the quality of viable cells, such as HSCs, which can be obtained from donor bone, particularly for bones recovered at geographically dispersed locations and shipped long distances to a cryo-banking facility. Every step of the process for recovering bone from a deceased donor involves ischemia, or a shortage of oxygen to the cells in the bone marrow. It is known that variations in warm and cold ischemia time can influence the quality of HSCs and progenitor cells derived from cadaveric bone. Current tissue-banking guidelines in the US allow tissues to be recovered from deceased donors up to 24 hours following asystole, provided the body is refrigerated within 12 hours of cardiac arrest. However, body cooling is a variable that has not been investigated systematically in relation to the recovery of bone marrow. There is a need for a method for determining tolerance limits for both warm and cold ischemia which, if exceeded, would likely render the quality and functionality of recovered cells unacceptable for therapeutic use.

SUMMARY OF THE INVENTION

The systems and methods disclosed herein provide a needed complement to existing bone marrow and stem cell sources. Typically, less than one-half of the patients waiting for an allo-BM transplant receive the transplant. The living donor BM registry, BM cryopreservation and autotransplantation, and umbilical cord blood banking have provided lifesaving solutions for thousands of patients with hematologic diseases; however, these methods still suffer from severe limitations tied to supply and logistics and would benefit from this valuable complement. Additionally, though rare, adverse events are possible from living bone marrow donation (i.e. the risk of death associated with bone marrow donation is 1:10,000)), and while peripheral blood stem cell donation is currently much more utilized, nearly all of those donors will experience bone pain, 1 in 4 will have significant headache, nausea, or citrate toxicity, and ⅕,₀₀₀ will experience splenic rupture or other fatal complication. Additionally, the long term effects of stem cell mobilizing agents are not yet known. The technical feasibility of cadaveric BM banking and donation has been demonstrated in principle, yet these vast alternative supplies are currently discarded due to issues directly addressed by this invention.

Banking BM as disclosed herein provides a ready mechanism to match many patients who cannot find a living donor. It can greatly increase post-transplant survival rates for many patients with rapidly progressing diseases and poor prognosis by allowing on-demand transplantation and reducing waiting times for these patients from many months to only 1-2 days. And importantly, this approach provides large quantities of BM from each donor, sufficient to allow engraftment of hematopoietic stem and progenitor cells (HSPCs) for several patients and enabling immediate repeat BM transplantation when needed.

The methods and systems disclosed herein enable large supplies of on-demand bone marrow for national emergency preparedness efforts. The urgent unmet need for on-demand bone marrow and stem cell transplants as a medical countermeasure for nuclear accidents or attacks has been well documented by HHS, BARDA's multi-billion dollar Project Bioshield, and the Dept. of Defense. The present disclosure also provides needed bone marrow for emerging applications such as immune tolerance induction and beyond. A protocol for processing and the actual banking of BM from organ donors for extended periods of time is critical to this approach. Additionally, patients who receive deceased donor organ transplants today could benefit from this therapy when it becomes available in the future, if BM from these donors is banked—making this method immediately beneficial to vital organ transplant recipients. If successful, other promising methods and treatments being researched have the potential to greatly enhance the value of cadaveric BM procurement and banking using the proposed method, including HLA Mismatched Unrelated Donor (mMUD) BM transplantation—making large supplies of banked bone marrow immediately usable for most recipients who need a BM transplant quickly, particularly to address severe forms of autoimmune disorders, genetic diseases, Multiple Sclerosis, and Type 1 Diabetes.

In one aspect, a method is provided for obtaining bone marrow cells from deceased donor bone that comprises the steps of: obtaining a bone from a deceased donor; cleaning the bone of soft tissue; grinding the bone into bone pieces; filtering and rinsing the ground bone to produce a liquid composition; centrifuging the liquid composition of the filtered and rinsed ground bone to concentrate bone marrow cells; and extracting the bone marrow cells into a sterile container for cryopreservation and subsequent isolation of target cells.

In a further aspect, a bone cutting tool is provided for use in preparing the bone for grinding in the method described above. The bone cutting tool comprises two handles, a knife element and a ratchet and pawl mechanism for driving the knife element into the bone in which the components are connected to each other by elongated pins passing through openings in the respective components. The pins are removably retained by at least one removable retaining ring such that the bone cutting tool can be readily disassembled for cleaning and re-assembled after cleaning. The bone cutting tool is formed of medical grade stainless steel with the surfaces passivated to endure the sterilization environment.

In another aspect, a method is provided for recovering cells from deceased donor bone marrow that comprises the steps of: obtaining bone from a deceased donor; processing the bone to extract bone marrow cells from the bone; obtaining a reduced density FICOLL® solution having a density of 1.063-1.052 gm/mL; introducing the reduced density FICOLL® solution into a centrifuge tube to form a FICOLL® gradient; layering the extracted bone marrow cells over the FICOLL® gradient in the centrifuge tube; centrifuging the tubes containing the FICOLL® gradient and bone marrow cells; harvesting the buffy coat cells from within the centrifuge tubes; and washing the harvested cells for subsequent use or processing.

BRIEF DESCRIPTION OF THE DRAWINGS

FIGS. 12A-12C are tables of CD34+ cell viability as a function of warm and cold ischemia times, without and without body cooling.

FIGS. 13A-13C are tables of CFU-Total as a function of warm and cold ischemia times, with and without body cooling.

FIGS. 14A-14C are tables of CFU-Total as a function of warm and cold ischemia times, with and without body cooling.

FIG. 16A to FIG. 16D show processing of a typical vertebral column to isolate vBA-MSC.

FIG. 24 is a table showing a % CD34+ Beta Regression Model. The model shows the effects of warm ischemia, body cooling and cold ischemia, on the percentage of viable CD34+ cells, controlling for the influence of other covariates.

FIG. 25 is a table showing CFU-Total Linear Regression: Effects of warm ischemia, body cooling and cold ischemia on number of CFUs/$10^5$ TNC controlling for the influences of facility, experience (number of cases processed) and bone type.

FIG. 26 is a table showing CFU-GM Linear Regression: Effects of warm ischemia, body cooling and cold ischemia on number of CFUs/$10^5$ TNC controlling for the influence of bone type.

FIG. 27 is a table showing % CD34+ Beta Regression: Effects of warm ischemia, body cooling and cold ischemia on number of viable CD34+ cells as a percentage of total CD34+.

FIG. 28 is a table showing CFU-Total Linear Regression: Effects of warm ischemia, body cooling and cold ischemia on number of CFUs per $10^5$ cells.

FIG. 29 is a table showing CFU-GM Linear Regression: Effects of warm ischemia, body cooling and cold ischemia on number of CFUs per $10^5$ GM cells.

DETAILED DESCRIPTION

Figure 1C:
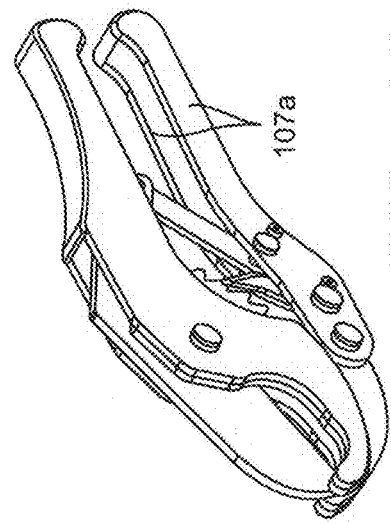
FIGS. 1A-ID are views of a hand-operated bone cutting tool according to one aspect of the present disclosure.
Figure 1A:
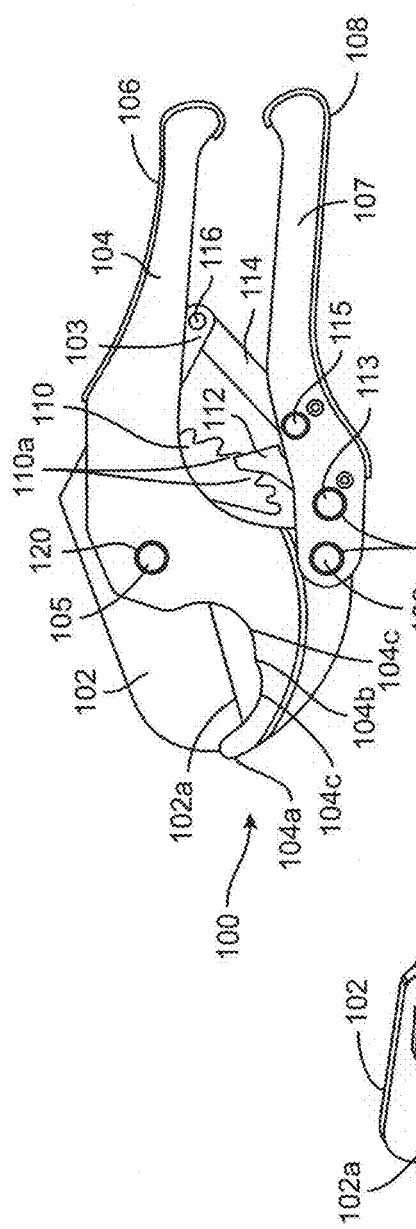

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

The present disclosure provides a clinically oriented research protocol and system that is modified to be implemented in an industrial context within state-of-the-art clean rooms. One aspect of the disclosed system involves, among other things, debridement of the incoming donor bone, initial fragmentation using a custom-made surgical stainless steel cutter, and grinding of the fragmented bone to ~3 mm fragments sizes. These refinements provide a system in which skilled tissue processing technicians can process sets of donor bones within a 6-hour window to yield meaningful quantities of viable marrow.

A first step in the process described herein is the evaluation of potential sources of deceased donor bone marrow. In processing long bones from a donor, such as the tibia, it has been found that due to conversion of red marrow to yellow with age, red marrow is limited to the ends of the long bones and varies dramatically from donor to donor. It has also been determined that mixed yellow-red marrow is poor quality, compared to wholly red marrow, such as marrow from the vertebral bodies or the ilium, and mixed yellow-red marrow contains fatty infiltrate that complicates subsequent processing steps. The best donor long bone in certain clinical experiments yielded only $\frac{1}{100}^{th}$ BM cells/kg compared to cells obtained from the ilia of the same donor. It has been determined, then, that long bone processing is preferably only performed in special cases, such as involving extra valuable "universal" HLA types or bone marrow with the HIV resistant delta 32 mutation.

In contrast, the vertebral body and the ilium represent the largest consistent reservoirs of high quality red marrow. Utilizing both sources has optimized the recovery of bone marrow, particularly with the implementation of the industrialized, scalable, GMP process disclosed herein. The completion of the process disclosed herein results in cryopreservation of a final product configuration of storing a 60-70 ml volume at a target of 100-150 million TNC/ml in standard blood bags, similar to the product configuration already used for cryopreserved BM for autologous transplants.

Preparing the Donor Bone

For the purposes of illustration, the donor bone is assumed to be vertebral bodies. However, it is understood that the methods described herein can be used on the ilium, a combination of the vertebral bodies and ilium, or other bones suitable for extraction of bone marrow and cells from the marrow, even donor bones with lower expected yields.

It is understood that the donor bones can be procured according to fixed protocols for clinical recovery. Bones can be recovered by surgeons or by personnel at a trained OPO (organ procurement organization) using an osteotome and mallet from consented organ and tissue donors. Unprocessed bones are preferably wrapped in sponges and towels soaked in saline to ensure moisture retention during hypothermic shipment on wet ice at a temperature of 0 to 10° F. to a processing facility.

The process for preparing the donor bone can occur soon after the bone is obtained from the deceased donor or can occur after the donor bone has been shipped in a hypothermic environment to a processing facility. Since the donor bone can experience prolonged periods of ischemia during recovery and shipment to the processing facility, care must be taken to track the length and type of ischemia—i.e., warm ischemia and cold ischemia. As described in more detail herein, bone subject to predetermined periods of warm and/or cold ischemia are suitable for obtaining meaningful quantities of viable bone marrow cells.

In the first step of processing the donor bone, the bone is debrided in an ISO-5 (class 100) environment (biosafety cabinet) with an ISO-7 (class 10,000) background (clean room), with special care taken to sterilize the bag containing the donor bone, such as by spraying with 70% isopropanol. In one embodiment, the debridement is conducted manually using scalpels, osteotomes and gouges. In processing vertebrae, typically a spinal segment including multiple vertebral levels will be provided. In a typical case, the spine segment runs from T8 to L5, for ten vertebral bodies. During initial debridement of the spinal segment, when enough soft tissue has been removed to visualize the pedicles, the pedicles are removed using either a tissue processing band saw or a bone saw, such as the Stryker System 6 Saw (Stryker, Kalamazoo, Mich.). Special care is taken to avoid breaching the cortical bone which would expose the cancellous bone, to ensure that the hypoxic cancellous bone marrow remains protected throughout the entire debriding process. The anterior elements of the vertebral bodies remain, while the pedicles and posterior elements are discarded.

Using a boning knife or tissue processing band saw, the vertebral bodies are separated at the intervertebral discs. The intervertebral disc and soft tissue remaining on each vertebral body is removed with a scalpel, scissors and/or osteotomes, leaving clean, separated VBs. In the case of donor ilium, the soft tissue can be removed with gouges and a scalpel, with special care again taken to ensure that the cortical bone is not breached. Any anatomical pathologies or injuries of the bone are noted and recorded as part of the batch record for the marrow ultimately obtained from the bones. Bones damaged during the recovery process are discarded.

The VBs are placed into a sterile bag and submerged in a 10% bleach solution, yielding a concentration of 5,000 ppm free chlorine, for a predetermined period, typically 10-25 minutes. Bleach has a broad spectrum of anti-microbial activity, does not leave a toxic residue, is unaffected by water hardness and is fast acting. At the end of the period, the bones are transferred to another sterile bag and submerged in a 3% hydrogen peroxide ($H_2O_2$) solution. The bag is closed and shaken briefly to ensure that the entire surface of the bone is in contact with the solution. Most living cells include catalase, which is an enzyme that catalyzes the breakdown of $H_2O_2$ into $H_2O$ and $O_2$. This breakdown manifests as foam or froth when the $H_2O_2$ solution contacts soft tissue but not bone. The foam level can be observed as an indication of the amount of soft tissue remaining on the bone. This observation can be performed manually by a human processor or, in another embodiment, by an automated processor. The automated processor incorporates a visualization device, such as a camera, and object recognition software that can determine foam levels within the bag. The addition of an inert contrast dye can help the human or automated processor detect the foam level. If any foam or froth is observed, the bone is returned for further processing to remove all of the remaining soft tissue from the bone. Once the VBs or ilium has been cleaned of all soft tissue, the bones are transferred to a new sterile bag. The bag is filled with 1 L of PLASMA-LYTE™ (multiple electrolytes injection obtained from Baxter Healthcare, Ltd.), or other suitable sterile, nonpyrogenic isotonic solution. The bag is closed and shaken briefly to ensure that the entire bone is contacted with the PLASMA-LYTE™

Extracting the Bone Marrow

Figure 1B:
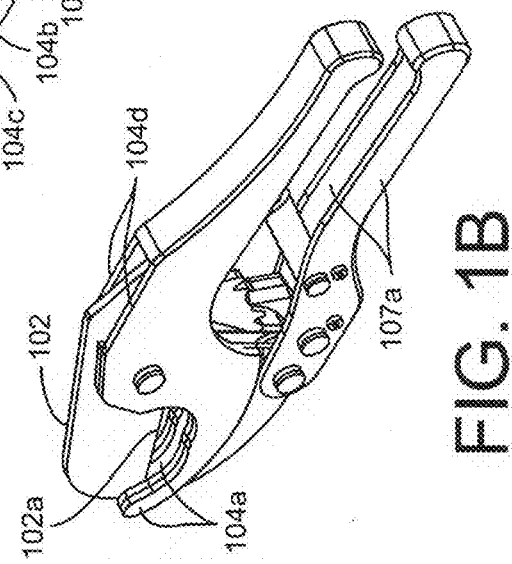
Figure 1D:
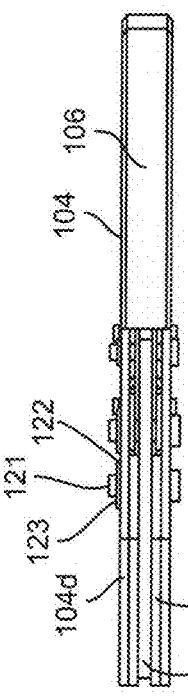

The bone is removed from the bag and from the PLASMA-LYTE™, and a sterile gauze or sponge is used to absorb any liquid remaining on the VBs. In one approach, a saw and/or anvil shears are used to cut the VBs are cut into smaller pieces, such as 1.5 cm² pieces, that are small enough for fragmenting with a bone grinder. In order to simplify the process and for increased safety to the processing personnel, a custom bone cutting tool 100 is provided as illustrated in FIGS. 1A-1D that is used to cut the VBs into the smaller pieces. The bone cutting tool 100 includes a knife element 102 with a knife edge 102a configured to penetrate and sever bone. The knife element 102 is pivotably connected at a pivot 105 to a fixed handle component 104. The fixed handle component 104 includes a jaw end 104a that is juxtaposed with the knife edge 102a to cut through a bone retained in the jaw end. As shown in FIG. 1B, the fixed handle component includes two plates 104d that are spaced apart to receive the knife component therebetween, as best seen in FIGS. 1B-1D. In particular, the knife edge 102a passes between the two plates 104d at the jaw end 104a, which ensures that the knife edge 102a passes through the bone captured by the jaw end 104a. The jaw end 104a can include two recesses 104c separated by a ridge 104b that engages the bone and helps hold the bone in the jaw end as the knife edge 102a passes through the bone. Alternatively, a single recess can be defined in the jaw end configured to retain the bone. The pivot 105 is in the form of a pin that extends through the two plates 104d and the knife component 102 sandwiched between the plates.

The bone cutting tool 100 includes a lever handle 107 that is pivotably mounted to the fixed handle 104 at a pivot 109. The pivot can include a biasing element, such as a torsion spring (not shown) configured to bias the lever handle 107 away from the fixed handle 104. The lever handle is thus configured to be pivoted toward the fixed handle when the two handles are grasped and squeezed by the user, and then to pivot away from the fixed handle when the user releases the grip on the handles. It can be appreciated that the lever handle 107 is formed of two plates 107a with the fixed handle 104 sandwiched between the two plates 107a at the pivot 109. As with the pivot 105 the pivot 109 is in the form of a pin that extends through the two plates 107a and through the fixed handle 104. Both handles 104, 107 include respective gripping plates 106, 108 that are contoured to be grasped by the palm and fingers of the user. The gripping plates 106, 108 connected the pairs of plates 104d, 107a that form the two handles. The surfaces of the gripping plates can include a non-slip feature to facilitate grasping the tool.

The lever handle 107 includes a pawl 112 that is pivotably mounted at pivot 113 to the lever handle. As with the other pivots, the pivot 113 is a pin that extends through the pair of plates 107a that form the lever handle 107 and through an end of the pawl 112. The pivot 113 includes a biasing element, such as a torsion spring (not shown), that biases the pawl 112 toward a ratchet component 110 of the knife element 102. The end of the pawl 112 is configured to engage teeth 110a on the ratchet component 110 to rotate the ratchet component, and thus the knife element 102, in a counter-clockwise direction as viewed in FIG. 1A. In particular, as the user squeezes the two handles together, the lever handle 107 moves toward the fixed handle 104 which pushes the pawl 112 upward against a tooth 110a of the ratchet to pivot the ratchet upward and counter-clockwise. When the user releases the lever handle, the handle moves away from the fixed handle, causing the pawl 112 to slide down the ratchet in the clockwise direction until it reaches another tooth 110a. Repeated squeezing of the two handles thus cases the pawl to successively rotate the ratchet. The knife element 102 also includes an integral link 103 that is pivotably connected to a free link 114 at a pivot 116. The free link 114 is pivotably connected to the lever handle 107 at a pivot 115. The integral link 103 and free link 114 hold the knife element 102 in position as the pawl traverses the ratchet component 110. The pivot 115 of the free link is a pin, like the other pivots, and includes a biasing element, such as a torsion spring (not shown) that biases the lever handle 107 away from the fixed handle 104. This allows the user to close and release the handles of the tool to successively advance the pawl 112 along the ratchet component 110, which successively advances the knife edge 102a into the bone.

In one feature of the bone cutting tool 100 of the present disclosure, the pivots 103, 109, 113 and 115 are configured to allow complete disassembly of the tool. Complete disassembly is important to allow the tool to be fully cleaned and sterilized between uses. Thus, the pivots each include a pin and retaining ring construction, with the retaining ring holding the components together on the pin. Thus, as shown in FIG. 1D, the pin 121 can extend through walls of a component, such as the opposite walls 107a in the lever handle 107 and through a corresponding bore in the component being connected, such as the knife element 102. Retaining rings 122 can engage grooves 123 at the opposite ends of the pin 121 to hold the components together. Alternatively, one end of the pin can have an enlarged head with the retaining ring engaging the opposite end of the pin. When it is necessary to clean and sterilize the tool 100, all of the retaining rings 122 can be removed, all of the pins 121 can be removed, and the connected components separated. The knife element 102, the fixed handle 104 and the lever handle 107 are thus separated so that every surface of the components can be effectively cleaned.

The elements of the bone cutting tool 100 are formed of medical grade stainless steel. The steel is preferably hardened steel capable of withstanding the forces required to cut through bone. In the cleaning process, the tool is subjected to steam sterilization, which can be deleterious to the steel. Thus, in one feature of the present disclosure, the surfaces of the stainless-steel elements are passivated to prevent oxidation of the steel elements during sterilization.

Returning to the process steps, and particularly the step of extracting bone marrow, the pieces produced by the bone cutting tool are immediately placed into a sterile pitcher and submerged in 300-500 mL of a grind media. In one aspect of the present system and method, the grind media uses PLASMA-LYTE™-A as a base with 10 U/mL heparin, 2.5% human serum albumin (HSA), and 3 U/mL BENZONASE® reagent (a nuclease that cleaves both DNA and RNA; Merck KGAA Corporation). Heparin is used as an anticoagulant. HSA provides a protein source to prevent cell adherence and adsorption to surfaces, as well as reactive oxygen scavenging. It is noted that conventional grind media utilizes DNase™, but for the present disclosure BENZONASE® reagent is substituted for DNase™ reagent (Qiagen Sciences LLC). Whereas DNase™ works only on DNA, modern pharmaceutical biotechnology processing relies on enzymes that can cleave all forms of DNA and RNA, and can reduce the viscosity of the solution in which the cells are suspended. It is noted that IMDM (Iscove's Modified Dulbecco's Media) can substitute for the PLASMA-LYTE™-A, since IMDM is suitable for rapidly proliferating high-density cell cultures and ideal for supporting T- and B-lymphocytes. It is further noted that DENARASE® reagent (a nuclease that cleaves both DNA and RNA; C-Lecta GmbH) is equivalent to BENZONASE® reagent in the same quantity in the present process. Another pitcher of 300-500 mL of grind media is retained for collecting the bone fragments after grinding, and another supply of about 100 mL of the grind media is retained for rinsing through the grinder during the grinding process to prevent bone fragments from sticking to the surface of the pitcher of the grinding components.

An electric bone grinder or a purpose-built bone grinder, such as the grinder of Biorep Technologies Inc, (Miami, Fla.) can be used in an ISO-5 environment within an ISO-7 clean room. Bone types are kept separate if both VB and ilium from the same donor are being processed. The bone is kept submerged in grind media at all times during and after the grinding process. Once all of the donor bone pieces are ground, the chamber of the bone grinder is thoroughly rinsed with fresh processing media. The bone fragments are discharged from the grinder into the pitcher containing grind media.

The contents of the pitcher are transferred to sterile bags. In the next step the contents of the sterile bags are filtered to extract the solid components. In one embodiment, the contents of each bag are passed through a series of stainless steel sieves. In this embodiment, a No. 40 (425 µm) sieve is stacked on top of a No. 80 (177 µm) sieve, which is seated over a catch-pan to receive the liquid filter contents. The sterile bags containing the output from the grinder is swirled and then poured evenly over the sieve stack or filtration sets. The filtering process is observed to ensure that excessive clumping is not occurring, which can signal the presence of soft tissue or other contaminants. Bone fragments retained on the surface of the sieves are distributed evenly on the sieves and rinsed with 250 mL of fresh processing medium. In one embodiment, the processing medium used for rinsing is the grind media described above or PLASMA-LYTE™ with 2.5% HSA. The sieved bone marrow product, which can be approximately 1000 mL in a well-performed process, is transferred to sterile packs for subsequent processing and analysis. The contents of each bag are visually inspected to confirm that the contents do not include any visible bone fragments or soft tissue.

Figure 2:
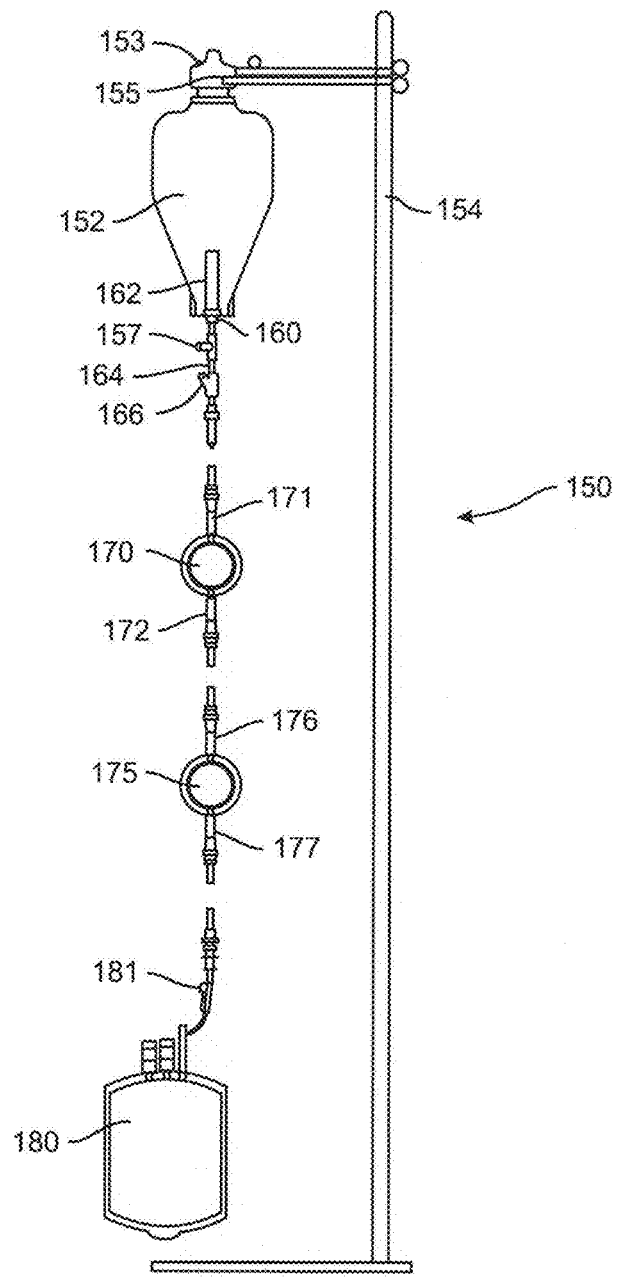
FIG. 2 is a view of a filtration system according to one feature of the present disclosure.

In another embodiment, the contents of each bag are passed through bone marrow filtration units, as depicted in FIG. 2. In this embodiment, the system 150 includes a stand 154 configured to support a sterile collection bag 152 which contains the bone fragments and media from the grinding operation described above. The stand includes a container hanger 155 configured to engage the cap 153 of the sterile bag to suspend the container. The bottom of the bag includes a discharge assembly 160 that includes a pre-filter 162 projecting into the body of the collection bag. In one specific embodiment the pre-filter 162 is an µ850 m filter. The filter 162 is connected to an output tube 164 that is connected by a container claim 166 to the input line 171 of a first in-line filter 170. In the specific embodiment, the first in-line filter is a 200 µm or a 500 µm filter. The output line 172 of the first in-line filter is connected to the input line 176 of a second in-line filter 175. The second in-line filter is a 200 µm or a 500 µm filter. The two in-line filters are initially both 500 µm for a first pass through the filter system 150. A second rinse is then performed on the grindings with the two in-line filters being 200 µm. This double-pass filtration results in a cleaner suspension and enhances removal of fat from the suspension. The second in-line filter 175 has an output line 177 that can be engaged to a sterile bag, such as bag 152 for the second filtration pass. On the second pass through the system, the output line 177 of the second in-line filter 175 can be engaged to a container clamp 181 of a transfer pack container 180. The transfer pack container can be a 600-2000 mL bag to accommodate the filtered bone marrow product, which can be approximately 1000 mL in a well-performed process.

For quality control, a small quantity of bone marrow, such as 0.3 mL, is extracted from the sterile pack 152 using a syringe at an injection site 157 and conducting inversion mixing before pulling the sample. The sample can be tested by a hematology analyzer, such as a Sysmex Hematology Analyzer, to determine the TNC (total nucleated cell) content of the sample, as an indicator of the TNC content of the bone marrow being subsequently processed.

Fat Removal and Concentration

Figure 3:
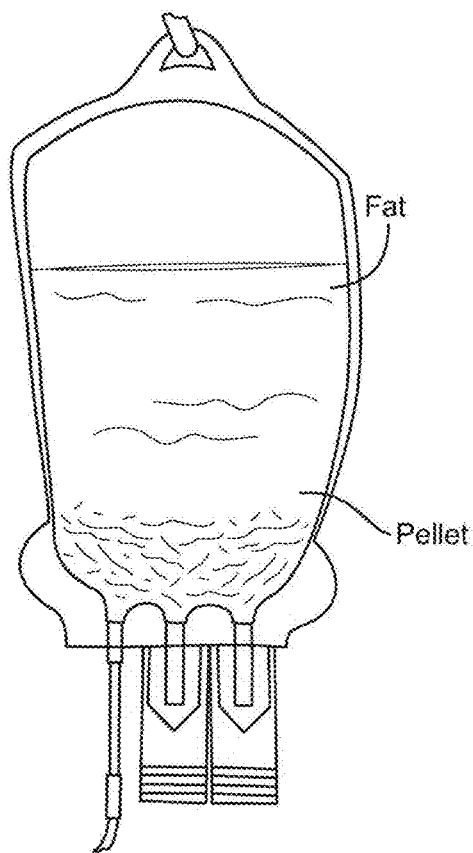
FIG. 3 is a view of a sterile bag containing a bone marrow pellet processed according to the methods of the present disclosure.
Figure 4:
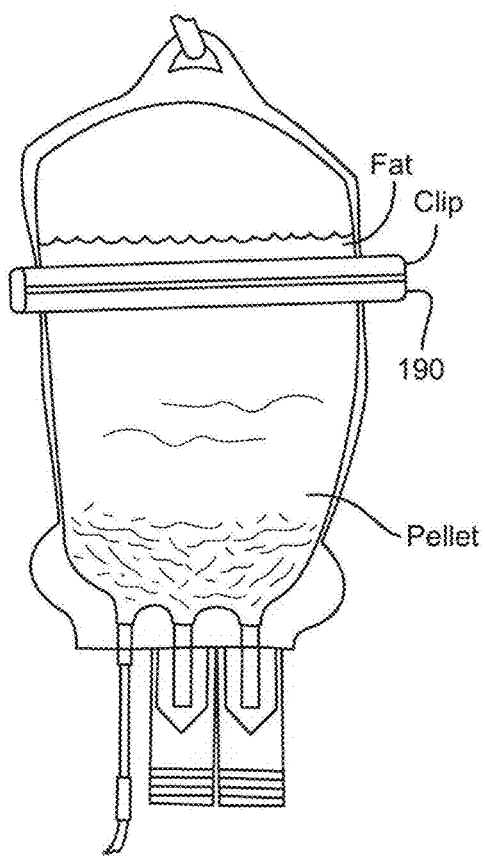
FIG. 4 is a view of the sterile bag of FIG. 3 with a clip engaging the bag to separate the fat from the bone marrow pellet.

The bone marrow product collected from the filtering step is essentially a fatty emulsion. The fat content of the suspension obtained from the sieve filtering approach disclosed above is greater than the fat content of the suspension obtained from the double-pass filtration system 150. However, in both cases, there is a need to remove the fat content from the suspension. The suspension obtained from the filtering step is recovered into 250 mL bags which are hermetically sealed with tube welders. Pairs of sterile bags and taring sticks are mounted within a centrifuge with bag ports facing down, and balanced. Volume compensating plates are used to prevent creasing of the bags during centrifugation. In one embodiment, the bags are centrifuged at 500×g for 15 minutes at room temperature to concentrate the cells, preferably to $2\text{-}3\times10^8$/ml. After centrifugation is complete, each bag is individually hung on a ring stand. The distinct layers within the bag are visible, with the fat layer clearly delineated on top of the supernatant with the bone marrow pellet at the bottom, as shown in FIG. 3. A new sterile bag is welded to the bag removed from the centrifuge. A bag clamp or clip 190 is placed on the bag just below the fat layer, as shown in FIG. 4, to clamp off or squeeze the bag closed beneath the fat layer. The pellet is then drained from the centrifuge bag into the new sterile bag, with the bag clip preventing passage of the fat layer. The pellet is agitated as it is drained to resuspend all of the pellet. After about half of the pellet has drained into the new bag, the tubing is closed with a hemostat or tube sealer. The second centrifuge bag is then welded to the new bag containing the pellet, and the contents of this second centrifuge bag are drained into the new bag.

Figure 5:
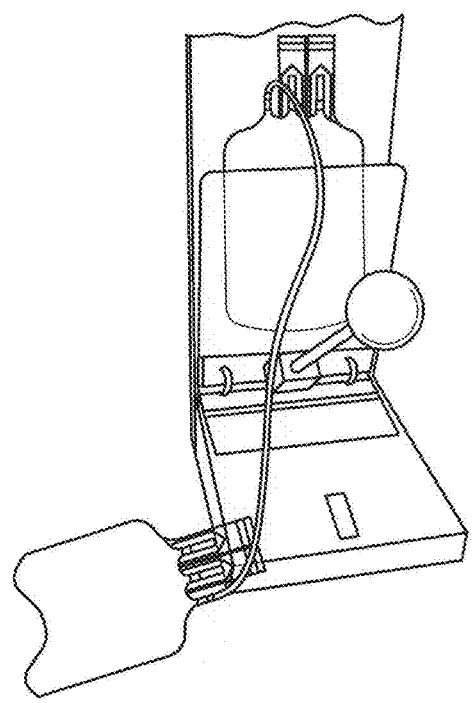
FIG. 5 shows the set-up for isolation of the bone marrow pellet

The result of this step is new sterile bags containing the bone marrow centrifuged to remove the fat. These bags of de-fatted bone marrow are then centrifuged at 500×g for 15 minutes at room temperature, with volume compensating plates to prevent creasing of the bags. Each bag is removed and suspended on a ring stand and a waste bag is welded to the bag, and a plasma extractor is used to remove the supernatant into the waste bag, as shown in FIG. 5. The tubing is clamped with a hemostat when the pellet rises or breaks. The tubing is then sealed and severed to remove the pellet-containing bag from the waste bag, which is discarded. A Luer connection is welded to the pellet-containing bag. The pellets from each bag are combined into a bulk bag using a large syringe. The pellet-containing bags are rinsed into the bulk bag using a rinse media. The bulk bag is inverted several times to ensure that all of the pellet is resuspended. A small quantity of the processed BM, such as 0.5 mL, can be removed for quality control testing for density and cell count. The test sample can also be evaluated for human leukocyte antigens, CCR5delta 32 mutation and apolipoprotein (APOE), among other things.

Cryopreservation of the Bone Marrow

It is contemplated that each bone donor can yield three or more bags of bone marrow through the process described above, based on ten vertebrae and the ilium obtained from the donor. If at the end of the process for a given donor three bags of bone marrow are not obtained, the donor can be flagged as potentially not passing overall quality control. A predetermined volume of bone marrow in each bag is contemplated, such as 70 mL contained in 250 mL bags. This predetermined volume is used to calculate the volume of freeze media components necessary for efficient cryopreservation of the bone marrow pellet. The freeze media is a solution of a rinse media and a cryopreservation composition. The cryoprotectant composition can be a permeable media, such as dimethyl sulfoxide (DMSO); 1, 2 propane diol; ethylene glycol; glycerol; foramamide; ethanediol or butane 2, 3 diol; and/or a non-permeable media, such as hydroxyethyl starch (HES), Dextran, sucrose, trehalose, lactose, raffinose, Ribotol, Mannitol or polyvinylpyrrolidone (PVP). 2.5% HSA also provides cryoprotection through oncotic pressure, cell surface protein stabilization and reactive oxygen scavenging. In a preferred embodiment, the cryopreservation media is DMSO. The rinse media can be an electrolyte medium, such as PLASMA-LYTE™, ISOLYTE®, IMDM or other electrolyte solutions suitable for infusion. The freeze media can also include concentrations of oxyrase to reduce oxygen content to less than atmospheric, such as to less than 3% of atmospheric concentrations. The addition of oxyrase produces a hypobaric composition that can facilitate cryopreservation.

Figure 6:
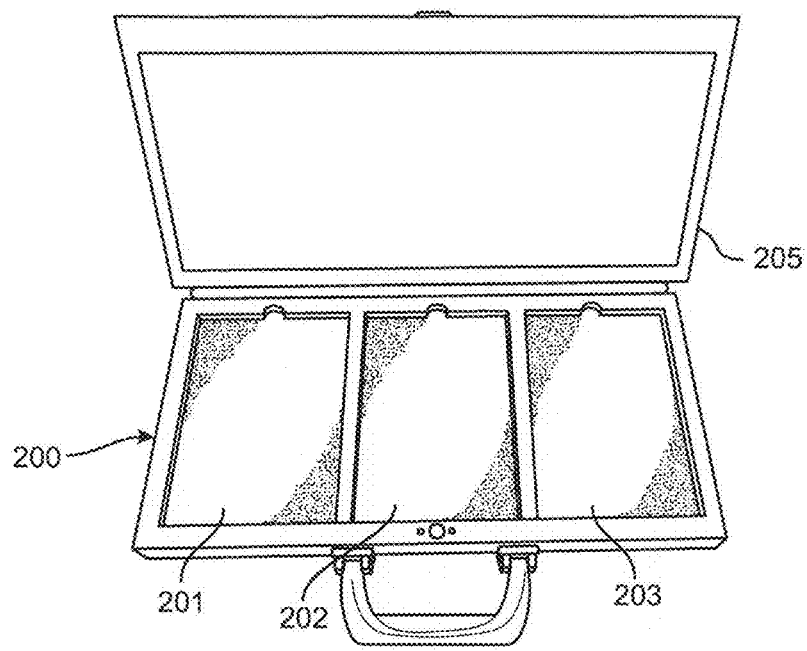
FIG. 6 is a perspective view of a cooling box according to one aspect of the present disclosure.

The freeze media is prepared by mixing the cryoprotectant and the rinse media according to the calculated total volume of freeze media needed for the volume of bone marrow collected in the prior steps. The bag containing the bone marrow is placed on a rocker for mixing and the freeze media is introduced into the bag by syringe. The freeze media is introduced at a particular rate over a predetermined time. In one embodiment, the freeze media is added at a rate of 10% of the media per minute, for a time of ten minutes. Once the media has been mixed with the concentrated bone marrow, a test sample is extracted by syringe. The remaining mixture of freeze media and bone marrow is injected in predetermined amounts into separate cryopreservation bags. In one embodiment, 70 mL of bone marrow mixture is introduced into each cryopreservation bag and air is drawn out with a syringe. At the end of the process, an 8 mL sample can be removed for sterility testing. Each cryopreservation bag is sealed to create four compartments, which are then separated for storage in cassettes to be stored in a cryofreezer. In another embodiment, the separated compartments are stored in a passive cooling box, such as cooling box 200 shown in FIG. 6.

When the test samples from the particular bone marrow batch have been validated for cell count and sterility, the bags of cryopreserved bone marrow can be further cooled for long-term storage. In one embodiment, the bags are cooled at a controlled rate to prevent damage to the bone marrow and cells. In one specific embodiment, the bags are cooled at a rate of −1 to −40° C. per minute to a temperature suitable for plunging the bags into liquid nitrogen. A suitable temperature is in the range of −40 to −100° C. Once that temperature has been reached, the bags are cooled further at a more rapid rate to a temperature of below −130° C. for storage. A cryopreservation bag is placed within a corresponding compartment 201-203 of the cooling box 200 and the overlapping cover 205 is closed over the compartments to provide a sealed environment for cryo-preservation of the contents of the bags. The cooling box is placed within a cryo freezer such that the cooling box produces a cooling rate of −0.5 to −2 C°/min, and typically of −1 C°/min, with nucleation temperatures above −20° C. The freezing process continues at the prescribed rate until the temperature of the bone marrow reaches a suitable temperature. The suitable temperature for storage of the bags is a temperature ≤−80° C. or ≤−150° C.

In another embodiment, the bags are cooled in a static chamber temperature as opposed to the controlled rate cryopreservation described above. In the passive cooling approach, the cooling box is placed in a −86° C. freezer until the bags reach a stable temperature.

It is contemplated that the cryopreservation storage can be in many forms. For instance, the cryopreserved bone marrow can be contained in bags of 1 mL to 5 mL volume or vials of 0.1 to 15 mL volumes. In a preferred embodiment, the bags with 70 mL bone marrow are stored in a cooling box within a cryogenic freezer.

The cryopreserved bone marrow is cryobanked for later thawing and extraction of desired cells. The thawed bone marrow can be provided for a wide range of treatments including treatment for leukemias, brain tumors, breast cancer, Hodgkin's disease, multiple myeloma, neuroblastoma, non-Hodgkin's lymphoma, blood cancers, ovarian cancer, sarcoma, testicular cancer, other solid organ cancer, rheumatoid arthritis, multiple sclerosis, diabetes mellitus, cystic fibrosus, Alzheimer's disease, genetic immunodeficiencies, metabolic disorders, marrow failure syndromes, and HIV. Bone marrow can also be used for induction of immunotolerance to reduce the potential rejection of an implant obtained from an organ donor. Bone marrow treatments can also be indicated for casualties caused by radiation and certain biological weapons.

Bone marrow is a well-known source for mesenchymal stromal/stem cells (MSCs) which can be harvested from previously cryo-banked organ and tissue donor bone marrow using the methods described above. MSCs are self-renewing, multipotent progenitor cells with multilineage potential to differentiate into cell types of mesodermal origin, such as adipocytes, osteocytes, and chondrocytes. In addition, MSCs can migrate to sites of inflammation and exert potent immunosuppressive and anti-inflammatory effects through interactions between lymphocytes associated with both the innate and adaptive immune system. MSCs can be used in treating osteogenesis imperfect, cartilage defects, myocardial infarction, Crohn's disease, multiple sclerosis, autoimmune disease such as Lupus, liver cirrhosis, osteo arthritis, and rheumatoid arthritis. Matched HSC/MSC units which can be used in co-transplant for treatment of graft vs. host disease (GVHD), and for hematopoietic stem cell transplant support.

Figure 7:
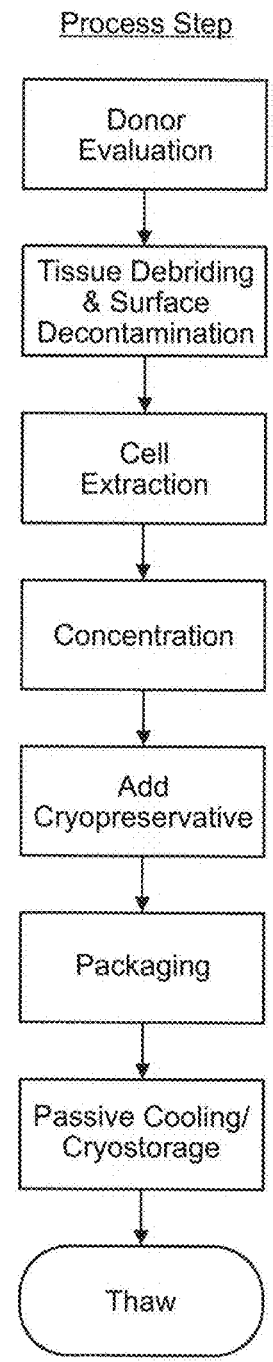
FIG. 7 is a flowchart of the steps of one method according to the present disclosure

The present method provides a system for extracting and banking bone marrow for future clinical use according to the process steps described above, as summarized in the flowchart of FIG. 7. This method can eliminate the failures of the current methods of matching bone marrow donors to groups that are tough to match, such as certain minorities. Once the bone marrow is cryopreserved and banked there is no uncertainty as to the source of the bone marrow, there is no wait for a future recipient and the bone marrow is available in large repeatable volumes.

Automated System for Recovery of Bone Marrow

Figure 8A:
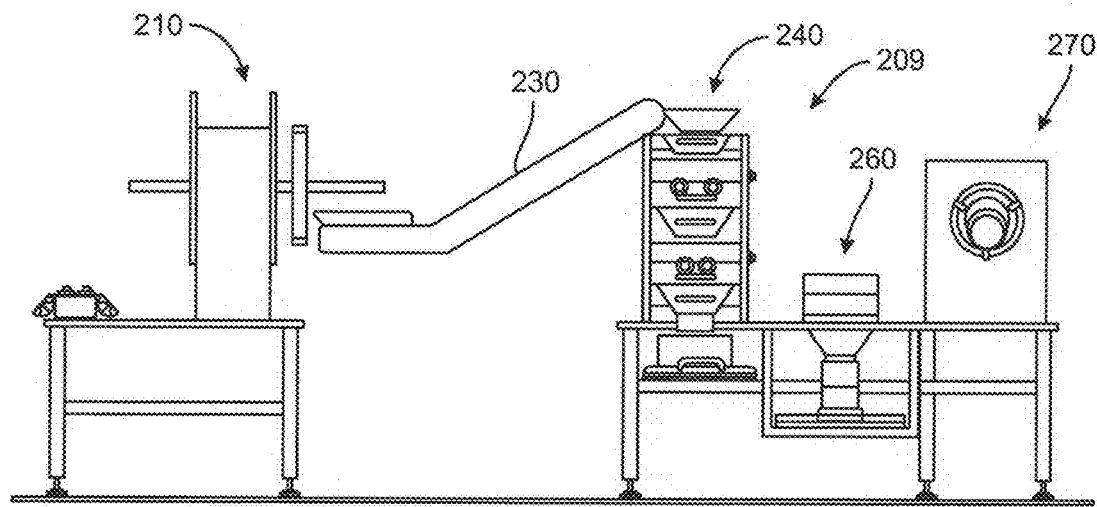
FIGS. 8A and 8B are side and perspective views of an automated bone processing system according to one aspect of the present disclosure.
Figure 8B:
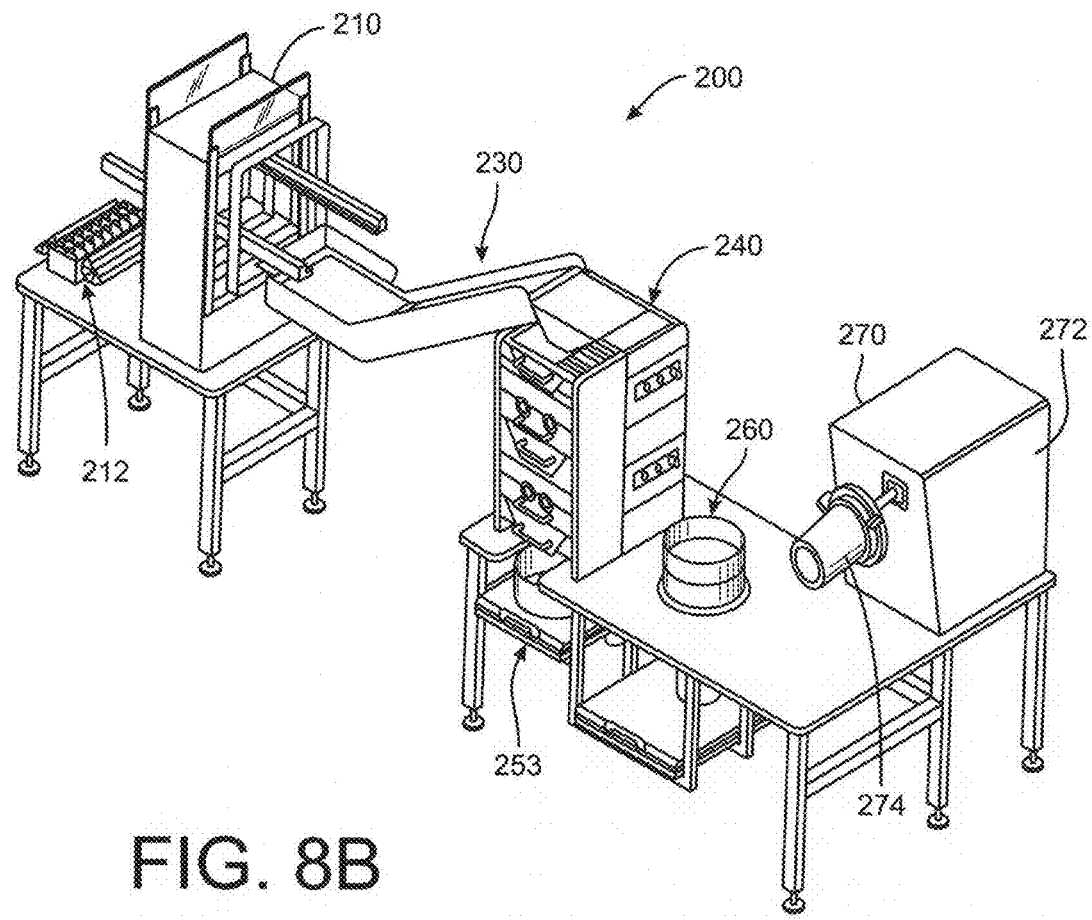
Figure 9B:
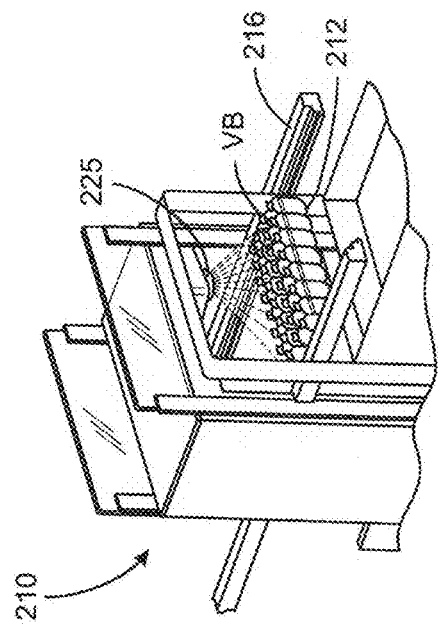
FIGS. 9A and 9B are perspective views of a bone debriding station of the system shown in FIGS. 8A-8B.
Figure 9A:
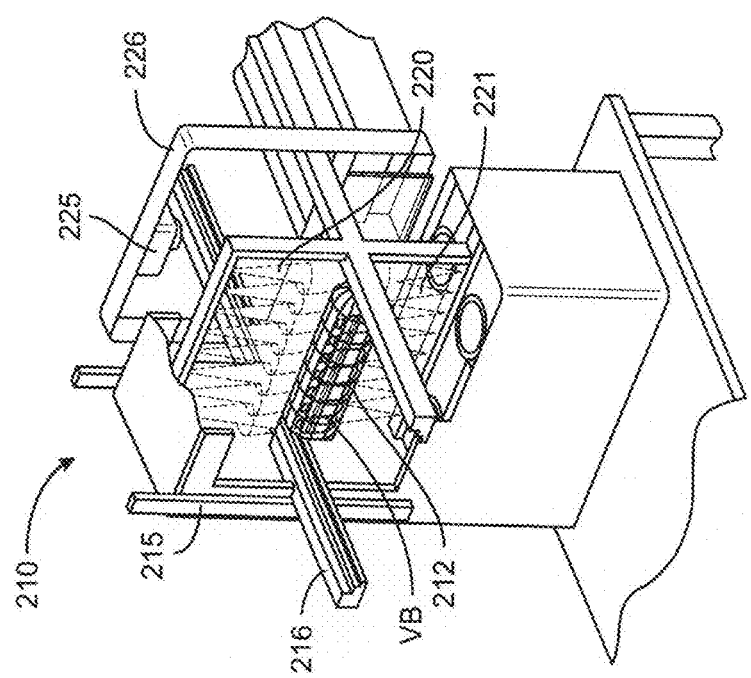

The present disclosure contemplates an automated process for recovery of the bone marrow, and even selection of cells from the bone marrow. In one aspect, an automated system 209 includes sequential stations, as depicted in FIGS. 8A-8B. The first station 210 of the automated process debrides the VBs to remove all soft tissue. In contrast to the manual process that operates on one VB at a time, the automated process is configured to debride an entire donor VB set (which can be at least ten vertebral bodies). The VBs are mounted on a rack or tray 212 that is configured to support the vertebral body set from a given donor. The tray 212 is placed on transfer rails 216 of a housing 215, as shown in FIGS. 9A-9B, with the tray advanced automatically or manually into the interior of the housing. The housing 215 supports a plurality of hydrojets 220 that direct high pressure and high velocity jets of saline onto the VBs. In the known manual process, a manual hydrojet, operating at lower velocities and pressures, directs a stream of detergent onto the VB. In the manual process, the detergent is needed to clean the VBs of the soft tissue. In contrast, the automated cleaning station 210 of the present disclosure uses a saline medium, with the velocity and pressure of the water jets being sufficient to dislodge all soft tissue from the VBs. The automated cleaning station of the present disclosure includes jets configured to produce a direct stream or narrow "V" water/saline jet that generates a high concentrated impact force at varying distances. To achieve good coverage of the VBs, the device includes many direct jets at close spacing at different orientations relative to the VBs, which allows for uniform cleaning independent of position of the VB in the device. In the illustrated embodiment of FIG. 9A, the hydrojets are provided in an upper 220 and a lower row 221. The "V" jets are aligned at different angles to achieve full coverage of the surfaces of the VBs. In addition, or alternatively, the hydrojets 220, 221 can be configured to oscillate over the tray of VBs to ensure complete coverage.

A visualization device 225 is arranged at the outlet of the debridement station 210 that is operable to visualize and interpret the VBs exiting the station to determine if all of the soft tissue has been removed, as shown in FIG. 9B. If not, then the VBs are returned along the rails 216 back into the housing for further hydrojet processing. It is contemplated that a controller (not shown) can be provided to control the movement of the tray 212 along the rails 216 and to interpret the signals generated by the visualization device 225. The visualization device can include a camera that obtains an image of the VBs and the controller can include imaging software capable of recognizing the soft tissue in the acquired image. A dye can be applied to the cleaned VBs at the end of the hydrojet debridement process, in which the dye is absorbed by soft tissue but not bone. The dye can thus provide contrast to facilitate differentiation of any remaining soft tissue from the bone. The visualization device 225 can be configured to pan across the VBs, such as by translating along a frame 226 and by translating the frame in order to view the VBs at all angles.

Figure 10B:
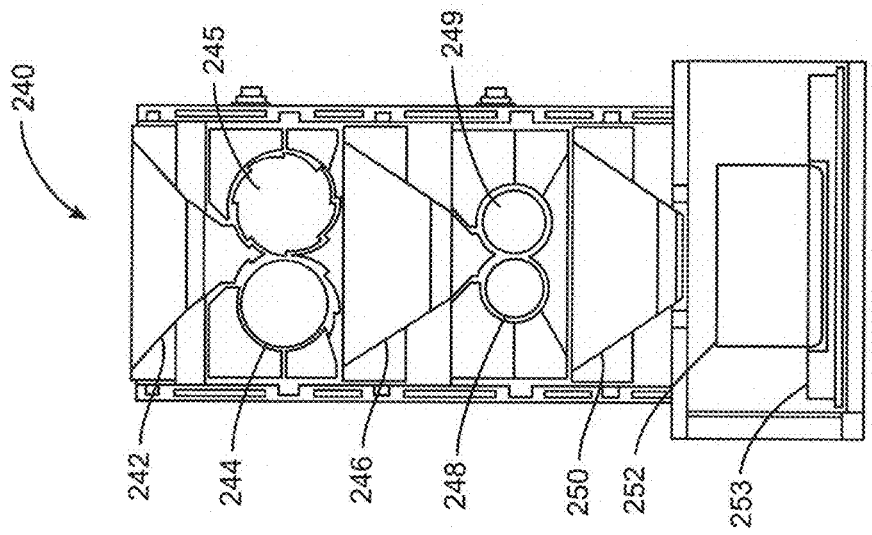
FIGS. 10A and 10B are perspective and front views of a bone grinding station of the system shown in FIGS. 8A, 8B.
Figure 10A:
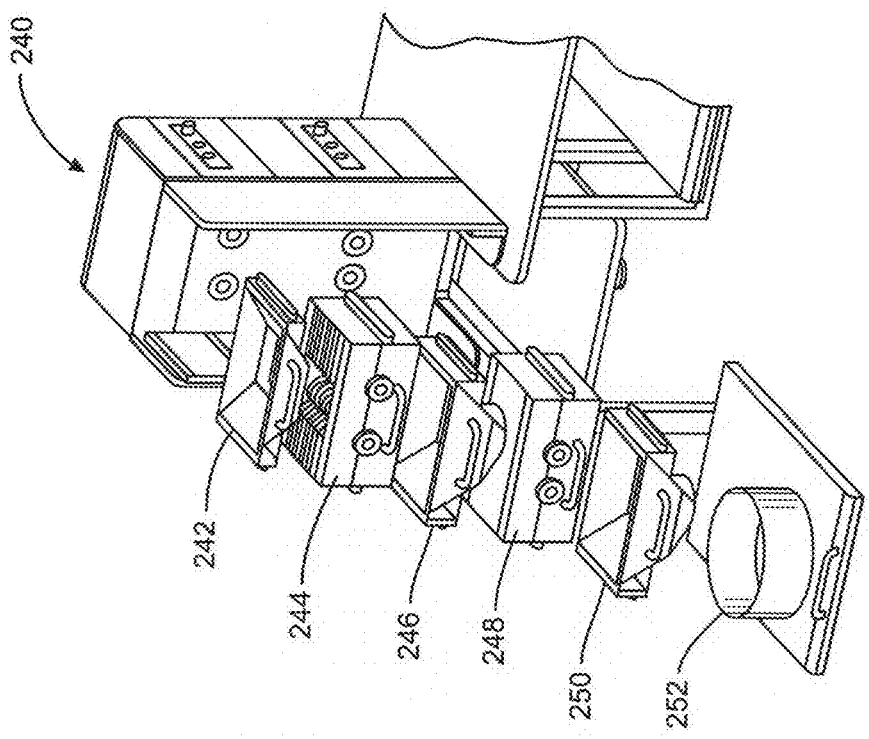

Returning to FIGS. 8A-8B, once it is determined that the VBs are cleaned of all soft tissue, the debrided VBs are then fed by a conveyor 230 to an automated grinding station 240 to produce appropriately sized pieces for tumbling and final cell extraction. The manual "cubing" process described above can be variable, time consuming, and potentially not safe for the operator. The automated system includes a grinding station that combines the steps of "cubing" the VBs (i.e., cutting the VBs into small pieces) and grinding the cubed VBs to reduce the VBs to 2-3 mm pieces. The rails 216 and tray 212 can be configured to deposit the debrided VBs onto the conveyor 230 which then automatically transfers the VBs to an input hopper 242 of the grinding station 240, shown in more detail in FIGS. 10A-10B. The VBs are directed through an initial mill cutter module 244, then through a funnel 246 to a fine mill cutter module 248, as shown in FIG. 10A. As shown in FIG. 10B the initial mill cutter module 242 includes opposed rotating grinding mills 245 that are separated by a predetermined gap, such as a 5-8 mm gap, so that the incoming VBs are ground into coarse-sized segments. The coarse ground segments are fed to the fine mill cutter module 248 in which smaller diameter grinding mills 249 are provided. The fine grind mills 249 are separated by a smaller gap, on the order of 2-3 mm, to produce finely ground VB segments. As shown in FIG. 10A, a funnel 246 conveys the coarse ground segments to the second grinding mill 248, and a funnel 250 directs the finely ground VB segments to a collection pan 252 supported on a plate 253. During the milling operation, a measured volume of processing/resuspension medium with DNAse™ can be directed through the upper hopper, onto grinding cutters. This medium can be manually introduced during the operation of the grinding station 240, or can be automatically implemented through nozzles incorporated into the hopper 242.

Figure 11:
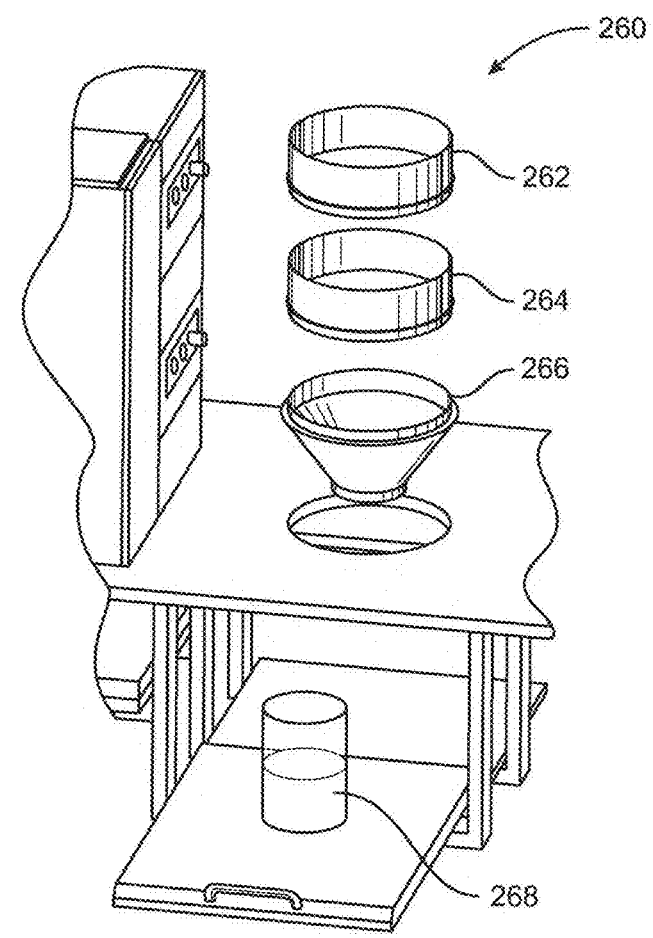
FIG. 11 is a perspective view of a sieve station of the system shown in FIGS. 8A, 8B.

The finely ground VB segments and processing medium are collected in the collection pan 252 and the plate 253 can be moved to a sieve station 260 (FIGS. 8A-8B), whether manually or automatically. Once at the sieve station 260 the contents of the pan 252 are dropped into a sieve cartridge unit which includes two 12" diameter filter sieves—a #40 sieve 262 on top followed by a finer #80 sieve 264, as depicted in FIG. 11. A funnel 266 directs the filtered contents to a collection container 268. The grindings retained by the filters are rinsed within the sieve station 260 with processing/resuspension medium that does not include DNAse™. The liquid bone marrow product in the collection container 268 can be analyzed to determine cell content and then concentrated and packaged in appropriate volumes for cryopreservation, as described below. Alternatively, some or all of the processed bone marrow can be further processed using automated cell selection approaches for specialized cell products such as CD34+ cells. Because large volumes of cells can be recovered from a single organ donor with this approach, one donor could yield multiple product types. Moreover, since the source is primary bone marrow (as opposed to G-CSF mobilized peripheral blood) the cell product will endure cryopreservation processing.

In one modification, the output from the grinding station 240 or the sieve station 260 can be automatically fed to a collection bag for cryogenic treatment. In this modification, the lower funnel 250 can be configured to direct the contents to a fluid line connected to a sterile bag. A peristaltic pump can engage the fluid line to pump the output from the grinding station to the sterile bag. A similar arrangement can be engaged to the funnel 266 of the sieve station.

The content of the collection container 268, which is essentially a bone marrow slurry, is conveyed, either manually or automatically, to an adjacent tumbler station 270 that includes a mechanical tumbler 272 and a large disposable vessel 274 that can contain the entire contents of ten processed VBs and associated processing/resuspension medium. The tumbler 272 has a paddle for agitation of the grinding slurry to mechanically liberate cells. When the tumbling cycle is complete, the contents of the tumbler are poured through a sieve magazine into the vessel 274. The contents of the vessel 274 can be processed further or prepared for cryogenic storage.

Cell Isolation from Bone Marrow

In one aspect of the present disclosure, a method is provided for selecting CD34-expressing (CD34+) cells from deceased donor bone marrow using density reduced FICOLL® (a neutral, highly branched, high-mass, hydrophilic polysaccharide which dissolves readily in aqueous solutions) and an immunomagnetic CD34+ cell isolation kit. Surprisingly, it has been found that cell isolation using density reduced FICOLL® prior to CD34 selection is beneficial to obtain high purity and viability CD45/CD34+ cells from freshly prepared deceased donor bone marrow. On the other hand, FICOLL® at conventional density has been found to be optimal for CD45/CD34+ cell selection from thawed cryopreserved deceased donor bone marrow.

Vertebral sections obtained from a recently deceased donor were processed as described above. Thus, in one embodiment, the bone is cleaned of all soft tissue and then cut into small pieces that were immediately submerged into 500 mL of grinding media. The grinding media can be PLASMA-LYTE™ A injection pH 7.4, multiple electrolytes, injection type 1 USP (PLASMA-LYTE™) containing 2.5% human serum albumin (HSA), 3 U/ml DENARASE®, and 10 U/ml heparin. The sectioned VB are ground using a bone grinder, filtered and rinsed with rinse media (such as PLASMA-LYTE™ with 2.5% HSA). The entire cell suspension is centrifuged to concentrate cells to $2\text{-}3\times10^8$/ml and the cell concentration is extracted. A portion or all of the resulting BM preparation can be used immediately for CD34 selection, while the remainder can be prepared for cryopreservation. The cryopreserved portion involves adding a final concentration of 10% DMSO and 5% HSA to the BM cells and bringing the preparation to −86° C., either by passive cooling or by controlled cooling at a rate of approximately −1° C./min, after which the cryopreserved portion is plunged into liquid nitrogen.

For selection of CD34+ cells, either the newly processed BM preparation is used or a previously cryopreserved portion is thawed for use. FICOLL®-Paque PLUS is added to the BM preparation to separate the desired CD34+ cell component of the bone marrow. It has been found for cell selection from cryopreserved bone marrow that the conventional density for the FICOLL® of 1.077 g/mL produces acceptable results. However, in one aspect of the present disclosure, for cell selection from freshly prepared deceased donor bone marrow the FICOLL® density is reduced from the conventional density. In particular, the density is reduced by mixing FICOLL®-Paque PLUS (density 1.077 g/mL, GE Company) with Plasma Lyte-A Injection pH 7.4 (Baxter Healthcare 2B2544X) in specific proportions to obtain an overall density of less than 1.077 g/ml, particularly 1.063-1.052 g/mL. In one specific embodiment, the density of 1.063 g/mL was found to be optimal for isolation of CD34+ cells, taking into account quantity, viability and purity of the CD34+ cells.

In one embodiment, 5 ml of the 1.063 g/mL density FICOLL® solutions is pipetted into 15-ml centrifuge tubes, and the BM solution generated from VBs of deceased donors is carefully layered over the FICOLL® gradient. The tubes are centrifuged for 30 min at 400 g without break at room temperature. After centrifugation, buffy coat cells are harvested carefully, and the cells are washed in phosphate-buffered saline (PBS) containing 0.5% HSA and 2 mM Ethylenediaminetetraacetic acid (EDTA) (MACS buffer, Miltenyi). In one specific embodiment, centrifugation is performed for 5 min at 400 g, and the resulting cell pellets are resuspended in 10 ml PBS, followed by a second centrifugation for 5 min at 400 g.

Nucleated cells in the isolated buffy coat can be counted using a hematology analyzer, e.g., SYSTEMEX XP-300™. A CELLOMETER® Vision (Nexcellom) or flow cytometer can be used to determine cell counts of purified CD34 cells. 20 microliters of AOPI can be added to 20 microliters of cells and after mixing total viable cells can be determined. The CD34+ cells can be selected by a positive immune separation method using a CLINIMACS® system (Miltenyi, Bergisch Gladbach, Germany) or an EasySep™ CD34 kit (Stemcell Technologies, Vancouver, BC, Canada) in accordance with the protocol of the manufacturer. From testing at various FICOLL® densities it has been surprisingly determined that the lower FICOLL® density contemplated in the present disclosure (i.e., 1.063-1.052 gm/mL vs. the conventional 1.077 gm/mL density) leads to more optimum cell recovery. Optimization is based on purity, viability and yield of selected CD34 cells. A target of >90% purity and >90% viable CD34+ cells is preferred. While lower FICOLL® densities resulted in greater purity and fewer dead cells, it was surprisingly found that a greater portion of the CD34+ cells present in the deceased donor whole bone marrow before selection are lost using the lower FICOLL® densities to prepare buffy coat. Thus, the high viability and purity of CD45/CD34+ cells achieved at the conventional FICOLL® density gradient also leads to a large loss in yield (approximately 60% loss of input CD34+ cells).

Thus, in accordance with one aspect of the present disclosure, for freshly prepared the optimal density of FICOLL® for selection of CD45/CD34+ cells at >90% purity and viability is less than 1.077 and particularly 1.063-1.052. This FICOLL® density provides a higher yield of CD45/CD34+ cells with similar purity and cell viability to the conventional FICOLL® density approach.

In another aspect of the present disclosure, the CD34+ cells can be initially acquired from a freshly prepared deceased donor bone marrow using the reduced density FICOLL-Paque described above. The BM can be cryogenically frozen and then the CD34+ cells can be acquired later using conventional density FICOLL®-Paque. This approach essentially allows selective recovery of cells from deceased donor bone marrow—either before freezing using the modified FICOLL® density or after freezing and thawing using conventional FICOLL® density.

Recovery of MSCs from Processed Bone Marrow

In another feature of the systems and methods disclosed herein, a method is provided for recovering mesenchymal stem cells (MSCs) from enzymatically digested vertebral body (VB) bone fragments that are the byproduct of the VB grinding and elution steps of the methods described herein. In this method, a mixture of both collagenase and neutral protease is used to obtain the highest possible yields of vertebral bone adherent MSC (vBA-MSC). The MSCs can be recovered from cryopreserved VB bone fragments that are later processed according to the present disclosure. In one specific aspect, recombinant *Clostridium histolyticum* collagenase, comprised of the two active isoforms, is used in effective amounts in the MSC extraction process. The mixture of cells liberated by digesting VB bone fragment is cultured on tissue-coated plastic in the presence of Mesencult medium to select proliferative vBA-MSC. Freshly digested preparations as well as different passages of VB-MSC can be characterized by flow cytometry, colony forming unit-fibroblast (CFU-F) potential, population doubling time (PDT) and trilineage (adipogenic, chondrogenic and osteogenic) differentiation in vitro.

The present disclosure thus contemplates a method for optimizing digestion and MSC recovery from vertebral bone fragments using a combination of purified collagenase and neutral protease. In one specific embodiment, the collagenase is DE collagenase (VITACYTE®), which is comprised of purified *Clostridium histolyticum* collagenase and Paneibacillus *polymyxa* neutral protease. In accordance with one aspect of the disclosure, optimal neutral protease concentration and collagenase concentrations (C1 and C2 collagenase) and optimal ratio of solution volume (mLs) to bone fragment weight (mgs) are determined.

According to the process, fragments of VB bone are placed in cryoprotectant solution comprised of PLASMA-LYTE™, 2.5% human serum albumin and 10% dimethyl sulfoxide (DMSO) and incubated for 1 hour at 4° C. The solution is removed and the bone fragments cooled at a rate of ~1°/min to −86° C. and then plunged into liquid nitrogen. After 24-48 hours in liquid nitrogen, the bone fragments are thawed rapidly in a water bath set at 37° C. and then washed in saline and digested using the collagenase/protease solution described above.

The optimal volume-to-weight ratio has been found to be 5:1 at an optimal incubation time of 2.5 hours. The optimal protease produced neutral protease activity of 19.6 U/mL. On the other hand, it was found that total viable MSC cell count is generally insensitive to collagenase concentration.

It was also found that the yields produced by recombinant collagenase isoforms C1 and C2 are similar to the yields with purified collagenase, regardless of the C1/C2 ratio. Further details of the MSC recovery process of the present disclosure are found in the technical article as disclosed in Example 1 of the present application.

Predicting Cell Viability Based on Ischemia Time

As discussed above, ischemia time of the donor bone impacts the viability of the cells extracted using the processes described above. According to the present disclosure, total ischemia is defined as the interval starting at time of death (the point at which the donor's arterial system was cross-clamped and circulation ceased) and ending with the start of the recovery of cells from the bone. For purposes of statistical modeling, this total interval can be separated into three successive and mutually exclusive time components: (a) Warm Ischemia Time (WIT)—beginning at time of death and ending either when bones are recovered and packed on ice or when the body is placed in a cooler; (b) Body Cooling Time (BCT)—beginning when the body is placed in the cooler and ending when bones are packed on ice; and (c) Cold Ischemia Time (CIT)—beginning when bones are packed on ice and ending when processing begins for extraction of cells, such as HSPCs. Thus, Total Ischemia Time=(WIT)+(BCT)+(CIT). For cases where whole-body cooling is not used, BCT is zero and Total Ischemia Time=(WIT)+(CIT).

In addition to Total Ischemia Time, a variable corresponding to processing experience can be incorporated into the viability determination. It is known that learning curves exert significant effects on outcomes, so to control for this fact a variable EXP can be defined as the number of donors processed prior to the current donor—i.e., for the $i^{th}$ donor, EXP=i−1. Other variables can include bone type (such as vertebral bodies and ilia), donor sex and donor age.

In one aspect, the outcome variables are: the proportion of a particular cell population, such as CD34+ cells, that are viable, the total number of colony forming units (CFUs) per $10^5$ nucleated cells detected following cell processing, and the number of CFU granulocyte macrophages (CFU-GM) detected per $10^5$ nucleated cells.

According to the present disclosure, an ordinary least squares (OLS) beta regression model can be used to predict the outcome variables, with linear regression models used for CFU and CFU-GM and a beta regression model used for the proportion of viable CD34+ cells, or % CD34+, where 0<(% CD34+)<1. The beta regression equation for predicting % CD34+ is:

$$\eta = \ln[pCD34^*/(1 - pCD34^*)] \tag{1}$$

$$= \beta_0 + \beta_1(WIT) + \beta_2(BCT) + \beta_3(BCT^2) + \beta_4(CIT) + \beta_5(CIT^2)$$

Where:
pCD34*=[1+100(% CD34+)]/102, which is a transformation of the variable of interest
$\beta_0$=Constant (intercept)
$\beta_1$=Coefficient associated with warm ischemia time (WIT)
$\beta_2$=Coefficient associated with body cooling time (BCT)
$\beta_3$=Coefficient associated with body cooling time squared ($BCT^2$)
$\beta_4$=Coefficient associated with cold ischemia time (CIT)
$\beta_5$=Coefficient associated with cold ischemia time squared ($CIT^2$)

An inverse link function is applied to the linear predictor $\eta$ so that the result is the expected value of the outcome variable pCD34*, namely the percentage of viable CD34+ cells expected to be extracted from the donor bone. The inverse link function is:

$$E[pCD34^*] = \frac{\exp(\eta)}{[1+\exp(\eta)]} \quad (2)$$

or substituting Equation (1) above for $\eta$:

$$E[pCD34^*] = \frac{\exp(\eta)}{[1+\exp(\eta)]} = \frac{\exp[\beta_0 + \beta_1(X_1) + \beta_2(X_2) + \beta_3(X_3) + \beta_4(X_4) + \beta_5(X_5)]}{[1+\exp(\beta_0 + \beta_1(X_1) + \beta_2(X_2) + \beta_3(X_3) + \beta_4(X_4) + \beta_5(X_5))]} \quad (3)$$

In this embodiment, the mathematical model predicts the proportion of viable CD34+ cells that can be extracted from the donor bone that has been subjected to the specific ischemia conditions. The value of $E[pCD34^*]$ is between 0 and 1 since it is the ratio of the number of viable CD34+ cells to the total number of CD34+ cells in the bone sample.

In one embodiment, the coefficients for the beta regression calculation of the predicted % CD34+ have the following values:
$\beta_0=3.5000$
$\beta_1=-0.01996$
$\beta_2=-0.181$
$\beta_3=0.007$
$\beta_4=-0.111$
$\beta_5=0.002$
where each of the beta coefficients $\beta_0$, $\beta_1$, $\beta_2$, $\beta_3$, $\beta_4$, $\beta_5$ correspond to the intercept, WIT, BCT, $BCT^2$, CIT and $CIT^2$, respectively, as described above.

The predictions for the total colony forming units CFU and the number of CFU granulocyte microphages CFU-GM can be obtained using the following linear regression model:

$$\eta=\beta_0+\beta_1(WIT)+\beta_2(BCT)+\beta_3(BCT^2)+\beta_4(CIT) \quad (4)$$

The linear regression model used to determine the CFU outcome variable can have the following coefficient values:
$\beta_0=756.5084$
$\beta_1=-9.10826$
$\beta_2=-95.03639$
$\beta_3=3.45603$
$\beta_4=-4.53349$,
where each of the beta coefficients $\beta_0$, $\beta_1$, $\beta_2$, $\beta_3$, $\beta_4$ correspond to the intercept, WIT, BCT, $BCT^2$ and CIT, respectively, as described above.

The linear regression model used to determine the CFU-GM outcome variable can have the following form:

$$\eta=\beta_0+\beta_1(WIT)+\beta_2(BCT)+\beta_3(CIT) \quad (5)$$

with the following coefficient values:
$\beta_0=104.1805$
$\beta_1=-8.11295$
$\beta_2=-5.52927$
$\beta_3=0.08872$.

The foregoing models are base or un-adjusted models that only account for the ischemia-based variables and not the experience, bone type, donor sex and donor age variables. A fully adjusted model for % CD34+ that accounts for all of the variables can have the following form:

$$\eta=(\beta_0+\beta_1(\text{Experience})+\beta_2(\text{Bone Type})+\beta_3(WIT)+\beta_4(BCT)+\beta_5(BCT^2)+\beta_6(CIT)+\beta_7(CIT^2)) \quad (6)$$

with the following respective values for the coefficients:

| % CD34+ | |
|---|---|
| $\beta_0$ Constant | 3.112681 |
| $\beta_1$ Experience | 0.0095651 |
| $\beta_2$ Bone Type (VB = 1) | 0.0351495 |
| $\beta_3$ Warm Ischemia (WIT) (hrs)$^a$ | −0.0229737 |
| $\beta_4$ Body Cooling (BCT) (hrs) | −0.176881 |
| $\beta_5$ Body Cooling Squared ($BCT^2$) | 0.0062293 |
| $\beta_6$ Cold Ischemia (CIT) (hrs) | −0.101344 |
| $\beta_7$ Cold Ischemia Squared ($CIT^2$) | 0.0013874 |

The fully adjusted model for CFU is as follows:

$$\eta=\beta_0+\beta_1(\text{Experience})+\beta_2(\text{Facility}\times\text{Experience})+\beta_3(\text{Bone Type})+\beta_4(WIT)+\beta_5(BCT)+\beta_6(BCT^2)+\beta_7(CIT)+\beta_8(CIT^2) \quad (7)$$

| CFU | |
|---|---|
| $\beta_0$ Constant | 160.6034 |
| $\beta_1$ Experience | 2.60499 |
| $\beta_2$ Facility x Experience | 5.36988 |
| $\beta_3$ Bone Type (VB = 1) | 206.9969 |
| $\beta_4$ Warm Ischemia (hrs) | −3.73481 |
| $\beta_5$ Body Cooling (hrs) | −82.49506 |
| $\beta_6$ Body Cooling Squared | 2.95994 |
| $\beta_7$ Cold Ischemia (hrs) | 9.55975 |
| $\beta_8$ Cold Ischemia Squared | −0.12535 |

The coefficient 1 attempts to quantify the effect of the number of donors processed (i.e., experience) on cell quantity and viability. In the fully adjusted CFU model, coefficient $\beta_2$ corresponds to the experience at a particular facility based on the assumption that facilities can have different learning trajectories. Either or both of these coefficients may be modified or even eliminated.

| CFU-GM | |
|---|---|
| $\beta_0$ Constant | 88.3589 |
| $\beta_1$ Bone Type (VB = 1) | 16.71592 |
| $\beta_2$ Warm Ischemia (hrs) | −7.19329 |
| $\beta_3$ Body Cooling (hrs) | −5.24410 |
| $\beta_4$ Cold Ischemia (hrs) | 0.10750 |

Applying these models to observed data can be used to determine the effect of ischemia time variables on % CD34+, as reflected in the tables shown in FIGS. 12A-12C, on total CFU, as shown in the tables of FIGS. 13A-13C, and on the amount of CFU-GM, as shown in the tables of FIGS. 14A-14C. The data in these tables can be used to decide whether a particular donor bone can yield sufficient cells to warrant further processing of the donor bone. In other words, the predictive models can be used to establish ischemia tolerance limits and HSPC quality acceptance criteria. For instance, with respect to the % CD34+ outcome variable, predicted values of over 80% may be required in order to consider the particular donor bone.

The models described above and the examples shown in the tables of FIGS. 12A-14C suggest that acceptable levels of HSPC quality are achievable despite the prolonged ischemia times that are inevitable when bones must be procured by geographically-dispersed OPOs and shipped long distances to processing centers. Even under such conditions, favorable combinations of warm- and cold-ischemia times can be achieved, enabling % CD34+ viabilities in the range of 80-90%. The models also suggest that refrigerating the body prior to bone recovery, a practice that is common in the recovery of tissues, is less beneficial in the context of bone marrow recovery. For instance, when whole-body cooling was used, CD34+ viability averaged 72.75%, whereas when body cooling was not used, the average was just under 90%. These models suggest that an optimal practice would be to dispense with body cooling and move recovered bone as quickly as possible to a cold ischemic environment. The models further suggest that limiting WIT (warm ischemia time) to less than eight (8) hours and CIT (cold ischemia time) to less than 40 hours optimizes the opportunity to recover meaningful quantities of viable cells from donor bone.

Figure 15:
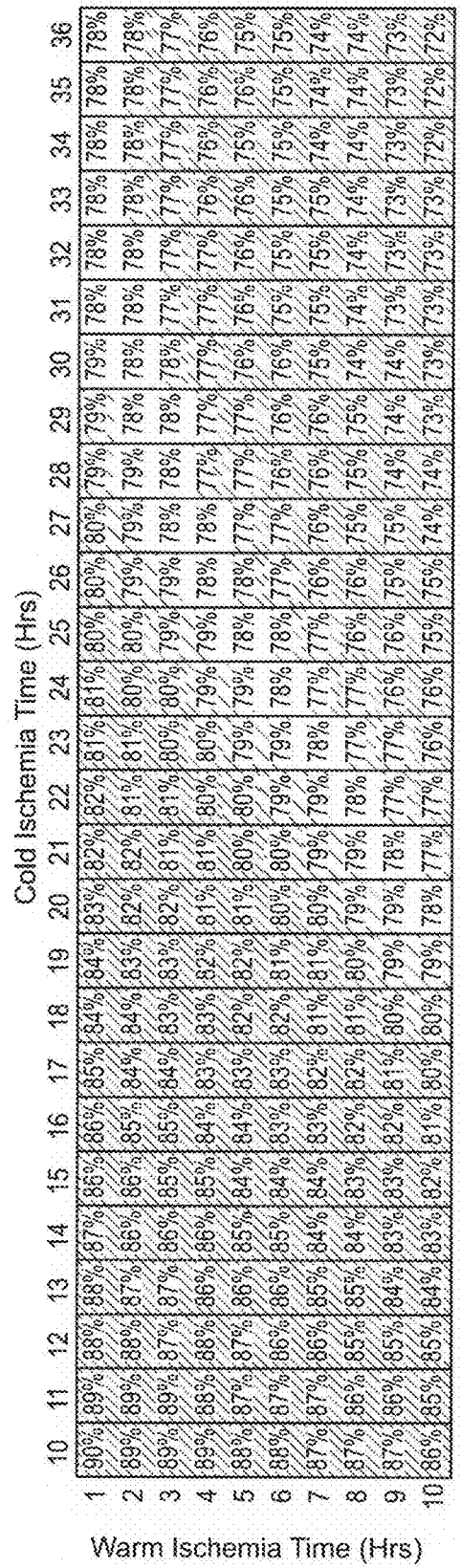
FIG. 15 is a chart of viability threshold as a function of warm ischemia times and cold ischemia times.

The models disclosed herein predict viability according to the chart shown in FIG. 15 in which an 80% CD34+ cell viability threshold is determined to be acceptable. As reflected in the chart, the relationship between warm and cold ischemia times follows a curve from a point at which the WIT is 10 hours and the CIT is 18 hours, to a point at which the WIT is 1 hour and the CIT is 27 hours.

Further details of the method for predicting cell viability of the present disclosure are found in Example 2 of the present application.

The present disclosure should be considered as illustrative and not restrictive in character. It is understood that only certain embodiments have been presented and that all changes, modifications and further applications that come within the spirit of the disclosure are desired to be protected.

EXAMPLES

Example 1: Identification and Characterization of a Large Source of Primary Human Mesenchymal Stem Cells Tightly Adhered to Bone Surfaces of Vertebral Body Marrow Cavities Therapeutic allogeneic mesenchymal stem/stromal cells (MSC) are currently in clinical trials for evaluating their effectiveness in treating many different disease indications. Eventual commercialization for broad distribution will require further improvements in manufacturing processes to economically manufacture MSC at sufficient scale required to satisfy projected demand. A key contributor to the present high cost of goods (COG) for MSC manufacturing is the need to create master cell banks (MCBs) from multiple donors, which leads to variability in large-scale manufacturing runs. Therefore, the availability of large single donor depots of primary MSC would greatly benefit the cell therapy market by reducing costs associated with manufacturing.

We have discovered that an abundant population of cells possessing all the hallmarks of MSC is tightly associated with the vertebral body (VB) bone matrix and are only liberated by proteolytic digestion. Here we demonstrate that these vertebral bone-adherent (vBA) cells possess all the International Society of Cell and Gene Therapy (ISCT)-defined characteristics (e.g., plastic adherence, surface marker expression and trilineage differentiation) of MSC and, therefore, have termed them vBA-MSC, to distinguish this population from loosely associated MSC recovered through aspiration or rinsing of the bone marrow (BM) compartment. Pilot banking and expansion was performed with vBA-MSC obtained from 3 deceased donors and it was demonstrated that bank sizes averaging $2.9 \times 10^8 + 1.35 \times 10^8$ vBA-MSC at passage one were obtainable from 100 g of digested VB bone fragments. Each bank of cells demonstrated robust proliferation through a total of 9 passages without significant reduction in population doubling times. The theoretical average total yield with limited expansion of 4 passages yielded 2 trillion ($2 \times 10^{12}$) cells from a single donor, equating to 30,000 doses at $10^6$ cells/kg for an average 70 kg patient. Thus, we have established a new and plentiful source of MSC which will benefit the cell therapy market by overcoming manufacturing and regulatory inefficiencies due to donor-to-donor variability.

Introduction

The potent activity as well as high expandability of mesenchymal stromal/stem cells (MSC) has generated considerable interest from commercial entities in developing "off-the-shelf" allogeneic MSC therapeutics derived from a limited number of donors. Development of a cellular therapy based on allogeneic "universal donors" allows for controlled manufacture with careful attention to thoroughly assessing quality (e.g., identity, potency, purity and safety) of each manufactured lot at significant cost savings compared to manufacturing individual lots of autologous cells for individual donors, such as currently occurs for chimeric antigen receptor (CAR) T cell therapies.

The challenges inherent to manufacturing cellular therapies scale with the size of a manufacturing run. Effective doses of MSC for some indications are as high as $1 \times 10^9$ cells per dose, which would require manufacturing 10 trillion ($10 \times 10^{12}$) cells per year to affordably meet potential demand [1-4]. Even at this level of production, with presumed economies of scales, the cost of goods (COG) per dose of MSC could exceed $100,000 [3]. A significant driver of manufacturing costs, which is amplified proportionately with lot size, is the need to replenish master cell banks (MCB) through isolation of MSC from new donors due to the limited volumes of tissues and fluids that can be safely obtained from healthy volunteers and the limited expansion potential of MSC isolated from each donor [5, 6]. MSC are rare in all tissues, comprising, for instance, ~0.001-0.01% of total nucleated cells (TNC) in BM aspirates [7]. Given that BM aspirates from healthy volunteers are limited for the safety of the donor to 100 ml (50 ml bilaterally from iliac crests), the total yield of fresh, non-passaged MSC is approximately $2 \times 10^4$/donor. Expansion to a trillion cells would require seed stocks of $1 \times 10^7$ MSC in order to limit cell proliferation to 9 population doublings [8]. This number is in addition to the cells reserved for quality control measurements of the expanded MCB and working cell bank (WCB). Thus, the number of MSC obtainable from each donor is more than 3 orders of magnitude less than is optimal for the initial stages of expansion.

The need to constantly replenish cell banks by obtaining fresh cells from new donors introduces inconsistencies into the manufacturing process due to the observed variability between MSC derived from different donors otherwise matched for attributes such as age and health status [6, 9, 10]. Donor-to-donor variability and the resulting economic impact on manufacturing costs is substantial. In one study that examined large scale manufacturing of multiple lots of MSC derived from different donors it was found that cumulative population doublings between 5 different BM donors varied by 1.8-fold during 30 days in culture [9]. The result was a >13 day variation in process time to manufacture a batch of 350 million MSC. Besides the logistical burden to coordinate batch runs, there was a commensurate increased cost of growth medium, which is also a key cost-driver for cell-based therapy manufacturing [1, 3, 8]. Furthermore, the authors found that there was >18% difference in colony forming potential and >50% difference in interleukin 6 expression, adding an additional complication to quality control verification of potency for each batch derived from individual donors. Similarly, a single center experience with clinical manufacture of 68 batches of MSC from BM recovered from 59 human volunteer donors observed population doubling times that varied by over 2-fold (46.8141 hours), averaging 71.7 hours, yielding final batch numbers of MSC ranging from $1.9 \times 10^7$ to $5.43 \times 10^9$ (average $5.46 \times 10^8$) [10].

Besides imposing a direct economic burden of increasing COG per manufacturing run, there is also a regulatory burden with associated costs resulting from the need to refresh cell banks. The MCB serves as the reserve of starter cultures for all manufacturing runs using cells from a particular donor. The regulatory requirements for quality and safety assessments of the MCB are costly and time consuming [11]. Of the three overarching parameters (e.g., safety, potency and identity) required to assess suitability of a manufactured cell therapy product, potency as it relates to individual donor characteristics, is most problematic due to the changing profile that occurs with expansion, as described above. This is particularly the case as MSC populations near the limits of expansion and enter into senescence which severely limits their potency [12]. For these reasons, population doubling limits is an important factor for regulatory authorities; albeit, one that is not commonly addressed in filings with FDA [13].

Reducing the economic and regulatory burden of generating multiple MCB lots annually to fulfill the need for large scale manufacturing requires identifying large depots of unmanipulated MSC. Potential solutions could come from abundant tissues harboring MSC that are normally discarded following routine medical procedures or are obtainable post-mortem. Adipose-derived stem/stromal cells (ASC) are obtained from elective procedures that commonly yields liters of tissue and have recently been extensively investigated; however, primarily for autologous uses [14, 15]. Isolation directly from medullary cavity-containing bones obtained through medical procedures or cadavers yields higher percentages of MSC (~0.04%) than are present in aspirates, most likely reflecting lack of peripheral blood contamination [16]. Total nucleated cell counts of $\sim 5 \times 10^9$ have been obtained from BM of vertebral bodies (VB) recovered from deceased organ donors, with each VB containing $\sim 2 \times 10^6$ MSC, or $\sim 2 \times 10^7$ total MSC per typical spinal 9 VB segment recovered [17]. In addition, the ilia, sternum, ribs and heads of long bones are sources of BM from which MSC can be recovered [18-20]. Thus, the VB compartment of BM alone from a typical deceased donor yields >3 orders of magnitude more MSC than can be obtained from a health human donor.

In addition to cells obtained by eluting or aspirating BM, another population of MSC is tightly associated with medullary cavity bone structures [21-23]. First identified in rodent long bones, bone-adherent MSC (BA-MSC) have subsequently been isolated from human bone fragments obtained from long bone condyles and vertebrae [24]. We have discovered another source of MSC, termed vertebral BA-MSC (vBA-MSC), which remain attached to fragments of VB bone after extensive washing to remove BM cells and can only be liberated by digestion with proteases. The frequency and functionality of vBA-MSC is equivalent to that in eluted VB BM-MSC. Here we present these data and establish a new source of MSC that could be used in large scale manufacturing processes to produce batches totaling of over a quadrillion cells from an individual donor; thus, satisfying the most optimistic levels of demand for decades and overcoming a current impediment to commercial scale production [2, 8].

Materials and Methods
Sources of Tissues and Cells

Vertebrae were recovered following cardiac death of brain-dead organ donors after obtaining informed consent for research use from surviving family members. Each recovered vertebra was assigned a unique ID. The inclusion criteria for donor selection were brain death, age between 12 and 55 years, non-septicemic, and disease and pathogen free. Live donor aspirated BM from three healthy volunteers was purchased from Lonza (Walkersville, Md.). Expanded live donor MSC, cryopreserved at passage 2, were purchased from Lonza. Relevant donor characteristics are presented in Table 1.

Deceased Donor Tissue Procurement and Transport

Previously developed clinical recovery methods [16, 25] combined with subsequent experience in the ongoing VCA transplant immune tolerance clinical trial (ClinicalTrials.gov Identifier: NCT01459107) at Johns Hopkins University formed the basis for the procurement and transport protocols. A streamlined organ procurement agency (OPO) recovery procedure, combined with dedicated kits and centralized training on recovery and shipment procedures were employed. Recovered bones were shipped to Ossium Health (Indianapolis, Ind.). Vertebral sections were procured by six different OPO partners: Gift of Hope (Itasca, Ill.); Donor Alliance (Denver, Colo.); Iowa Donor Network (North Liberty, Iowa); Mid America Transplant (St. Louis, Mo.); and Nevada Donor Network (Las Vegas, Nev.). Bones were recovered by OPO personnel using an osteotome and mallet under an IRB approved protocol from research-consented organ and tissue donors. Recovered bones were wrapped in lap sponges and towels soaked in saline to ensure moisture retention during shipment. Wrapped specimens were shipped overnight on wet ice to one of the two processing facilities.

Manual Debriding

Upon receipt, in a Biological Safety Cabinet, soft tissue was manually debrided using scalpels and gouges. Once visible, the pedicles were removed using either a tissue processing band saw or a Stryker System 6 Saw (Stryker, Kalamazoo, Mich.) leaving only the connected vertebral bodies. Vertebral bodies were separated and intervertebral disc and soft tissue was removed with a scalpel. Care was taken to ensure that the cortical bone was not breached to preserve and protect the hypoxic cancellous bone marrow throughout the entire debriding process.

Using custom-made surgical grade stainless-steel anvil shears, VBs were cut into approximately 5 cm$^3$ pieces small enough to be fragmented with a bone grinder. The pieces were immediately submerged into 500 mL processing medium comprised of PLASMA-LYTE™ A pH 7.4 (Baxter Healthcare, Deerfield, Ill.), containing 2.5% human serum albumin (HSA; Octapharma USA Inc., Hoboken, N.J.), 3 U/ml BENZONASE® (EMD Millipore, Burlington, Mass.), and 10 U/ml heparin (McKesson, Irving, Tex.).

Grinding and Elution

A bone grinder (Biorep Technologies. Inc, Miami, Fla.) was assembled in a biological safety cabinet. A two liter stainless steel beaker containing approximately 250 mL of fresh processing medium was placed under the grinding head to catch bone chips and media flow-through. A stainless steel plunger was used to aid in pushing pieces through the grinder. Rinsing through the grinder with processing medium prevented bone pieces from drying out and sticking to the chamber. Once all bone pieces were ground, the chamber was thoroughly rinsed with fresh processing medium. The final volume in the stainless-steel beaker was one liter.

Filtering was performed using bone marrow collection kits with flexible pre-filter and inline filters (Fresenius Kabi, Lake Zurich, Ill.). All bone grindings and media were carefully transferred to the bone marrow collection kit. The grindings were gently massaged to allow for optimal cell release from grindings. The media was then filtered using two 500 μm and two 200 μm filters. The bone grindings are rinsed using two 500 mL washings with rinse media. Rinse media was PLASMA-LYTE™ with 2.5% HSA. All bone marrow was then collected in a collection bag where samples were taken for experiments.

Digestion Protocol for MSC Isolation

Bone fragments (either 1 or 100 g) were transferred to either 50 ml conical centrifuge tubes or 250 ml WHIRL-PAK® bags. A solution of DE10 collagenase (2 mg/ml; VITACYTE®, Indianapolis, Ind.) was added to the bone fragments at a ratio of 5:1 (volume:weight). The tubes and/or bags were transferred to a shaking incubator and incubated for 2 hr at 37° C. while shaking at 125 rpm. Protease activity was neutralized by adding 2% STEMULATE® (Cook Regentec, Indianapolis, Ind.) and suspensions were filtered through a 70 μm cap filter into 50 ml conical screw cap tubes. The filter-retained bone fragments were washed with 25 ml Dulbecco's modified phosphate buffered saline (DPBS) solution containing heparin (10 U/ml) and BENZONASE® (100 U/ml) which was combined with the original filtrate. Tubes were centrifuged at 350×g for 5 minutes, supernatant aspirated, and the pellets were resuspended in 10 ml DPBS. The suspension was centrifuged again at 350×g for 5 minutes, the supernatant was aspirated, and the pellet was resuspended in DPBS for analysis.

Isolation of MSC from Iliac and VB BM

An 1 ml aliquot of concentrated, eluted BM was removed and pipetted into a 50 ml conical vial along with 49 ml DPBS. The vial was centrifuged at 300×g for 10 minutes, supernatant aspirated, and the pellet resuspended in 10 ml Rooster-Nourish medium (Rooster Bio, Frederick, Md.). Cells were counted and cultured as described below Isolation of MSC from Iliac and VB BM An 1 ml aliquot of concentrated, eluted BM was removed and pipetted into a 50 ml conical vial along with 49 ml DPBS. The vial was centrifuged at 300×g for 10 minutes, supernatant aspirated, and the pellet resuspended in 10 ml Rooster-Nourish medium (Rooster Bio, Frederick, Md.). Cells were counted and cultured as described below Cell Counting A CELLOMETER®Vision (Nexcellom, Lawrence, Mass.) was used to determine total viable cell counts. 20 μl VIASTAIN™ AOPI reagent (Nexcelom) was added to an Eppendorf tube containing 20 μl of cells. Once mixed, 20 μl of the solution was added to a CELLOMETER® slide and total cells, live cells, and viability were calculated.

Cell Culture

Fresh cells were plated in CellBIND® T-225 flasks at a density of 25,000 viable cells/cm$^2$ in Rooster-Nourish medium (Rooster Bio, Frederick, Md.). Nonadherent cells were removed after the first media change on day 1. Media was then changed every 3-4 days until colonies were ~80-90% confluent. Cells were released with TRYPLE™ (ThermoFisher Scientific, Waltham, Mass.). Passaged cells were plated at a density of 3,000 cells/cm$^2$ but otherwise followed the same protocol as freshly plated cells.

Generation of MCBs from three donors (DD5, DD6 and DD7) was performed in CellBind® Hyperflasks. Fresh, primary digests were initially plated at 25,000 viable cells/cm$^2$ as above. Cells were released with TRYPLE™ and expanded one more passage to form the MCB. The bulk of passage 1 cells were resuspended in cryopreservation medium (CryoStor CS10; BioLife Solutions, Bothell, Wash.) and stored in the vapor phase of liquid nitrogen.

Cells were passaged up to ten times in a medium composed of DMEM (Cat #10567014, ThermoFisher, USA), ascorbic acid (248 μM; Cat #A2218, Sigma, USA), recombinant basic fibroblast growth factor (10 ng/ml; Cat #233-GMP-025, R&D Systems, USA) and recombinant epidermal growth factor (10 ng/ml; Cat #236-GMP-200, R&D Systems, USA). Cells at 70-80% confluency were harvested and total cell counts were obtained. A portion of the cells was re-plated at 3000 cells/cm$^2$ in triplicate wells of a six-well plate, with media changes every 3-4 days.

Phenotypic Analysis of MSC via Flow Cytometry

At passages 2, 3 and 4, 1.8 μl of the following single fluorescently-conjugated antibodies or dye, CD3, CD14, CD19, CD31, CD34, CD45, HLA-DR, CD73, CD90, CD105, Stro-1, and 7AAD (Table S1), were added to different wells of a 96-well V-bottom plate. 100 μl of MACS (Miltenyi BioTec) buffer and 100 μl of cells (200,000 cells) were added to each well containing an antibody. The plate was incubated at 4° C. for 30 minutes shielded from light and afterward, the plate was centrifuged for 5 minutes at 300×g. Cells were washed and resuspended in 200 μl of MACS buffer. An ACEA Biosciences NOVOCYTE® 2060R flow cytometer was used for data collection and data was analyzed using NOVOEXPRESS® software (Acea Biosciences San Diego, Calif.).

Trilineage Differentiation of MSC

MSCs after passage 1 were seeded in wells of a 12-well plate containing 3 ml MESENCULT™ (Stem Cell Technologies, Vancouver, B.C.) each at 8.0×10$^4$, 4.0×10$^4$, and 2.0×10$^4$ for chondrogenesis, adipogenesis, and osteogenesis differentiation. A well of containing 4.0×10$^4$ MSCs was also plated as a control. After incubating for 2 hours, MESENCULT™ in the chondrogenesis well was replaced with STEMPRO™ chondrogenesis medium (Thermo Fisher Scientific, Waltham, Mass.). After one day, MESENCULT™ in the adipogenesis and osteogenesis wells was aspirated and replaced with STEMPRO™ adipogenesis medium and STEMPRO™ osteogenesis medium, respectively. Respective differentiation media were replenished every 3 days as well as MESENCULT™ in control wells. After 14, 12, and 16 days, wells containing chondrocytes, adipocytes, and osteocytes, respectively, were aspirated of media, washed twice with DPBS, fixed with 4% formalin for 30 minutes, washed once with DPBS, and stained. Alcian Blue, which stains chondrocyte proteoglycans blue, in 0.1 N HCl was added to the chondrocyte well for 30 minutes, the stain was aspirated, the well was washed three times with 0.1 N HCl and neutralized with distilled water, and chondrocytes were visualized under an inverted light microscope (Nikon). Oil Red O, which stains adipocyte fat globules red, was added to the adipocyte well for 15 minutes, the stain was aspirated, the well was washed three times with distilled water, and adipocytes were visualized under an inverted light microscope. 2% Alizarin Red, which stains osteocyte calcium deposits red, was added to the osteocyte well for 3 minutes, the stain was aspirated, the well was washed three times with distilled water, and adipocytes were visualized under an inverted light microscope. All differentiated cells were qualitatively analyzed by visualization of color and phenotypic profile.

Population Doubling Time

Population doubling time was determined at each passage by using the formula: t*log(2)/log(T1/T0), where t is the time (hours) between initial plating and cell harvest at 90% confluency, T1 is the cell count at harvest and T0 is the initial count at seeding.

CFU-F Assays

For freshly digested cells, 5 ml MESENCULT™, 20 µl Amphotericin B, and 100 µl Gentamycin were added to three wells of a 6-well plate. $2.5 \times 10^5$, $5.0 \times 10^5$, and $7.5 \times 10^5$ cells were added to the first, second, and third wells, respectively. Plates were placed in the incubator until colonies were 90% confluent or up to 12 days. Media was changed every 3-4 days for 14 days. Plates were washed twice with DPBS, and 2 ml methanol was added to each dish for 5 minutes to fix the cells. After 5 minutes, the methanol was decanted, the plate was allowed to air dry and colonies were stained with a 1% crystal violet solution. Colonies containing >50 cells were scored. Passaged cells were assayed similarly except that cells were plated at densities of 32 cells/cm$^2$, 65 cells/cm$^2$, and 125 cells/cm$^2$.

T Cell Suppression Assays

Suppression of T cell activation was performed according to previously published protocols with minor modifications [26]. Briefly, peripheral blood mononuclear cells were isolated from whole blood (10 ml) by FICOLL® (GE, Chicago, Ill.) separation and resuspended in DPBS. The majority of cells were labeled with carboxyflourescein succinimidyl ester (CFSE; Sigma, St. Louis, Mo.) and frozen until used [27]. Passage 2 or 3 MSCs, in some cases pre-stimulated with 100 ng/ml interferon-g (IFNγ; RnD Systems, Minneapolis, Minn.) for 18-24 hours, were resuspended in RoosterNourish (RoosterBio, Frederick, Md.) and added to a 96 well flat bottom plate at $4 \times 10^5$, $1 \times 10^5$, $5 \times 10^4$, $2.5 \times 10^4$, $1.5 \times 10^4$, $5 \times 10^3$ cells/well. RoosterNourish was added to each well until the volume was 200 µl/well. The plate was placed in a 37° C. incubator with 10% CO2 at 5% humidity for at least two hours to allow MSCs to attach. Cryopreserved PBMCs were quickly thawed and resuspended at a concentration of $4 \times 10^6$ cells/ml in Eagle's minimal essential medium (EMEM; Stem Cell Technologies; supplemented with 10% FBS, 100 pg/ml PenStrep, 2 mM L-glutamine, and 100 µM b-mercaptoethanol). The medium was aspirated from the plates containing MSC and 100 µl of PBMCs were added to all wells containing MSCs as well as wells without MSCs. T cells were stimulated by adding 100 µl of supplemented EMEM with 40 pg/ml phytohemagglutinin (PHA; Sigma-Aldrich, St. Louis, Mo.) to each well containing MSCs and PBMCs. Control wells containing labeled and unlabeled PBMCs alone were also included, half of which were stimulated with PHA and half which were not. The plate was returned to the incubator. After 4 days, PBMCs from each well were removed and labeled with 5 µl CD3-PE and 5 µl of 7AAD before performing flow cytometry Statistics GRAPHPAD PRISM® version 8 was used for statistical analysis (Student's t Test). An P value <0.05 was considered significant.

Results

A typical vertebral column (typically T8-L5) before and after removing soft tissues, separating VBs and then fragmenting to sizes of approximately 1.5 cm$^3$ is shown in FIG. 16.

FIG. 16A to FIG. 16D show processing of a typical vertebral column to isolate vBA-MSC. The vertebrae (typically T8-L5) is cleaned of soft tissue (FIG. 16A) before separating vertebral bodies (VBs) and removing disks and remaining soft tissues (FIG. 16B). VBs are ground to approximately 1.5 cm$^3$ fragments (FIG. 16C) before enzymatic digestion to release adherent cells. Plastic adherent vBA-MSC form typical spindle shapes in culture (FIG. 16D; passage 2 cells). Plastic adherent vBA-MSC possessed a typical spindle-shaped morphology in culture (FIG. 16D).

Figure 17A:
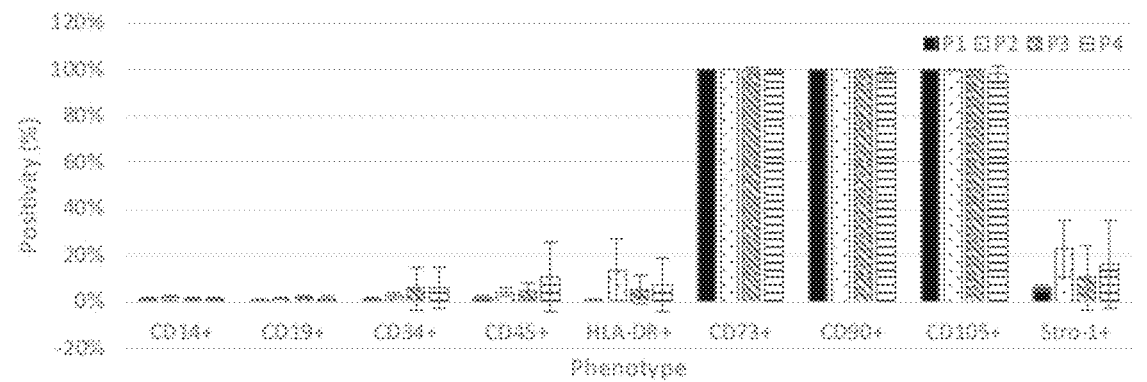
FIG. 17A to FIG. 17E show surface antigen phenotype and trilineage differentiation of vBA-MSC.
Figures 17B, 17C, 17D, 17E:
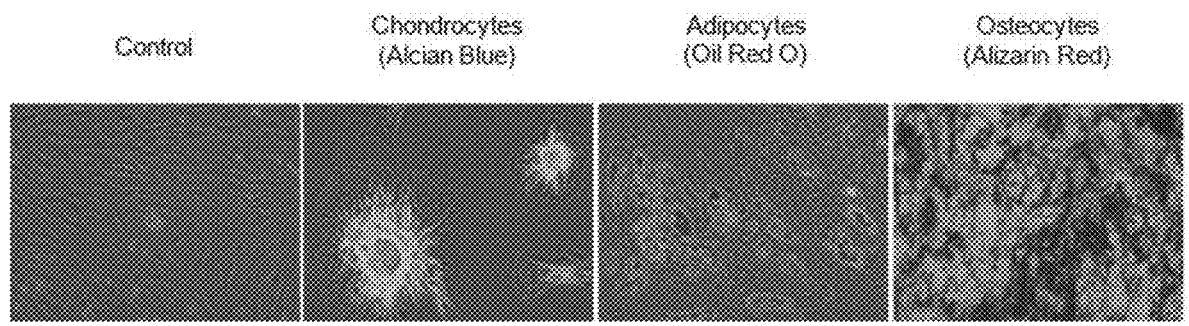

Cells from donors were expanded through passage 4 (the initial plating was considered passage 0) and assayed by flow cytometry. vBA-MSC at passages 1-4 possessed negligible levels of hematopoietic stem and progenitor cell surface markers CD14, CD19, CD34 and CD45 and expressed low to non-existent amounts of human leukocyte antigen DR (HLA-DR) (FIG. 17A). In FIG. 17A, passage 1, 2, 3 and 4 vBA-MSC from 3 different donors (DD1, DD2 and DD23; Table 1) were analyzed for surface antigen expression using fluorescently-conjugated antibodies and flow cytometry. The percentage of cells (gated on whole cells using side and forward scatter) after culturing for each passage is shown. Levels of PECAMl (CD31)-expressing cells (typically endothelial cells and monocytes) were also low (<7%) at passage 2 (data not shown). Conversely, passaged vBA-MSC were uniformly positive for CD73, CD90 and CD105. Thus, vBA-MSc possess the characteristic MSC surface marker profile [28]. In addition, a variable portion (approximately 20% or lower, depending on the passage number) of the population also expressed the multipotential MSC surface marker Stro-1 [29-32].

Chondrogenic, adipogenic and osteogenic potentials of passage 3 vBA-MSC were determined for each donor. Each of the vBA-MSC isolates demonstrated the potential to differentiate into chondrocytes, adipocytes and osteocytes (FIG. 17B to FIG. 17E). Passage 3 vBA-MSC grown in expansion medium (FIG. 17B) or induced to undergo either (FIG. 17C) chondrogenesis, (FIG. 17D) adipogenesis or (FIG. 17E) osteogenesis were imaged after staining for chondrocytes (alcian blue), adipocytes (oil red 0) or osteocytes (alizarin red), as described in Materials and methods. Images are representative of results with the 3 different donor-derived vBA-MSC. Magnification for all 20×. A portion of both freshly isolated (i.e., never plated) as well as passaged vBA-MSC demonstrated high degrees of clonal proliferation, as determined by colony forming unit-fibroblast (CFU-F) potentials.

The average CFU-F frequency in freshly digested VB bone fragments was 0.01+0.004% (mean+standard deviation), which is similar to the frequency of proliferative MSC in whole BM (FIG. 18) [7].

Figure 18:
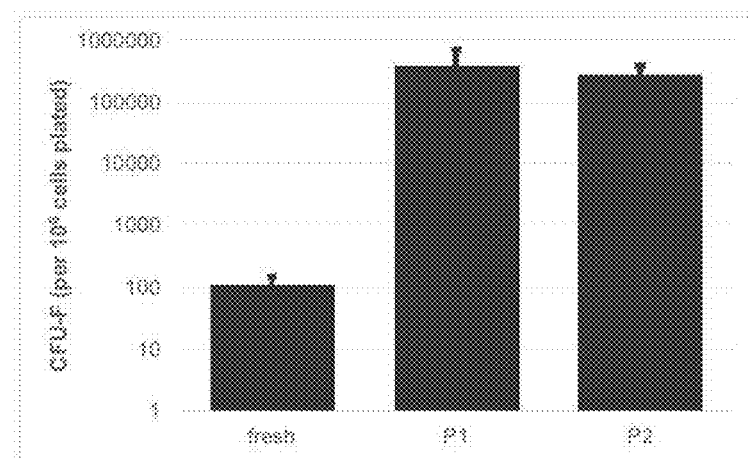
FIG. 18 shows colony forming unit-fibroblast (CFU-F) potential of vBA-MSCs.

FIG. 18 shows colony forming unit-fibroblast (CFU-F) potential of isolated vBA-MSC from 3 different donors (DD1, DD2 and DD3; Table 1) and plated immediately after isolation by digestion (fresh) or after 1 or 2 passages (P1 and P2). Either $5 \times 10^5$ (fresh) or 624 (passaged) total cells from each of 3 donors were plated in triplicate wells of a 6 well plate and incubated for 14 days with media changes every 3-4 days. The proliferative cells were maintained with cell culture, forming colonies at a frequency of 37+3.4% and 27+1.2% after one and two passages, respectively.

Figure 19:
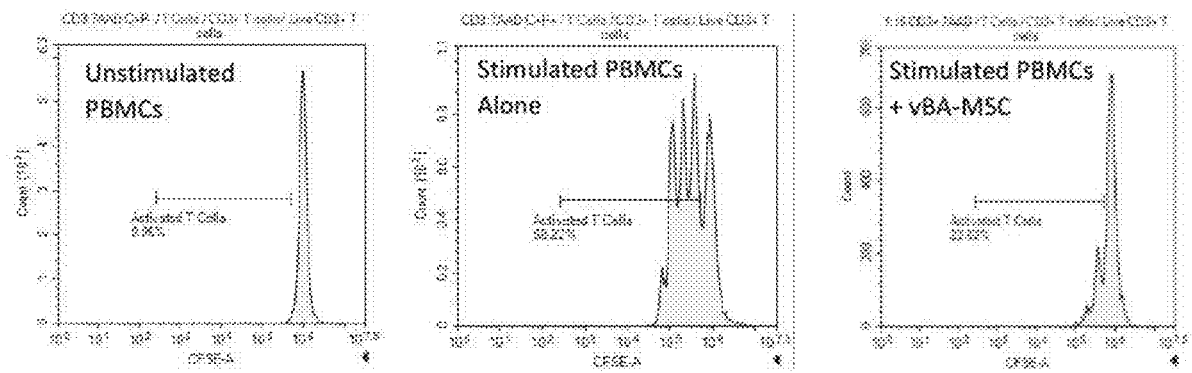
FIG. 19 shows vBA-MSC suppression of T cell activation.

Suppression of T cell activation is one of the best studied therapeutic properties of MSC, providing the rationale for testing in clinical trials of inflammatory disorders [33, 34]. vBA-MSC from the three different donors dose-dependently suppressed T cells activation with PHA (FIG. 19).

PBMC isolated from the blood of a single donor were labeled with carboxyfluorescein diacetate succinimidyl ester (CSFE). vBA-MSC were allowed to adhere 2 hours in 96 well plates before washing and adding 4×10$^5$ PBMC. In some experiments IFNγ (100 ng/ml) was added 18-24 hours before adding PBMC. T cells were stimulated for 4 days with PHA. Cells were recovered from the plates and analyzed by flow cytometry after labeling with anti-CD3-PE antibodies. The percentage of activated T cells is plotted.

Maximum suppression at a 1:1 ratio of vBA-MSC to peripheral blood mononuclear cells (PBMC) was 89+7%. A slight but non-significant increase in suppression at all ratios was observed by pre-treating vBA-MSC with IFNγ for 18-24 hours prior to performing the suppression studies. Treatment with IFNγ has been shown to stimulate suppressive functions of MSC, with enhanced effects on senescent cells [12]. The lack of an enhanced response to IFNγ priming indicates that cultured vBA-MSC retain full immunomodulatory capacity.

FIG. 19 shows representative flow plots for PBMCs alone, without and with PHA activation as well as PBMC and MSC after PHA activation are shown. Each data point represents the mean of 3 different experiments with 3 different donors (DD1, DD2 and DD3). Error bars represent the standard deviation. P>0.05 for comparisons at all PBMC:vBA-MSC ratios+/−IFN-y.

The immunophenotypic profile of plastic adherent vBA-MSC, trilineage differentiation capacity and CFU-F potential as well as immunomodulatory properties confirm the classification of these cells as MSC according to the International Society of Cell and Gene Therapy (ISCT) published guidance [28]. To further establish their equivalency to MSC obtained from BM, a comparison was performed between vBA-MSC and MSC isolated from central BM (FIG. 21). Both commercially available previously expanded live donor BM-MSC (Ex LD BM-MSC), obtained cryopreserved at passage 2, as well as MSC freshly isolated from live donor aspirated BM (LD BM-MSC) were used. In addition, MSC isolated from deceased donor VB BM (DD vBM-MSC) was also included in the comparison. MSC from three donors for each source were expanded to passage 2 and cryopreserved. Upon subsequent thawing, cells were passaged once prior to performing the analyses. MSC from all four sources demonstrated essentially identical immunophenotypic cell surface marker profiles, with very low numbers of cells that expressed CD14, CD19, CD34, CD45 and HLA-DR, and, conversely, nearly all cells expressed CD73, CD90 and CD105.

Surface marker expression of passage 3 cells was characterized by flow cytometry. The different sources of MSC were: deceased donor vBA-MSC (DD vBA-MSC); deceased donor vertebral body bone marrow-derived MSC (DD BM-MSC); living donor aspirated BM MSC (LD BM-MSC); and living donor aspirated BM MSC obtained from a commercial sources at passage 2 (LD Ex BM-MSC). There were no differences in surface marker expression between cell types. MSC from each source grew rapidly in culture through 5 passages (the longest period examined) with no differences in population doubling times (PDTs) at passages 4 and 5. Comparison of population doubling times (PDT) from passages 2 to 3, 3 to 4, and 4 to 5. LD Ex BM-MSC grew significantly (*, P<0.05) slower between passage 2 and 3 than either vBA-MSC and LD BM-MSC. No difference in PDT was observed in the subsequent 2 passages. CFU-F assays were performed as described in FIG. 18 for passaged cells. Formation of CFU-F was significantly lower (*, P<0.05) for passage 2 LD Ex BM-MSC compared to the other three sources of MSC, also at passage 2. Each bar represents the mean+sd from the 3 donors for each MSC source. The specific donors were: LD BM-MSC (donors LD1, LD2 and LD3); LD Ex BM-MSC (donors LD4, LD5 and LD6); vBM-MSC and vBA-MSC (donors DD1, DD2 and DD3). Donor characteristics are listed in Table 1.

Figure 20:
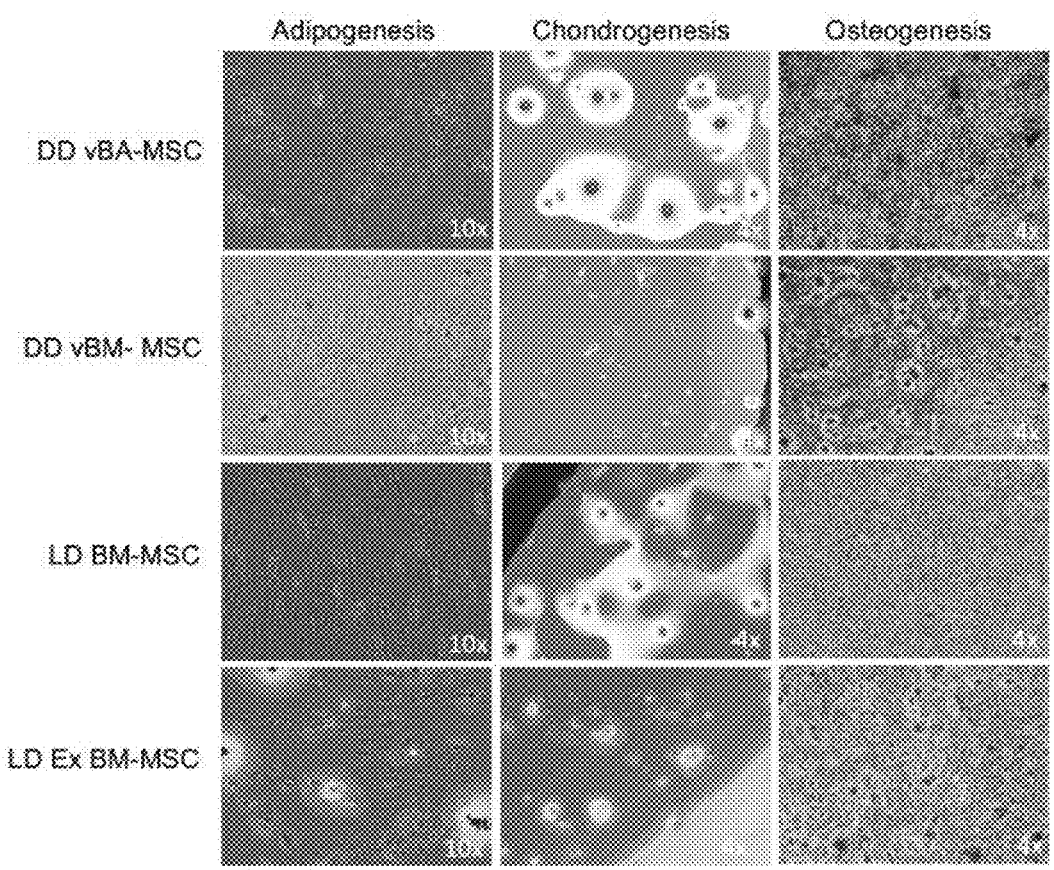
FIG. 20 shows trilineage differentiation of vBA-MSC and MSC isolated from deceased donor vertebral body BM and BM aspirated from the iliac crests of living donors.

Later passages were not compared for CFU-F potential. Finally, trilineage differentiation potentials were compared and it was found that each MSC population formed adipocytes, chrondrocytes and osteocytes in vitro at qualitatively the same frequencies (FIG. 20). Here, cells were culture and induced to undergo differentiation for each cell type as described in FIG. 17. There was no qualitative difference in either adipogenic, chondrogenic and osteogenic potential of passage 3 cells from any of the four sources. Images are representative from experiments with the 3 different donors for each source of MSC. Magnification is indicated for each image.

Figure 21A:
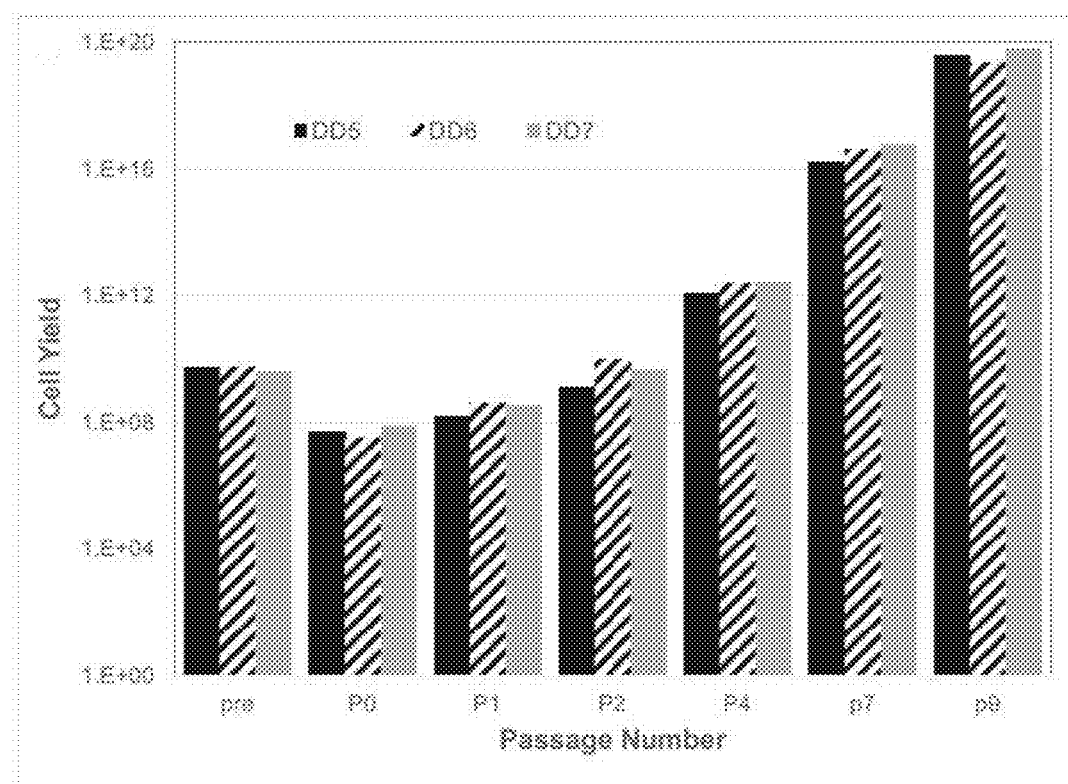
FIG. 21A shows the observed and potential cumulative growth yields at each passage of vBA-MSC from 3 donors and FIG. 21B shows the cumulative vBA-MSC population doublings at passages 0-9.

The potential clinical translational utility of vBA-MSC was assessed by performing a pilot-scale manufacturing run to examine feasibility of banking and expanding large numbers of cells from individual donors. Fragments of VB from 3 different donors (DD5, DD6 and DD7) were isolated, digested to isolate vBA-MSC, and expanded to passage 1 to form a master cell bank were. The amount (100 g) corresponds to approximately one-third of the total VB bone fragment weight obtainable from typical donors. A portion of the passage 1 vBA-MSC from each donor was expanded to passage 9. A MCB at passage 1 from each donor, containing an average of $2.9 \times 10^8 + 1.35 \times 10^8$ vBA-MSC, was prepared and the bulk cryopreserved, while the remainder was cultured over multiple passages, tracking total cell yields at each passage (FIG. 21A). Passage 1 was considered to be optimal for an MCB, displaying essentially the same surface maker profile and CFU-F potential as later passages (FIG. 17 and FIG. 18). A single further expansion to passage 2 was enough to produce an WCB containing $5.17 \times 10^9 + 4.3 \times 10^9$ vBA-MSC. Based on observed population doublings, two expansions of the entire WCB were sufficient to manufacture over a trillion cells. The PDT remained nearly constant between passages 2 and 9, without indications of diminishing growth rate at the upper passage number.

Figure 21B:
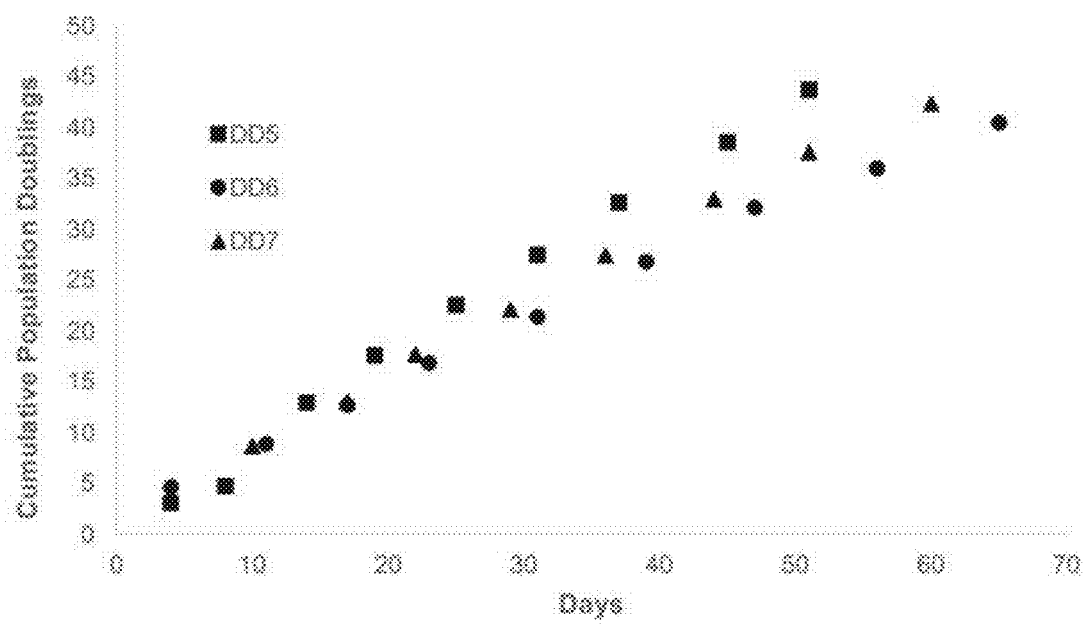

However, there were differences in PDTs between donors (FIG. 21B). Population doublings (PD) were calculated based on initial numbers of cells plated and the number recovered after each plate reached 80% confluency before re-plating the cells and was used to determine the theoretical total cell yield after each passage. Theoretical total yields at passages 2-9 were obtained by exponentiating (base 2) the PD calculated for each passage and multiplying by the cumulative cell number from each preceding passage. Each donor vBA-MSC was plated in triplicate for each passage. The coefficient of variation (CV) between cell numbers obtained from each well was <15%.

Based on the observed PDTs for each donor, starting with a seed stock of 2 million vBA-MSC, it would require 23, 36 and 29 days to manufacture one trillion cells from the three different donors. These times were calculated using 2-dimensional tissue culture flasks and would likely differ in bioreactors.

Discussion

The transformative potential of MSC to treat a wide variety of medical disorders has been idealized for over a decade; yet, despite many demonstrations of this potential in preclinical and early-stage clinical trials, no MSC-based therapies have achieved success in late-stage, registration (commonly Phase 3 in the U.S.) clinical trials, although a few have received approval for limited indications in relatively small jurisdictions. The reasons for the slow progress in approvals and resulting commercialization of therapeutic MSC despite intense development efforts by multiple entities is certainly multifactorial. In hindsight, it appears that attempts to manufacture MSC at large scale through adopting processes and procedures from the highly successful biopharmaceutical sector might have been a contributory factor [35, 36]. There are many differences between manufacturing products derived from cells versus the cells themselves. Biopharmaceuticals are produced using immortalized cell lines having the ability of nearly unlimited expansion, allowing the generation of large MCBs from a single seed stock. Conversely, the limited availability and expansion potential of MSC requires generating multiple MCB from different donors each year at a disproportionately higher manufacturing costs and regulatory burden [36].

We present here a viable solution to reducing these burdens through the identification and characterization of a large depot of MSC from deceased donor vertebral bones. Based on the analysis presented here, vBA-MSC are phenotypically and functionally equivalent to MSC obtained from central BM. The cells express typical MSC markers (CD73, CD90 and CD105) and lack expression of hematopoietic stem and progenitor cell markers as well as express very low levels of HLA class II proteins. Like BM-MSC, vBA-MSC possess the potential to clonally expand and can be induced to undergo trilineage differentiation. Passaged vBA-MSC are fully fit to suppress T cell activation, demonstrating no difference in activity with prior stimulation by IFNγ. The differences in PDT and CFU-F of passage 3 (but not later passages) expanded BM-MSC obtained from a commercial source most likely reflects a slower recovery from cryopreservation at passage 2. All MSC were grown to passage 2 and cryopreserved in an effort to maintain comparability; however, the commercial source of expanded BM-MSC were likely grown in a different medium and frozen in a different cryopreservation medium. Thus, the cells experienced a lag upon thaw and growth to passage 3 which was not evident in subsequent passages.

Cell bank sizes averaging $2.4 \times 10^8$ MSC were obtainable from 100 g of digested VB bone fragments from each of 3 donors. Each bank was expanded through a total of 9 passages without a significant reduction of population doubling time. The theoretical yield with full expansion of each donor through 9 passages was $4 \times 10^{19}$ (40 quintillion) cells, equating to over 500 billion doses at $10^6$/kg for an average 70 kg patient. Inevitably, actual total cell yields will be lower due to inefficiencies inherent in large scale manufacturing and requirements for testing; nonetheless, the COG for production of large batches from a single donor would likely be much less than for equivalent scales of manufacturing from multiple donors. The savings in direct manufacturing costs would be in addition to the reduced regulatory burden with using a single donor source for all manufacturing campaigns. The next step in validating the potential cost savings with vBA-MSC will be to perform scaled-up manufacturing runs, which are currently in progress.

We are presently exploring the question of why some populations of MSC are easily dislodged or possibly free floating in the BM, while others remain tightly adhered to the bone/connective tissue matrix and can only be liberated by enzymatic digestion. Determining differences, if they exist, is complicated by the relatively low frequency of these cells, making them problematic to characterize using common analytical tools, such as flow cytometry, without first expanding in culture, which induces phenotypic and functional alterations [37-45]. One previous report found that freshly isolated enzymatic digests of pelvic region trabecular bone contained 15-fold higher CFU-F than aspirated BM [24]; however, we did not find a similar difference between freshly isolated vBA-MSC and BM-MSC. To better understand dissimilarities, if any, between the populations, we are pursuing single cell RNA sequencing (scRNA-Seq) of vBA-MSC transcriptomes [46, 47]. We are also continuing to characterize the therapeutic potential of vBA-MSC by studying the secretome and extracellular vesicles produced by these cells.

In summary, based on the data presented here, the fundamental nature of vBA-MSC does not appear to differ from aspirated BM-MSC; therefore, these cells could potentially be seamlessly substituted for therapeutic applications at a significant savings in manufacturing and regulatory costs. Additionally, other markets requiring large numbers of MSC could also benefit from an abundant source of primary cells. These include tissue engineering and manufacture of products derived from MSC, such as exosomes, as well as biomedical research applications and the emerging applications of cosmeceuticals and bioengineered materials. Each of these markets is expected to grow substantially over the next decades, driving combined demand for MSC in excess of 10 sextillion ($1 \times 10^{21}$) cells annually by 2040 [2]. Future high demand for MSC across all these markets could be entirely met by vBA-MSC obtained from the abundant and steady supply of deceased donor medullary cavity containing bones from the 10,000 organ donors and a further 40,000 tissue donors each year in the U.S. alone.

TABLE 1

Description of donors used in Example 1

| DD1 | vBA-MSC, vBM-MSC | 22 | M | Caucasian |
| DD2 | vBA-MSC, vBM-MSC | 13 | M | Caucasian |
| DD3 | vBA-MSC | 35 | M | Hispanic |
| DD4 | vBA-MSC, vBM-MSC | 19 | M | Hispanic |
| DD5 | vBA-MSC | 17 | M | Caucasian |
| DD6 | vBA-MSC | 14 | M | Caucasian |
| DD7 | vBA-MSC | 23 | M | Caucasian |
| LD1 | LD BM-MSC | 20 | F | African American |
| LD2 | LD BM-MSC | 23 | F | African American |
| LD3 | LD BM-MSC | 28 | M | African American |
| LD4 | Ex LD BM-MSC | 24 | F | African American |
| LD5 | Ex LD BM-MSC | 36 | M | African American |
| LD6 | Ex LD BM-MSC | 25 | M | African American |

Abbreviations: DD, deceased donor; LD, live donor; BM, bone marrow

TABLE S1

Description of antibodies and dyes used

| Antibody | Fluorophore | Clone | Isotype | Source |
|---|---|---|---|---|
| CD3 | PE | UCHT1 | IgG1-PE | BD |
| CD14 | PE | MφP9 | IgG2b-PE | BD |
| CD19 | PE | 4G7 | IgG1-PE | BD |
| CD31 | PE | MBC78.2 | IgG1-PE | BD |
| CD34 | PE | 8G12 | IgG1-PE | BD |
| CD45 | APC | F10-89-4 | IgG2a-APC | Caprico |
| HLA-DR | APC | L243 | IgG2a-APC | Caprico |
| CD73 | PeCy7 | TY/11.8 | IgG1-PeCy7 | Biolegend |
| CD90 | FITC | F15-42-1 | IgG1-FITC | Caprico |
| CD105 | APC | 43A3 | IgG1-APC | Biolegend |
| Stro-1 | APC | STRO-1 | IgM-APC | ThermoFisher |
| 7AAD[1] | — | — | — | Invitrogen |

[1]Abbreviations: 7-AAD, 7-aminoactinomycin; PE, phycoerythrin; APC, allophycocyanin; PeCy7, phycoerythrin-cyanin 7; FITC, fluorescein isothiocyanate.

REFERENCES

1. Lipsitz, Y. Y., et al., *A roadmap for cost-of-goods planning to guide economic production of cell therapy products.* Cytotherapy, 2017. 19(12): p. 1383-1391.
2. Olsen, T. R., et al., *Peak MSC-Are We There Yet?* Front Med (Lausanne), 2018. 5: p. 178.
3. Pereira Chilimia, T. D., F. Moncaugeig, and S. S. Farid, *Impact of allogeneic stem cell manufacturing decisions on cost of godds, process robustness and reimbursement.* Biochemical Engineering Journal, 2018. 137: p. 132-151.
4. Simaria, A. S., et al., *Allogeneic cell therapy bioprocess economics and optimization: single-use cell expansion technologies.* Biotechnol Bioeng, 2014. 111(1): p. 69-83.
5. Harrison, R. P., N. Medcalf, and Q. A. Rafiq, *Cell therapy-processing economics: small-scale microfactories as a stepping stone toward large-scale macrofactories.* Regen Med, 2018. 13(2): p. 159-173.
6. Mizukami, A., et al., *Technologies for large-scale umbilical cord-derived MSC expansion: Experimental performance and cost of gooods analysis.* Biochemical Engineering Journal, 2018. 135: p. 36-48.
7. Pittenger, M. F., et al., *Multilineage potential of adult human mesenchymal stem cells.* Science, 1999. 284 (5411): p. 143-7.
8. Chilima, T. D. P., T. Bovy, and S. S. Farid, *Designing the optimal manufacturing strategy for an adherent allogeneic cell therapy.* BioProcess International, 2016. 14(9): p. 24-32.
9. Heathman, T. R., et al., *Characterization of human mesenchymal stem cells from multiple donors and the implications for large scale bioprocess development.* Biochemical Engineering Journal, 2016. 108: p. 14-23.
10. Lechanteur, C., et al., *Large-scale clinical expansion of mesenchymal stem cells in the GMP-compliant, closed automated Quantum® cell expansion system: Comparison with expansion in traditional T-flasks.* Stem Cell Research & Therapy, 2014. 4(8): p. 1-11.
11. Wuchter, P., et al., *Standardization of Good Manufacturing Practice-compliant production of bone marrow-derived human mesenchymal stromal cells for immunotherapeutic applications.* Cytotherapy, 2015. 17(2): p. 128-39.
12. Chinnadurai, R., et al., *Immune dysfunctionality of replicative senescent mesenchymal stromal cells is corrected by IFNgamma priming.* Blood Adv, 2017. 1(11): p. 628-643.
13. Mendicino, M., et al., *MSC-based product characterization for clinical trials: an FDA perspective.* Cell Stem Cell, 2014. 14(2): p. 141-5.
14. Lockhart, R. A., J. A. Aronowitz, and S. Dos-Anjos Vilaboa, *Use of Freshly Isolated Human Adipose Stromal Cells for Clinical Applications.* Aesthet Surg J, 2017. 37(suppl_3): p. S4-S8.
15. Dykstra, J. A., et al., *Concise Review: Fat and Furious: Harnessing the Full Potential of Adipose-Derived Stromal Vascular Fraction.* Stem Cells Transl Med, 2017. 6(4): p. 1096-1108.
16. Donnenberg, A. D., et al., *Clinical implementation of a procedure to prepare bone marrow cells from cadaveric vertebral bodies.* Regen Med, 2011. 6(6): p. 701-6.
17. Ahrens, N., et al., *Mesenchymal stem cell content of human vertebral bone marrow.* Transplantation, 2004. 78(6): p. 925-9.
18. Cox, G., et al., *High abundance of CD271(+) multipotential stromal cells (MSCs) in intramedullary cavities of long bones.* Bone, 2012. 50(2): p. 510-7.
19. Rybka, W. B., et al., *Hematopoietic progenitor cell content of vertebral body marrow used for combined solid organ and bone marrow transplantation.* Transplantation, 1995. 59(6): p. 871-4.
20. Soderdahl, G., et al., *Cadaveric bone marrow and spleen cells for transplantation.* Bone Marrow Transplant, 1998. 21(1): p. 79-84.
21. Blashki, D., et al., *Mesenchymal stem cells from cortical bone demonstrate increased clonal incidence, potency, and developmental capacity compared to their bone marrow-derived counterparts.* J Tissue Eng, 2016. 7: p. 2041731416661196.
22. Siclari, V. A., et al., *Mesenchymal progenitors residing close to the bone surface are functionally distinct from those in the central bone marrow.* Bone, 2013. 53(2): p. 575-86.
23. Yusop, N., et al., *Isolation and Characterisation of Mesenchymal Stem Cells from Rat Bone Marrow and the Endosteal Niche: A Comparative Study.* Stem Cells Int, 2018. 2018: p. 6869128.
24. Jones, E., et al., *Large-scale extraction and characterization of CD271+ multipotential stromal cells from trabecular bone in health and osteoarthritis: implications for bone regeneration strategies based on uncultured or minimally cultured multipotential stromal cells.* Arthritis Rheum, 2010. 62(7): p. 1944-54.
25. Gorantla, V. S., et al., *Development and validation of a procedure to isolate viable bone marrow cells from the vertebrae of cadaveric organ donors for composite organ grafting.* Cytotherapy, 2012. 14(1): p. 104-13.
26. Li, M., et al., *Therapeutic Delivery Specifications Identified Through Compartmental Analysis of a Mesenchymal Stromal Cell-Immune Reaction.* Sci Rep, 2018. 8(1): p. 6816.
27. Quah, B. J., H. S. Warren, and C. R. Parish, *Monitoring lymphocyte proliferation in vitro and in vivo with the intracellular fluorescent dye carboxyfluorescein diacetate succinimidyl ester.* Nat Protoc, 2007. 2(9): p. 2049-56.
28. Dominici, M., et al., *Minimal criteria for defining multipotent mesenchymal stromal cells. The International Society for Cellular Therapy position statement.* Cytotherapy, 2006. 8(4): p. 315-7.
29. Gronthos, S., et al., *Molecular and cellular characterisation of highly purified stromal stem cells derived from human bone marrow.* J Cell Sci, 2003. 116(Pt 9): p. 1827-35.
30. Simmons, P. J. and B. Torok-Storb, *Identification of stromal cell precursors in human bone marrow by a novel monoclonal antibody, STRO-1.* Blood, 1991. 78(1): p. 55-62.
31. Dennis, J. E., et al., *The STRO-1+ marrow cell population is multipotential.* Cells Tissues Organs, 2002. 170(2-3): p. 73-82.
32. Bensidhoum, M., et al., *Homing of in vitro expanded Stro-1− or Stro-1+ human mesenchymal stem cells into the NOD/SCID mouse and their role in supporting human CD34 cell engraftment.* Blood, 2004. 103(9): p. 3313-9.
33. Galipeau, J., et al., *International Society for Cellular Therapy perspective on immune functional assays for mesenchymal stromal cells as potency release criterion for advanced phase clinical trials.* Cytotherapy, 2016. 18(2): p. 151-9.
34. Squillaro, T., G. Peluso, and U. Galderisi, *Clinical Trials With Mesenchymal Stem Cells: An Update.* Cell Transplant, 2016. 25(5): p. 829-48.

35. Galipeau, J. and L. Sensebe, *Mesenchymal Stromal Cells: Clinical Challenges and Therapeutic Opportunities.* Cell Stem Cell, 2018. 22(6): p. 824-833.
36. Jossen, V., et al., *Manufacturing human mesenchymal stem cells at clinical scale: process and regulatory challenges.* Appl Microbiol Biotechnol, 2018. 102(9): p. 3981-3994.
37. Banfi, A., et al., *Replicative aging and gene expression in long-term cultures of human bone marrow stromal cells.* Tissue Eng, 2002. 8(6): p. 901-10.
38. Baxter, M. A., et al., *Study of telomere length reveals rapid aging of human marrow stromal cells following in vitro expansion.* Stem Cells, 2004. 22(5): p. 675-82.
39. Bork, S., et al., *DNA methylation pattern changes upon long-term culture and aging of human mesenchymal stromal cells.* Aging Cell, 2010. 9(1): p. 54-63.
40. Bruder, S. P., N. Jaiswal, and S. E. Haynesworth, *Growth kinetics, self-renewal, and the osteogenic potential of purified human mesenchymal stem cells during extensive subcultivation and following cryopreservation.* J Cell Biochem, 1997. 64(2): p. 278-94.
41. Digirolamo, C. M., et al., *Propagation and senescence of human marrow stromal cells in culture: a simple colony-forming assay identifies samples with the greatest potential to propagate and differentiate.* Br J Haematol, 1999. 107(2): p. 275-81.
42. Muraglia, A., R. Cancedda, and R. Quarto, *Clonal mesenchymal progenitors from human bone marrow differentiate in vitro according to a hierarchical model.* J Cell Sci, 2000. 113 (Pt 7): p. 1161-6.
43. Redaelli, S., et al., *From cytogenomic to epigenomic profiles: monitoring the biologic behavior of in vitro cultured human bone marrow mesenchymal stem cells.* Stem Cell Res Ther, 2012. 3(6): p. 47.
44. Moravcikova, E., et al., *Proteomic Profiling of Native Unpassaged and Culture-Expanded Mesenchymal Stromal Cells (MSC).* Cytometry A, 2018. 93(9): p. 894-904.
45. Bara, J. J., et al., *Concise review: Bone marrow-derived mesenchymal stem cells change phenotype following in vitro culture: implications for basic research and the clinic.* Stem Cells, 2014. 32(7): p. 1713-23.
46. Choi, Y. H. and J. K. Kim, *Dissecting Cellular Heterogeneity Using Single-Cell RNA Sequencing.* Mol Cells, 2019. 42(3): p. 189-199.
47. Hwang, B., J. H. Lee, and D. Bang, *Single-cell RNA sequencing technologies and bioinformatics pipelines.* Exp Mol Med, 2018. 50(8): p. 96.

Example 2: The Relationships of Ischemia Time and Whole-Body Cooling to the Quality of Hematopoietic Stem and Progenitor Cells Recovered from the Bone Marrow of Deceased Organ Donors Deceased organ donors represent an untapped source of therapeutic bone marrow (BM), which can be recovered in 3-5 times the volume of that obtained from living donors, tested for quality, cryopreserved, and banked indefinitely for future on-demand use. However, a challenge for a future BM banking system built to a genetically diverse scale will be to manage the prolonged ischemia times that inevitably occur when bones procured at geographically-dispersed locations are shipped to distant facilities for processing. The goals of this study were: (a) to quantify, under realistic and scaled procurement and shipping conditions, the relationship between ischemia time and the quality of hematopoietic stem and progenitor cells (HSPCs) derived from deceased-donor BM; (b) to identify ischemia-time boundaries beyond which HSPC quality is adversely affected, and (c) to investigate whole-body cooling as a tactic for preserving cell viability and function. Bones were analyzed from 62 deceased donors following exposure to various periods of warm ischemia time (WIT), cold ischemia time (CIT) and body cooling time (BCT). Regression models were developed to quantify the independent associations of WIT, CIT and BCT in relation to the viability and function of recovered HSPCs. Results demonstrate that under "real-world" scenarios: (a) combinations of warm and cold ischemia times favorable to the recovery of high-quality HSPCs are readily achievable (e.g., CD34+ viabilities in the range of 80-90% were commonly observed); (b) cooling the body prior to bone recovery is detrimental to cell viability (e.g., CD34+ viability <73% with, vs. >89% without, body cooling); and (c) vertebral bodies (VBs) are a superior source of HSPCs compared to ilia (IL) (e.g., % CD34+ viability >80% when VBs were the source vs. <74% when IL were the source). Our quantitative models can be used to formulate ischemia-time tolerance limits and HSPC quality-acceptance criteria, and to inform an emerging BM banking system seeking to institute data-driven industry standards.

INTRODUCTION

Deceased-donor bone marrow (BM) represents a large, untapped source of hematopoietic stem and progenitor cells (HSPCs) that could be cryopreserved and banked for future on-demand use in bone marrow transplant (BMT) procedures. The appeal of BM banking is based in part on the recognition that HSPCs could be immediately available during surges in demand as, for example, following a mass casualty event such as a nuclear disaster resulting in widespread bone-marrow failure [1, 2]. Interest has been further solidified by recent successes with inducing durable or operational immune tolerance through infusing donor BM cells to establish transient mixed chimerism and/or peripheral immunomodulation in recipients of solid organ and vascular composite allograft (VCA) transplants [3-5]. A bank of BM from deceased organ donors establishes a repository for future tolerance induction procedures using delayed protocols which have been successful in non-human primates [6, 7].

Cryopreservation and banking of BM from deceased organ donors will require the establishment of BM banks similar in concept to umbilical cord blood banks. As with cord blood, it is well-established that BM remains biologically functional following cryopreservation and can serve as a genetically diverse, on-demand source of stem cell grafts [8-11]. Importantly, the national Organ Procurement Organization (OPO) network, which has been active in the United States (US) for over 50 years, provides an existing, well-functioning infrastructure for procuring and transporting bone tissue recovered from deceased donors. However, organizing an organ-donor BM procurement and banking system that capitalizes on existing OPO infrastructure will require coordinated efforts involving the recovery and safe shipment of biological material to specialized BM cell-processing centers appropriately scaled for clinical production.

A critical issue, which typically has not been viewed as significant in the case of living BM donors, is the ischemia time that inevitably is introduced during recovery and shipment of bones recovered from deceased donors. Before a clinical production system can be brought to scale, it will be necessary to determine how variations in warm- and cold-ischemia times influence the quality of HSPCs derived from bones recovered at geographically dispersed locations and shipped long distances to centralized processing facilities. And it will be necessary to establish upper tolerance limits for both warm- and cold-ischemia, which, if exceeded, would likely render the quality and functionality of HSPCs unacceptable for therapeutic use.

Additionally, the impact of whole-body cooling in the context of deceased-donor bone recovery and shipment needs to be better understood. Current tissue-banking guidelines in the US allow tissues to be recovered from deceased donors up to 24 hours following asystole, provided the body is refrigerated within 12 hours of cardiac arrest [12]. However, body cooling is a variable that has not been investigated systematically in relation to the recovery of BM, and it is one that may require different criteria than those established for tissue recovery.

Here we present our results for the first time, which quantify the associations of ischemia time and whole-body cooling with the quality of HSPCs recovered from cadaveric vertebral bones. Our analyses show that high-quality, functional HSPCs can be obtained from deceased donors even after recovered bones are subjected to cumulative warm- and cold-ischemia times exceeding 40 hours, provided that body cooling, which is shown to be detrimental to viability, is avoided. These findings should be useful in establishing warm- and cold-ischemia-time tolerance limits and HSPC quality acceptance standards for BM derived from deceased organ donors.

Methods

Study Design

This is a pragmatic observational field study designed to model the effects of ischemia and body-cooling times on the viability and function of HSPCs recovered from the BM of deceased organ donors [13]. The study was designed to produce observations that can be generalized and applied in routine practice settings. The study's external validity (generalizability) was enhanced by securing the participation of multiple OPOs operating under normal field conditions. Except for special training related to the details of bone recovery and shipment (see below), usual procurement conditions were in effect. Because the OPOs were geographically dispersed, the collected data cover the full spectrum of ischemia times likely to be seen under "real-world" procurement and shipping scenarios.

Donor Tissue Procurement and Transport

Previously developed clinical recovery methods combined with subsequent experience in the ongoing VCA transplant immune tolerance clinical trial at Johns Hopkins University (ClinicalTrials.gov Identifier: NCT01459107) formed the basis for the procurement and transport protocols [4, 14-16]. However, these protocols required optimization and validation to ensure that multiple OPOs could reliably operationalize them in a manner that allowed for the production of consistent yields of functionally viable HSPCs after recovery and transport of bones across a broad geography. To that end, a streamlined OPO recovery procedure, combined with dedicated kits and centralized training on recovery and shipment procedures were employed.

Recovered bones were shipped to one of two processing facilities located in Centennial, Colo. (Facility A) or Indianapolis, Ind. (Facility B). Vertebral sections (Facility A and B) and/or ilia (Facility A, only) were procured by six OPOs: Gift of Hope (Itasca, Ill.); Donor Alliance (Denver, Colo.); Iowa Donor Network (North Liberty, Iowa); Mid America Transplant (St. Louis, Mo.); and Nevada Donor Network (Las Vegas, Nev.). Bones were recovered by OPO personnel using an osteotome and mallet under an IRB approved protocol from research-consented organ and tissue donors. Unprocessed bones were wrapped in lap sponges and towels soaked in saline and placed in triple-sealed bags to ensure moisture retention during shipment. Wrapped specimens were shipped overnight on wet ice to one of the two processing facilities.

Manual Debriding

Upon receipt, in an ISO 5 clean room (Facility A) or a Biological Safety Cabinet (Facility B), soft tissue was manually debrided using scalpels and gouges. Once visible, the pedicles were removed using either a tissue processing band saw or a Stryker System 6 Saw (Stryker, Kalamazoo, Mich.) leaving only the connected vertebral bodies. Using a boning knife (Facility B) or tissue processing band saw (Facility A), vertebral bodies were separated at the intervertebral disc. Remaining intervertebral disc and soft tissue was removed with a scalpel, leaving clean, separated VBs. Ilium soft tissue was removed with gouges and a scalpel. Care was taken to ensure that the cortical bone was not breached to preserve and protect the hypoxic cancellous BM throughout the entire debriding process.

Using a saw and/or anvil shears, VBs and ilium were cut into 5 $cm^3$ pieces small enough for fragmenting with a bone grinder. The pieces were immediately submerged into 500 mL processing medium (Iscove's Modified Dulbecco's Medium containing 100 U/mL DNase™, 10 U/mL heparin, and 2.5% human serum albumin). IMDM is suitable for rapidly proliferating high-density cell cultures and ideal for supporting T- and B-lymphocytes. DNase™ is essential for the mitigation of cell clumping as a result of DNA release from dying cells and post-mortem stress on deceased donor derived BM. Heparin was used as an anticoagulant. HSA provided a protein source to prevent cell adherence and adsorption to surfaces.

Grinding and Elution

An electric bone grinder was assembled in an ISO-5 cleanroom (Facility A), and a purpose-built bone grinder (Biorep Technologies Inc., Miami, Fla.) was assembled in a Biological Safety Cabinet (Facility B). In either facility, a 2 L stainless steel beaker containing 100 mL of fresh processing medium was placed under the grinding head to catch bone fragments and media flow-through. Bone types were kept separate if both VB and IL from the same donor were processed. Processing medium was used to rinse the grinder throughout the process to prevent bone from drying and sticking to the chamber. Once all bone pieces were ground, the chamber was thoroughly rinsed with fresh processing media. The final volume in the stainless-steel beaker was typically around 750 mL Stainless steel sieves were stacked with a No. 40 (425 µm) on top of a No. 80 (177 µm) and seated over a round catch-pan (WS Tyler, St. Catherines, ON). The stainless-steel beaker was swirled and poured over the sieves. Bone fragments were distributed evenly on top of the sieve and rinsed with 250 mL of fresh processing medium. The sieved BM product, approximately 1000 mL, was transferred to a sterile pack for final analysis.

Nucleated Cell Counts

An aliquot of BM extract was subjected to red blood cell lysis with ammonium chloride RBC lysis buffer. In a 15 mL conical tube, 4 mL of 9% ammonium chloride was added to 1 mL of BM cell suspension and incubated for 5 minutes at room temperature. Following incubation, the lysed sample was filled to the top of the tube with IMDM containing 100 U/mL DNase™, 10 U/mL heparin, and 2.5% HSA processing medium. The lysed sample was centrifuged at 300×g for 5 minutes and decanted. The sample was then washed with 15 mL of processing medium, centrifuged at 300×g for 5 minutes, and decanted. Finally, the lysed cells were re-suspended with 1 mL of the same processing medium. Viable nucleated cell counts were obtained using Trypan blue and a hemocytometer.

Flow Cytometry

Flow Cytometry was performed using an ACEA Biosciences NovoCyte 2060R equipped with 488 nm and 640 nm lasers. ISHAGE methods were used to enumerate CD45+ and CD34+ cells [16]. 500 µL of lysed bone marrow extract was stained for 15 minutes with 2 µL each of CD45-FITC, CD34-APC, 7-AAD, and Annexin-PE. All conjugated antibodies were purchased from BD Biosciences and 7-AAD was obtained from Tonbo Biosciences. Cells were also stained with individual conjugate antibodies for controls and compensation. After incubating for 15 minutes, cells were washed with Dulbecco's phosphate buffered saline, centrifuged, and re-suspended in 500 µL of PBS. These samples were run directly on the flow cytometer and analyzed using the ISHAGE gating scheme [16] For each sample 100,000 total events gated on the Singlets gate were collected.

Colony Forming Unit (CFU) Assay

The concentration of RBC lysed cell suspension was first adjusted to $10^5$ viable cells/mL with processing medium before adding 250 µL to 2.5 mL of semisolid medium, METHOCULT™ Optimum (Stem Cell Technologies, Vancouver, Canada) and then vigorously vortexed to achieve adequate mixing. A 3 cc syringe was used to remove at least 2.2 mL of METHOCULT™ containing cells. 1.1 mL was dispensed into each of two 35 mm non-tissue culture treated dishes. The dishes were covered and tilted to ensure coating of entire plate surface with METHOCULT™. The two dishes were placed inside a larger 100 mm petri dish with a third uncovered 35 mm dish containing sterile DI water to humidify the plate. Plates were incubated for 14 days at 37° C., 5% CO2 before scoring colonies.

Numbers of Donors and Bone Marrow Samples Utilized for Statistical Modeling

Seventy-five bones from 62 donors were initially received at one of the two BM processing facilities. The numbers of samples with complete data records differed depending on the outcome being modeled. Table 1 provides a breakdown of the numbers received and the numbers with complete data available for statistical modeling by outcome.

TABLE 2

Numbers of donors and bones available for analysis by outcome
Total with Complete Data for Analysis:

| Modeled Outcome | Donors | Bones | VB | IL |
| --- | --- | --- | --- | --- |
| %CD34+ | 62 | 75 | 52 | 23 |
| CFU-TOTAL/$10^5$ | 54 | 67 | 42 | 25 |
| CFU-GM $10^5$ | 54 | 66 | 41 | 25 |

Definition of Ischemia Time

Total ischemia was defined as the interval from time of death (when the donor's arterial system was cross-clamped and circulation ceased) to start of BM recovery at the processing facility. For purposes of statistical modeling, this total interval was separated into three successive and mutually exclusive time components: (a) Warm Ischemia Time (WIT): Beginning at time of death and ending either when bones were recovered and packed on ice or when the body was placed in a cooler. (b) Body Cooling Time (BCT): Beginning when the body was placed in the cooler and ending when recovered bones were packed on ice. (c) Cold Ischemia Time (CIT): Beginning when recovered bones were packed on ice and ending when processing began for extraction of HSPCs. By these definitions, Total Ischemia Time=(WIT)+(BCT)+(CIT). When body cooling was not used BCT was coded zero and Total Ischemia Time=(WIT)+(CIT). Ischemia times were considered the main variables of interest in predictive outcome models.

Definition of Experience

Because this was the first series in our hands in which BM was processed from cadaveric bone, we hypothesized that HSPC quality might improve with learning as we gained more processing experience. This hypothesis rests on long-established research demonstrating that learning curves exert significant effects on outcomes and costs in both industrial manufacturing [17] and medical practice settings [18-20]. To control for learning, we created a variable, EXPERIENCE, defined as the number of donors processed prior to the current one. For the $i^{th}$ donor, EXPERIENCE was coded i −1, to indicate that EXPERIENCE is always one less than the serial number of the current case being processed. Because Facility A began processing BM five months before Facility B, and because Facility B had the advantage of participating in and learning from cases processed at Facility A, we hypothesized that the two facilities would have different learning trajectories. To account for this possible difference, each facility's experience was coded separately. To identify the facilities in the model, we coded Facility A=1 and Facility B=0. The effect of EXPERIENCE was initially estimated in separate regression models and subsequently incorporated as a covariate in final adjusted models to control for the effect of learning on outcomes.

Other Covariates

Other variables tested in statistical models were: (1) BONE TYPE, vertebral bodies (VB) and ilia (IL), (representing the two sources of BM cells, coded VB=1; IL=0); DONOR SEX (percent male); and DONOR AGE (years). These additional covariates were treated as exogenous factors and were included in final models only if they were statistically significant or they improved the model's performance.

Outcome Variables

Outcomes were defined according to three quality measures as hallmarks of potential in vivo utility: (a) The proportion of recovered CD34+ cells that were viable (% CD34+) as determined by 7-AAD, (b) The total number of colony forming units (CFUs) per 105 total nucleated cells (TNC) plated (CFU-TOTAL), and (c) The number of CFU granulocyte-macrophages detected per 105 nucleated cells (CFU-GM).

Summary Statistics

Donor and processing-facility characteristics, ischemia times, and outcome measures were summarized as means or percentages as appropriate. Crude (unadjusted) comparisons were made between FACILITIES (A vs. B), BONE TYPE (VB vs. IL), and BODY COOLING (Yes or No) using independent-groups t-Tests or z-tests for proportions.

Statistical Modeling

The associations of ischemia times with outcomes were initially investigated in unadjusted regression models using only ischemia times as predictors. Additional models were then estimated to determine the separate associations of EXPERIENCE with outcomes. Finally, the effects of ischemia were evaluated in multivariable models that controlled for the potential influences of FACILITY, EXPERIENCE, BONE TYPE, DONOR SEX, and DONOR AGE. Separate models were estimated for each of the three outcomes of interest (% CD34+, CFU-TOTAL, and CFU-GM).

Ordinary least-squares (OLS) linear regression was employed to test a range of candidate models, including models incorporating two-way interactions, as well as logarithmic and second-order polynomial terms. From these candidates, the best reduced models were selected based on the following criteria. (a) Models with the greatest explanatory power (highest $R^2$ values) were favored. (b) Parsimonious models that explained the greatest percentage of variation with the fewest predictors were favored. The adjusted $R^2$, which guards against over-specification by penalizing models containing greater numbers of predictors [21], was used as a comparative indicator of explanatory power in selecting the most parsimonious models. Models that achieved the highest $R^2$ values while simultaneously maintaining or increasing the adjusted $R^2$ were favored. (c) Models with greater precision, as indicated by relatively smaller standard errors associated with both the model and model coefficients were favored. (d) Models with the best fit, as judged by an assessment of residual plots, were favored. Residuals were plotted and examined visually for discernable patterns, and confirmed quantitatively by regressing residuals onto observed values to uncover possible interactions or underlying curvilinear relationships. Because % CD34+ is a proportion limited to the closed unit interval, $[0 \leq (\% \text{ CD34+}) \leq 1]$, we found that traditional OLS linear regression produced unrealistic fitted values exceeding these interval boundaries. To correct for this, we substituted beta regression for linear regression in models of % CD34+[22]. Beta regression is useful in situations where the response variable is a rate or proportion measured on a continuous scale and bounded by minimum and maximum values. We modeled a transformed variable, $pCD34^* = [100 \times (\% \text{ CD34+})+1]/102$, which satisfies the distributional assumption of beta regression that the outcome variable must be restricted to the open interval, $[0 < (\% \text{ CD34+}) < 1]$. So that predicted values could be reported in their original percentage units, beta regression results were back transformed to obtain:

Pred(% $CD34+$)=[102×(Pred($pCD34^*$))−1/100]

(A technical description of the beta regression model may be found in the below Technical Appendix A).

Model Validation

All models were validated using leave-one-out bootstrap cross-validation [23], accomplished by randomly omitting one observation with replacement from the dataset and re-estimating the model from the remaining observations. The resulting model was then used to predict the omitted observation. This procedure was repeated 200 times, yielding 200 models with predicted values, model coefficients, standard errors and 95% confidence intervals. Model parameters were summarized as averages of the 200 bootstrapped models. Since bootstrap models are naïve to the omitted observations, this form of validation serves as an estimate of the predictive accuracy likely to be seen when the original model is used to predict new observations [21]. Model coefficients are reported for the original models and compared with averaged coefficients+95% confidence intervals from the 200 cross-validated models.

Results

Figures 22, 23:
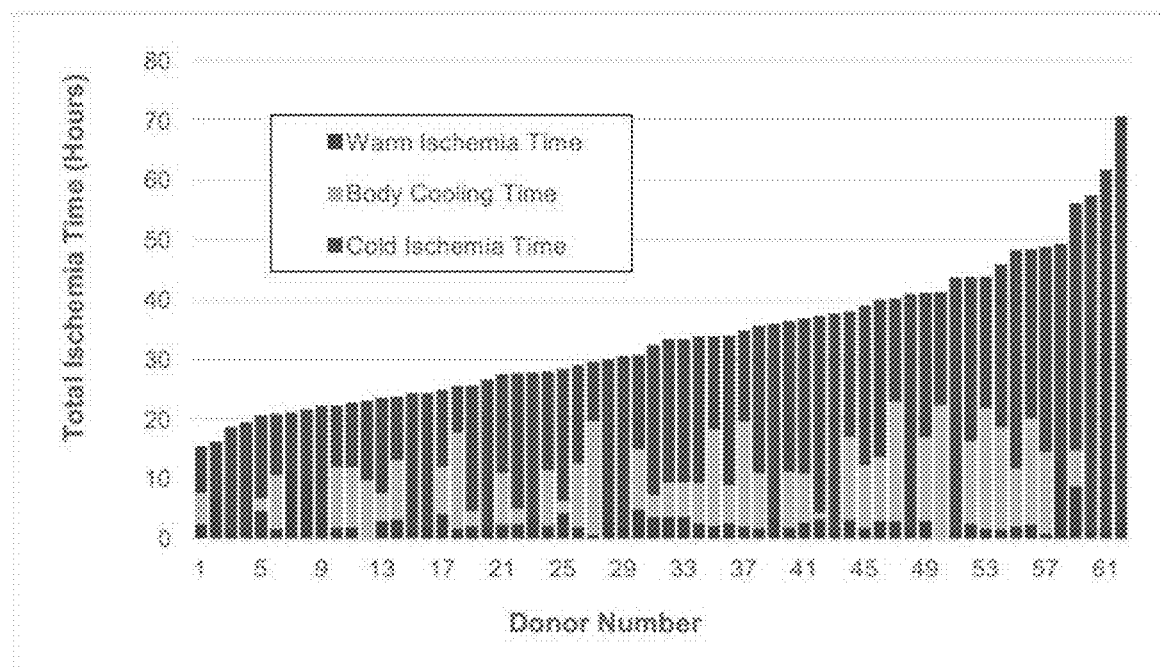
FIG. 22 shows the cumulative ischemia times for all donors used in the study of Example 2 for which complete data were available. Donors are ranked from shortest to longest total ischemia times which is a composite of WIT, CIT and BCT.
FIG. 23 is a table showing a comparison of (a) Processing Facility, (b) Bone Type, and (c) Body Cooling.

Sample characteristics are provided in Table 2 and the distribution of total ischemia times as well as individual ischemia-time components WIT, CIT and body cooling (BCT) for each of the 62 donors are shown in FIG. 22. The majority of donors (77.2%) were male. Average donor age was 41.2 years. Mean ischemia times in hours (+standard errors) were 3.6+0.4 for WIT, 7.9+0.9 for BCT, and 19.6+1.2 for CIT. The mean total ischemia time was 31.0+1.2 hours. An average of 2.43+0.64% CD45dim CD34+ HSPC were recovered from the BM specimens, of which an average 79.3+3.0% were viable cells. BM contained an average 250.3+49.48 CFU-Total per $10^5$ total nucleated cells (TNC) plated and 38.2+7.78 CFU-GM per $10^5$ TNC plated.

TABLE 3

Sample characteristics. Numbers are those associated with the %CD34+ model.

| | Mean/Percent | + Std Error | Min | Max |
|---|---|---|---|---|
| Bone Type (% Vertebrae) | 65.2% | 5.32% | — | — |
| Donor Sex (% Male) | 77.2% | 0.54% | — | — |
| Donor Age (yrs) | 41.2 | 1.6 | 13 | 64 |
| Experience* | 26.9 | 1.2 | 0 | 53 |
| Warm Ischemia (hrs) | 3.6 | 0.4 | 0.05 | 13.4 |
| Body Cooling (hrs) | 7.9 | 0.9 | 0 | 22.5 |
| Cold Ischemia (hrs) | 19.6 | 1.2 | 7.4 | 67.8 |
| Total Ischemia (hrs) | 31.0 | 1.2 | 15.3 | 70.5 |
| Outcomes | | | | |
| %CD34+ viability (n = 75) | 79.3% | 3.0% | 15.1% | 100% |
| CFU-TOTAL/$10^5$ cells (n = 67) | 250.3 | 49.5 | 0 | 1,850 |
| CFU-GM/$10^5$ cells (n = 66) | 38.2 | 7.8 | 0 | 282 |

*Average number of cases processed prior to the current case

Unadjusted Comparisons

Comparisons of FACILITY, BONE TYPE, and BODY COOLING are displayed in FIG. 23. The distributions of donor age and donor sex did not differ significantly by FACILITY, BONE TYPE, or whether BODY COOLING was used.

Facilities differed significantly in the distribution of BONE TYPE (VB comprised 27% of the bones processed at Facility A versus 100% at Facility B), which occurred because Facility B was structured to receive VBs only. Facility A also had more experience (Facility A=53 bones processed vs. Facility B=24 bones processed; p<0.00001), significantly longer WITs (Facility A=3.55 hours vs. Facility B=2.13 hours; p=0.003), and significantly shorter CITs (Facility A=19.55 hours vs. Facility B=28.38 hours; p=0.004). The two facilities did not differ in either BCT or total ischemia time. Outcomes differed only for CFU-GM counts, with Facility A having significantly lower counts than Facility B (28.38 vs. 64.31, respectively; p=0.04). The two facilities did not differ significantly in the percentage of viable CD34+ or CFU-TOTAL. Facility differences were controlled in final regression models.

Differences in BCT by BONE TYPE (middle section of FIG. 23) approached significance (p=0.09), with the processing of VBs associated with shorter BCTs (6.32 hours) compared to IL (8.51 hours). This occurred because Facility B, which processed only VBs, had shorter BCTs than Facility A. Outcomes also differed by BONE TYPE. Compared to IL, VBs yielded higher numbers of CFU-TOTAL (341.29 vs. 97.44 per $10^5$ cells, respectively; p=0.02) and CFU-GM (50.46 vs. 18.03 per $10^5$ cells, respectively; p=0.04). BONE TYPE was controlled in final regression models.

In cases where the body was refrigerated prior to bone recovery (right most section of FIG. 23), mean WITs tended to be significantly shorter (2.65 hours with, vs. 3.98 hours without, body cooling, p=0.04). The same was true for CITs (19.51 hours with, vs. 28.83 hours without, body cooling, p=0.009). It is noteworthy that all outcomes were worse when body cooling was employed. Mean % CD34+ viability was 72.75% with, vs. 89.86% without, body cooling (p=0.0001). Similarly, with and without body cooling the average CFU-TOTAL count was 100.16 vs. 659.00 per 105 TNC plated, respectively (p=<0.00001), and the average CFU-GM count was 18.52 vs. 94.85 per $10^5$ TNC plated, respectively (p<0.00001). BODY COOLING was accounted for in both initial and final ischemia-time regression models.

Ischemia-Time Regression Models

Unadjusted (base) regression models used only WIT, BCT, and CIT as predictors (no adjustments for other covariates). These models are summarized in the below Technical Appendix C, FIG. 27 to FIG. 29. Since BONE TYPE, FACILITY and EXPERIENCE were found to be significant variables associated with outcomes (FIG. 23), adjusted models were developed to control statistically for the influence of these covariates.

The beta regression model predicting % CD34+ viability is shown in FIG. 24. (Details of beta regression are provided in the below Technical Appendix A). The percentage of viable CD34+ cells that were recovered, declined significantly as a function of increasing BCT, with the decline occurring at a diminishing rate as % CD34+ approached zero (linear effect, p=0.002; second-order polynomial effect, p=0.03). A similar curvilinear decline in % CD34+ occurred in relation to increasing CIT (linear effect, p=0.003; second-order polynomial effect, p=0.005). Neither BONE TYPE nor WIT were significant. EXPERIENCE (p=0.09) and the FACILITY×EXPERIENCE interaction (p=0.07) approached statistical significance. Odds ratios measure the change in % CD34+ associated with a one-unit change in the associated predictor variable. For example, the odds ratio associated with a one-hour increase in WIT is 0.9663, indicating that each one-hour increase in WIT reduces % CD34+ to 96.63% of its previous value. The model's predictive validity is evidenced by the similarity of the estimated parameters of the original model (left panel of FIG. 24) to those of the bootstrap models (right panel). The model is statistically significant (p=0.001).

Results of the linear regression of CFU-TOTAL is shown in FIG. 25. Here the importance of BONE TYPE as a source of BM cells is revealed. When BM cells were recovered from VB rather than IL, CFU-TOTAL increased by 207/105 TNC plated (p=0.025). The effect of BCT on CFU-TOTAL was negative. As BCT increased, the recovery of CFU-TOTAL decreased, with the decline occurring at a diminishing rate (linear effect, p=0.00005; second-order polynomial effect, p=0.002). The effects of WIT and CIT were not statistically significant. EXPERIENCE also was not significant, however, EXPERIENCE was retained because model performance improved when EXPERIENCE was controlled statistically. When BONE TYPE and EXPERIENCE were both controlled statistically, the model's explanatory power improved from $R^2$=35% to 47%. The adjusted $R^2$ also improved from 35% to 40%, indicating that the improvement was not the result of model over-specification. Model precision also improved, as indicated by smaller standard errors. The similarity of the estimated parameters of the original model (left panel of FIG. 25) to the averaged results of the bootstrap models (right panel) is evidence of the model's predictive validity. The model was significant (p=0.000005) and explained 47.3% of the variation in CFU-TOTAL.

Results of the linear regression of CFU-GM are shown in FIG. 26. The best CFU-GM model included BONE TYPE, but not EXPERIENCE or FACILITY, as control variables. Although BONE TYPE was not statistically significant, it was retained in the model because its inclusion improved the explanatory power from $R^2$=32% to 34%, while the adjusted $R^2$ remained the same (29%), suggesting the model is not over-specified. With BONE TYPE controlled statistically, WIT and BCT continue to demonstrate statistically significant associations with CFU-GM. Each passing hour of WIT reduces CFU-GM by $-7.19/10^5$ TNC plated (p=0.03), while each hour of BCT reduces CFU-GM by $-5.24/10^5$ TNC plated (p=0.00003). CIT had no effect (p=0.86). The model's predictive validity is evidenced by the similarity in the parameters of the original model (left panel of FIG. 26) to the averaged results of the bootstrap models (right panel). The model is significant (p<0.00001) and explains just under 34% of the variability in CFU-GM.

Predictions from % CD34+ Model

A range of predictions generated from the adjusted beta regression model of FIG. 24 are shown in FIG. 15. The pattern of predictions illustrate how various combinations of WIT and CIT alter the viability of recovered CD34+ cells. The predictions in FIG. 15 are the outcomes expected when body cooling is not employed. Calculated values in each square represent the percentage of viable CD34+ cells recovered from whole BM. The gradient of shading demonstrates the overall interrelationship between WIT and CIT. The dense shading extending from the top left until the lightly-shaded region or until the unshaded region and comprising numbers greater than or equal to 80% represents values above 80% viability; the dense shading extending from bottom right towards the unshaded region, including the lightly-shaded region and unshaded region, and comprising numbers below or equal to 79% represents values below the 80% viability threshold. Input values used in the beta regression model to calculate CD34+ viability predictions were as follows: BCT=0 hours (no body cooling); Facility B=0 (Indianapolis); Experience=12 (mean for Indianapolis); Bone Type VB=0. WIT and CIT values are varied from the $10^{th}$ to $90^{th}$ percentile of observed values.

An inspection of the range of WIT and CIT values reveals that WIT is more detrimental to cell viability than CIT. When WIT is held to 3 hours or less, the viability of CD34+ cells remains at or above 80% (green region) for up to 24 hours of CIT. However, as WIT is extended beyond 3 hours the amount of CIT that can be tolerated is progressively shortened. We did not test the effect of cryopreservation, therefore these predicted values do not account for possible loss of viability due to subsequent freezing and thawing of recovered cells. Similar predictions for CFU-TOTAL and CFU-GM can be made using the coefficients provided in FIG. 25 and FIG. 26.

Discussion

In terms of total numbers of donors and number of bones procured, this pragmatic observational field study is the largest to date and the first to quantify the influences of ischemia and body-cooling times on the quality of HSPCs recovered from the bones of deceased donors. The study was designed with the intent of producing externally valid data that can be generalized and applied in routine practice settings. The study encompassed the full continuum of ischemia times likely to be seen under normal OPO operating conditions, and differed from previous studies conducted at single institutions where donor bones were recovered immediately after cardiac arrest (i.e., no body cooling), with rapid bone recovery (i.e., short WIT), and without the need for long periods of transport (i.e., reduced CIT) [4, 14, 15].

The study had three primary objectives: (a) to quantify the statistical relationships between ischemia time and the quality of HSPCs derived from deceased donors, (b) to determine the boundary conditions beyond which longer ischemia times adversely affect the quality of HSPCs, and (c) to investigate whole-body cooling as a tactic for preserving cell function and viability. The study results convey four principal messages.

First, acceptable levels of HSPC quality are achievable despite the prolonged ischemia times that are inevitable when bones must be procured by geographically dispersed OPOs and shipped cross-country to a distant processing center. Our analyses show that, under such conditions, favorable combinations of warm- and cold-ischemia times are readily achievable, enabling CD34+ cell viabilities in the range of 80-90%. Overall, the unadjusted mean percentage of viable CD34+ cells recovered was just under 80% (79.3%, Table 2).

The second message is that refrigerating the body prior to bone recovery, a practice that is common in the recovery of tissues, is detrimental to the viability and function HSPCs recovered from cadaveric BM. When whole-body cooling was used, CD34+ cell viability averaged 72.75%; when body cooling was not used, average viability reached nearly 90% (89.96%, Table 3), suggesting that the optimal practice would be to dispense with body cooling and transfer recovered bone as quickly as possible to a cold ischemic environment.

Third, the source of BM (bone type) matters. Our analysis shows that VBs are a superior source of viable HSPCs compared to IL. In unadjusted comparisons, CD34+ cell viabilities exceeded 80% when VB was the source, but fell below 74% when IL was the source (Table 3). The reason for this difference is not clear and is probably multifaceted. It is likely that variation in the isolation processes used with the two bone types was a more important factor than physiological differences. Given that this is the first study to compare BM from deceased donor VBs and IL, no other directly comparable data exist. The closest approximation is comparisons of the viability of CD34+ cells recovered from the BM of deceased donor VBs and living donor aspirated iliac crest, which showed no difference [24-26].

The fourth message that our analysis conveys is that experience matters and may vary substantially across different processing centers. As with most technical activities, the processing of BM cells from cadaveric bone follows a learning curve. It is well established that the products of industrial manufacturing improve with learning, a phenomenon first documented over 80 years ago [27] and subsequently incorporated into standard textbooks on operations management [17, 28]. In more recent times it has been shown that the learning-curve phenomenon extends to both the outcomes and cost of medical procedures [18-20]. We observed different learning trajectories in the BM processing centers we studied (results provided in the below Technical Appendix B) and, although we analyzed only two centers, our results suggest that the pace of learning and the shape of the learning curve may vary substantially across centers, a factor that should be considered in the design of future training programs, BM processing protocols, and certification practices. Our analysis implies that a volume-outcome relationship exists for the processing of BM and that a high-volume, regional center that has accumulated more processing experience may produce a higher-quality BM product compared to a low-volume center.

Although, the intent of the present study was not to optimize yield or viability, some comparisons can be made with data from previous reports of deceased human donor BM recovery where optimization was the goal. Three previous studies have compared BM from a combined total of 99 deceased donors to that of a combined 58 living donors [24-26]. In these reports, the percentage of CD34+ cells from deceased donor BM (2.1+0.6%; mean+standard deviation) was not statistically different (p=0.32) than BM aspirated from living donors (1.56+0.92%). This compares well with our findings in which the average percentage of CD34+ cells recovered was 2.43+0.64% (mean+standard error). We did observe greater variation in CD34+ percentages, which likely reflects the extreme range of ischemia times and, consequently, the quality of donor tissue on arrival in our study.

The quality of deceased-donor CD34+ HSPCs also has been compared to living-donor HSPCs by assaying CD34+ cell viability and CFU potential [24-26]. Mean viability of CD34+ cells recovered from deceased donors was 95.2±3.6% compared to 93.5±0.35% for living donors. Functional equivalency of deceased-donor and living-donor BM HSPCs was established by comparing the frequency of CFU-GM, which was 105±65 per 105 TNC plated in deceased-donor BM, compared to 81.4±17 per $10^5$ TNC plated in living donor BM. By comparison, our overall averages from deceased-donor BM (Tables 2 and 3) were lower for both of these quality metrics, presumably due, again, to the extreme range of ischemia times and the inclusion of body cooling in our study, which negatively impacted average cell viabilities. We have subsequently used the findings reported here to establish limits of 8 hours WIT and 30 hours CIT, and have eliminated the practice of body cooling. Following this protocol change, vertebrae from 50 donors meeting these criteria have now been recovered and processed (manuscript in preparation). The average CD34+ HSPC viability was 90.5+1.9% and the average CFU-GM was 158.3+13.5/105 TNC plated, which is comparable to the previous studies [24-26].

Overall, our study demonstrates the feasibility of recovering high volumes of BM from deceased donors for banking. Building a BM bank with sufficient HLA diversity requires an ample source and steady supply of deceased-donor medullary bones. Fortunately, the Uniform Anatomical Gift Act of 1968 established a syndicate of 58 geographically distributed OPOs. Each year approximately 10,000 deceased individuals donate their organs and a further 40,000 donate tissues, yielding approximately 30,000 organs and over a million tissues recovered annually (unos.org/data/transplant-trends/accessed 29 Nov. 2019). The high volume of bones potentially recoverable through this network, could provide the necessary inventory to justify the establishment of an integrated system of bone procurement, recovery, and transport, linked to BM processing and banking centers. An integrated system of this type would require the cooperation and coordination of multiple OPOs all following agreed-upon operational protocols. Our study demonstrates the feasibility of building such a system using existing OPO infrastructure. In particular, we have demonstrated that protocols can be developed and enforced, to maintain a favorable ischemic environment from the point of bone procurement and recovery, through cross-country shipping, to arrival at the BM processing center. Because our data were unconstrained for the variables of body-cooling and ischemia times, they likely possess a high level of external validity (generalizability), and the results of our predictive models (FIG. 2) can be used to establish realistic ischemia-time tolerance limits and HSPC quality acceptance criteria.

The creation of a BM banking system would offer several distinct advantages over current living-donor registries. First, personal risk to live donors would be obviated, as opposed to only ameliorated through the present predominant practice of mobilized peripheral blood collection. Second, much larger volumes of HSPCs can be recovered from a deceased donor compared to a living donor, allowing for multiple infusions from the same donor in cases of graft failure. Additionally, recovered cells can be packaged in known quantities, tested for quality, and cryopreserved for later on-demand use. Because the units are cryopreserved, they can be stored indefinitely [29], thereby obviating the problem of attrition that occurs with living-donor registries. Finally, a BM bank can serve as a readily available resource during surges in demand following a mass casualty event, such as a nuclear disaster resulting in widespread bone-marrow failure [1, 2].

For these advantages to be fully realized, a host of logistic and systems issues will have to be addressed. Chief among these is the recognition that the prolonged ischemia times introduced during bone recovery, shipment and processing, need to be effectively managed to assure the quality and yield of BM products. BM banking is now coming into existence and is beginning to display significant potential. From the perspective of a nascent BM processing facility, the results of our statistical models can be used to establish quantitative ischemia tolerance limits and quality acceptance standards for safeguarding the viability and function of HSPCs derived from cadaveric bone. From a broader policy perspective, our models can also provide the foundation for an emerging BM banking system to institute data-driven industry standards.

REFERENCES

1. Knebel, A. R., et al., *Allocation of scarce resources after a nuclear detonation: setting the context*. Disaster Med Public Health Prep, 2011. 5 Suppl 1: p. S20-31.
2. Weinstock, D. M., et al., *Radiologic and nuclear events: contingency planning for hematologists/oncologists*. Blood, 2008. 111(12): p. 5440-5.
3. Kawai, T., et al., *Long-term results in recipients of combined HLA-mismatched kidney and bone marrow transplantation without maintenance immunosuppression*. Am J Transplant, 2014. 14(7): p. 1599-611.
4. Schneeberger, S., et al., *Upper-extremity transplantation using a cell-based protocol to minimize immunosuppression*. Ann Surg, 2013. 257(2): p. 345-51.
5. Spitzer, T. R., et al., *Twenty Year Follow Up of Histocompatibility Leukocyte Antigen—Matched Kidney and Bone Marrow Co-Transplantation for Multiple Myeloma with End Stage Renal Disease: Lessons Learned*. Transplantation, 2019.
6. Hotta, K., et al., *Long-term Nonhuman Primate Renal Allograft Survival Without Ongoing Immunosuppression in Recipients of Delayed Donor Bone Marrow Transplantation*. Transplantation, 2018. 102(4): p. e128-e136.
7. Yamada, Y., et al., *Overcoming memory T-cell responses for induction of delayed tolerance in nonhuman primates*. Am J Transplant, 2012. 12(2): p. 330-40.
8. Eckardt, J. R., et al., *Comparison of engraftment and acute GVHD in patients undergoing cryopreserved or fresh allogeneic BMT*. Bone Marrow Transplant, 1993. 11(2): p. 125-31.
9. Lioznov, M., et al., *Transportation and cryopreservation may impair haematopoietic stem cell function and engraftment of allogeneic PBSCs, but not BM*. Bone Marrow Transplant, 2008. 42(2): p. 121-8.
10. Stockschlader, M., et al., *Use of cryopreserved bone marrow in allogeneic bone marrow transplantation*. Bone Marrow Transplant, 1995. 15(4): p. 569-72.
11. Stockschlader, M., et al., *Use of cryopreserved bone marrow in unrelated allogeneic transplantation*. Bone Marrow Transplant, 1996. 17(2): p. 197-9.
12. AATB, *Guidance Document, in Evaluation of Body Cooling at Standard D5.400*. 2013, American Association of Tissue Banks: McLean, Va. p. 13.
13. Schwartz, D. and J. Lellouch, *Explanatory and pragmatic attitudes in therapeutical trials*. J Chronic Dis, 1967. 20(8): p. 637-48.
14. Donnenberg, A. D., et al., *Clinical implementation of a procedure to prepare bone marrow cells from cadaveric vertebral bodies*. Regen Med, 2011. 6(6): p. 701-6.
15. Gorantla, V. S., et al., *Development and validation of a procedure to isolate viable bone marrow cells from the vertebrae of cadaveric organ donors for composite organ grafting*. Cytotherapy, 2012. 14(1): p. 104-13.
16. Sutherland, D. R., et al., *The ISHAGE guidelines for CD34+ cell determination by flow cytometry. International Society of Hematotherapy and Graft Engineering*. J Hematother, 1996. 5(3): p. 21326.
17. Riahi-Belkaoui, A., *The learning curve: a management accounting tool*. 1986, Westport, Conn.: Quorum Books. xiii, 245 pages.
18. Flood, A. B., W. R. Scott, and W. Ewy, *Does practice make perfect? Part 1: The relations betweeen hospital volume and outcomes for selected diagnostic categories*. Medical Care, 1984. 22(2): p. 98-114.
19. Flood, A. B., W. R. Scott, and W. Ewy, *Doespractice make perfect? Part II: The relation between volumes and other hospital characteristics*. Medical Care, 1984. 22(2): p. 115-125.
20. Woods, J. R., et al., *The learning curve and the cost of heart transplantation*. Health Serv Res, 1992. 27(2): p. 219-38.
21. Harrel Jr, F. E., *Regression modeling strategies with applications to linear models, logistic regression, and survival analysis*. 2nd ed. Springer Series in Statistics. 2001, New York: Springer. 582.
22. Ferrari, S. L. P. and F. Cribari-Neto, *Beta regression for modeling rates and proportions*. J. Applied Statistics, 2004. 31(7): p. 799-815.
23. Picard, R. and D. Cook, *Cross-validation of regression models*. J. Am. Stat. Assoc, 1984. 79(428): p. 1303-1313.

24. Ahrens, N., et al., *Mesenchymal stem cell content of human vertebral bone marrow*. Transplantation, 2004. 78(6): p. 925-9.
25. Rybka, W. B., et al., *Hematopoietic progenitor cell content of vertebral body marrow used for combined solid organ and bone marrow transplantation*. Transplantation, 1995. 59(6): p. 871-4.
26. Soderdahl, G., et al., *Cadaveric bone marrow and spleen cells for transplantation*. Bone Marrow Transplant, 1998. 21(1): p. 79-84.
27. Wright, T., *Factors affecting the cost of airplanes*. J Aeronautical Sciences, 1936. 3(2): p. 122128.
28. Green, J. H., *Operations Management: Productivity and Profit*. 1984: Reston Pub Co. 723.
29. Woods, E. J., et al., *Off the shelf cellular therapeutics: Factors to consider during cryopreservation and storage of human cells for clinical use*. Cytotherapy, 2016. 18(6): p. 697-711.

TECHNICAL APPENDIX A—EXPERIENCE MODELS

To account for learning we created a variable, EXPERIENCE, defined as the number of donors processed prior to the current donor. Donors were numbered serially from i=1 . . . n, in the order they were processed, and EXPERIENCE was coded i−1, to denote the fact that EXPERIENCE was always one less than the current donor being processed. Facility A began processing bone marrow five months before Facility B, and because Facility B had the advantage of participating in (and learning from) cases processed at Facility A, the two facilities had different learning trajectories. To account for this difference, EXPERIENCE was coded separately for each facility. To identify the two facilities in the model, we coded FACILITY A=1 and FACILITY B=0.

Regression Model:

Outcomes (% CD34+, CFU-TOTAL/$10^5$, and GM-TOTAL/$10^5$) were modeled as linear combinations of FACILITY (where the processing occurred), EXPERIENCE (number of cases processed at the facility prior to the current case), and the FACILITY×EXPERIENCE interaction. % CD34+ was modeled using beta regression (see Technical Appendix B). The other two outcomes (CFU-TOTAL and CFU-GM) were modeled using traditional OLS linear regression. Models had the following linear form:

$Y=\beta_0+\beta_1(\text{FACILITY})+\beta_2(\text{EXPERIENCE})+\beta_3(\text{FACILITY}\times\text{EXPERIENCE})$ [A.1]

Where: Y Outcome (% CD34+, CFU/$10^5$, or GM/$10^5$)
$\beta_0$=intercept (constant term)
$\beta_1$=Coefficient associated with FACILITY
$\beta_2$=Coefficient associated with EXPERIENCE
$\beta_3$=Coefficient associated with the FACILITY×EXPERIENCE interaction The interaction term, β3, accounts for the possibility that Facility A may have had a different linear relationship with EXPERIENCE (a different learning trajectory) than Facility B.

Algebra for Deriving Testable Effects

The model for Facility A is:

$Y=\beta_0+\beta_1(\text{FACILITY }A)+\beta_2(\text{EXPERIENCE})+\beta_3(\text{FACILITY }A\times\text{EXPERIENCE})$ $=\beta_0+\beta_1(1)+\beta_2(\text{EXPERIENCE})+\beta_3(1\times\text{EXPERIENCE})$ $=(\beta_0+\beta_1)+(\beta_2+\beta_3)\times(\text{EXPERIENCE})$ [A.2]

The model for Facility B is reduced because Facility B=0 and the terms associated with β1 and β3 drop out of the model. Thus, the model for Facility B is:

$Y=\beta_0+\beta_1(\text{FACILITY }B)+\beta_2(\text{EXPERIENCE})+\beta_3(\text{FACILITY }B\times\text{EXPERIENCE})$ $=\beta_0+\beta_1(0)+\beta_2(\text{EXPERIENCE})+\beta_3(0\times\text{EXPERIENCE})$ $=\beta_0+\beta_1(0)+\beta_2(\text{EXPERIENCE})+\beta_3(0)$ $(\beta_0)+(\beta_2)\times(\text{EXPERIENCE})$ [A.3]

The difference between Equations [A.2] and [A.3] provides insights into the effects that are testable in the model:

FACILITY A:    $Y = (\beta 0 + \beta 1) + (\beta 2 + \beta 3) \times (\text{EXPERIENCE})$  [A. 4]
−FACILITY B:    $Y = (\beta 0)\ \ \ \ \ \ \ + (\beta 2)\ \ \ \ \ \ \ \times (\text{EXPERIENCE})$ FACILITY A − B:    $(\beta 1)\ +(\beta 3)\ \times(\text{EXPERIENCE})$ From [A.4], the following effects are testable as null hypotheses:

H0$_1$: $\beta_0$=0 Tests the significance of FACILITY B's intercept relative to an intercept of zero. (The outcome for Facility B when EXPERIENCE=0).

H0$_2$:$\beta_1$=0 Tests the significance of FACILITY A's intercept relative to FACILITY B's intercept. (The outcome for FACILITY A relative to FACILITY B when EXPERIENCE=0), H0$_3$:$\beta_0$=0 Tests the significance of the learning slope for Facility B (the change in FACILITY B's outcome associated with each additional learning EXPERIENCE).

H0$_4$:$\beta_3$=0 Tests the significance of the learning slope for FACILITY A relative to FACILITY B's slope.

Example Calculation

Following is a worked example for predicting the effect of EXPERIENCE on CFU-GM/$10^5$ given the regression coefficients and observed data values in Table S2:

TABLE S2

Regression coefficients and ischemia time values

| Linear Regression Coefficients | | Predictor Variable | Observed Data |
|---|---|---|---|
| β | 111.91 | Constant | |
| β | −99.34 | FACILITY | A = 1; B = 0 |
| β | −3.57 | EXPERIENCE | 20 Previous Cases |
| β | 4.17 | FACILITY × EXPERIENCE | A = (1 × 20); B = (0 × 20) |

Assume that both FACILITY A and FACILITY B have processed 20 previous donors, what would their respective outcomes be for the 21$^{st}$ donor?

Expected Outcome for FACILITY B:

$CFU\text{-}GM/10^5=(\beta_0)+(\beta_2)\times(\text{EXPERIENCE})$ $=111.91+(-3.57)\times(20)$ $=40.51$ Interpretation for FACILITY B:

Starting with no experience (EXPERIENCE=0), the beginning CFU-GM yield (intercept term) is expected to be 130=111.91 CFU-GM/$10^5$. Each additional donor processed is then expected to subtract 132=−3.57 CFU-GM/$10^5$ from FACILITY B's beginning amount. For the 21st donor processed, FACILITY B's expected yield would be (130)+(132×20)=111.91+(−3.57×20)=40.51 CFU-GM/$10^5$.

Expected Outcome for FACILITY A:

CFU-GM/$10^5$=($\beta_0$+$\beta_1$)×(FACILITY)+($\beta_2$+$\beta_3$)×(FACILITY×EXPERIENCE)

=(111.91−9.34)×(1)+(−3.57+4.17)×(1×20)

=(12.57)+(0.60×20)

=(12.57)+(12.00)

=24.62

Interpretation for FACILITY A:

With no experience, FACILITY A's yield is estimated to be $\beta_0$+$\beta_1$=[111.91+(−99.34)]=12.57 CFU-GM/$10^5$ units more than FACILITY B's. Each additional case that FACILITY A processes adds $\beta_2$+$\beta_3$=(−3.57+4.17)=0.60 CFU-GM/$10^5$ to FACILITY A's starting yield. For the 21st case processed, FACILITY A's yield would be ($\beta_0$+$\beta_1$)+($\beta_2$+$\beta_3$)×(20)=12.57+(0.60×20)=24.57 CFU-GM/$10^5$. Note that Facility A's learning slope is positive, adding $\beta_3$=4.17 CFU-GM/$10^5$ with each additional case processed, while Facility B's learning slope is negative, subtracting $\beta_2$=−3.57 CFU-GM/$10^5$ with each case. This is illustrative of a classic interaction. Expressed in relative terms, each additional learning experience is associated with a net gain of $\beta_2$+$\beta_3$=(−3.57+4.17)=0.60 CFU-GM/$10^5$ for FACILITY A relative to Facility B.

These examples illustrate the pattern that emerged for all three outcomes. FACILITY A, which began processing BM cells before FACILITY B, started at a relatively lower performance level and improved monotonically with each additional case processed. By comparison, FACILITY B, having participated in (and learned from) FACILITY A's initial work, started at a higher level of performance but did not change significantly or declined slightly with increasing experience.

TECHNICAL APPENDIX B—BETA REGRESSION

In the main text, we use CD34+ to denote the count of recovered CD34+ cells and we use % CD34+ to denote the percentage of total CD34+ cells that were viable. That is:

% CD34+=(Viable CD34+)/[(Viable CD34+)+(Nonviable CD34+)]

Because it is a ratio, % CD34+ is confined to the closed unit interval (0≤% CD34+≤1), meaning that it can assume values of 0% or 100% or any value in between, but it cannot be less than 0% or greater than 100%. Given this restriction, ordinary least squares (OLS) linear regression produced unrealistic fitted values that exceeded the interval boundaries-some of the predicted values were less than 0% and some exceeded 100%. To correct for this, we considered beta regression [1] instead of OLS linear regression for models of % CD34+. Maximum likelihood beta regression is used to model beta-distributed random variables, which makes it particularly useful in situations such as ours where the response variable is a rate or proportion measured on a continuous scale and bounded by minimum and maximum values. We continued to use OLS linear regression to model the other two outcome variables, CFU-TOTAL and CFU-GM.

Here we use pCD34=% CD34+ to denote the percent of recovered CD34+ cells that were viable. To ensure that the outcome was evaluable as a beta-distributed variable, we transformed pCD34 as follows:

pCD34*=[1+100(pCD34)]/102

This transformation restricts pCD34* to the open interval, (0<pCD34*<1), thereby satisfying the distributional assumption that the outcome variable can approach, but cannot equal 0% or 100%. The restricted proportion, pCD34* was then modeled by beta regression. For ease of interpretation, predicted values from beta regressions were back transformed to obtain:

Pred(pCD34)=[(102(Pred(pCD34*))−1)/100]=Pred(pCD34)=Pred(% CD34+).

Beta Regression Equation:

The beta regression equation utilizes the logit link function of the outcome to η, a linear predictor. Our basic beta regression equation for predicting pCD34* was:

η=ln[pCD34*/(1 −pCD34*)]=$\beta_0$+$\beta_1$(WIT)+$\beta_2$(BCT)+$\beta_3$($BCT^2$)+$\beta_4$(CIT)+$\beta_5$($CIT^2$)

Where:
$\beta_0$=Constant (intercept)
$\beta_1$=Coefficient associated with warm ischemia time (WIT)
$\beta_2$=Coefficient associated with body cooling time (BCT)
$\beta_3$=Coefficient associated with body cooling time squared ($BCT^2$)
$\beta_4$=Coefficient associated with cod ischemia time (CIT)
$\beta_5$=Coefficient asociated with cold ischemia time squared (CIT Example Calculation:

To illustrate the calculations, we use the coefficients and ischemia times shown in Table S3.

TABLE S3

Regression coefficients and ischemia time values

| Beta Regression Coefficients | | Predictor Variable | Observed Data (Ischemia Times) | |
|---|---|---|---|---|
| β | 3.500 | Constant | | |
| β | −0.01996 | Warm Ischemia Time (WIT) | 1.92 | WIT hours |
| β | −0.181 | Body-Cooling Time (BCT) | 0.00 | BCT hours |
| β | 0.007 | Body Cooling Time squared $(BCT)^2$ | 0.00 | BCT hours$^2$ |
| β | −0.111 | Cold Ischemia Time (CIT) | 14.92 | CIT hours |
| β | 0.002 | Cold Ischemia Time squared $(CIT)^2$ | 222.606 | hours$^2$ |

Using Equation [B.1] we solve for q as shown in Equation [B.2], below

η=ln[pCD34*/(1 −pCD34*)]=$\beta_0$+$\beta_1$(WIT)+$\beta_2$(BCT)+$\beta_3$($BCT^2$)+$\beta_4$(CIT)+$\beta_5$($CIT^2$)

=500+(0.01996)(1.92)+(−0.181)(0)+(0.007)(0)+(−0.111)(14.92)+(0.002)(222.606)

2.2507688           [B.2]

Because they are related to the outcome variable through a nonlinear function, the coefficients of the linear predictor, q, lack a simple intuitive meaning. However, by applying the inverse link function to q we obtain a result that is easier to interpret.

The Inverse Link Function:

The inverse link function, exp(i)/[1+erp (i)], converts the linear predictor, q, to the expected
value of the outcome variable pCD34*:

$$E[pCD34^*] = \frac{\exp(\eta)}{[1 + \exp(\eta)]} =$$

$$\frac{\exp[\beta_0 + \beta_1(WIT) + \beta_2(BCT) + \beta_3(BCT^2) + \beta_4(CIT) + \beta_5(CIT^2)]}{1 + \exp[\beta_0 + \beta_1(WIT) + \beta_2(BCT) + \beta_3(BCT^2) + \beta_4(CIT) + \beta_5(CIT^2)]}$$

Applying the inverse link function to the predicted value, η=2.2507688, calculated from Equation [B.2], we obtain the expected value, E[pCD34*]:

E[pCD34*]=exp(2.2507688)/1+exp(2.2507688)
=0.905≈90.5%

This result is interpretable as the expected value of pCD34* for the specified values of the predictors given in Table S3.

To interpret the result of [B.3] in terms of pCD34 (the percentage of viable CD34+ cells), we use the back transformation:

$$pCD34^* = \frac{1 + 100\, pCD34}{102} \rightarrow pCD34 = \qquad [B.4]$$

$$\frac{102\, pCD34^* - 1}{100} = \frac{[(102)(0.905)] - 1}{100} = 0.9131$$

Equation [B.4] says that for the values specified in Table S3, the expected percentage of viable CD34+ cells is pCD34=% CD34+=91.31%.

Determining the Expected Impact on pCD34* of a One-Unit Change in a Given Predictor Variable:

The beta regression coefficient for any given predictor can be used to estimate the impact on pCD34* of a one-unit change in that predictor, controlling for all other predictors in the equation. This is accomplished via exponentiation of the particular regression coefficient under consideration. For example, to calculate the impact of a one-hour increase in warm ischemia time (WIT) on the ratio of the percent of viable CD34+ cells to the percent nonviable CD34+ cells, the ratio under consideration is:

$$\frac{pCD34^*}{(1 - pCD34^*)} = \frac{\exp(\eta)}{1 + \exp(\eta)} \bigg/ \left[1 - \frac{\exp(\eta)}{1 + \exp(\eta)}\right] = \exp(\eta)$$

From Table S3, the regression coefficient associated with WIT is β1=−0.01996. Therefore, the impact of a one-hour increase in WIT on the ratio of percent viable to percent nonviable CD34+ cells is:

$$\frac{\exp[\beta_0 + \beta_1(WIT + 1) + \beta_2(WCT) + \beta_3(CIT) + \beta_4(CIT^2)]}{\exp[\beta_0 + \beta_1(WIT) + \beta_2(WCT) + \beta_3(CIT) + \beta_4(CIT^2)]} = \qquad [B.5]$$

$$\exp(-0.01996) = 0.98$$

Equation [B.5] says that if WIT were increased by one hour, while the other variables in the equation (BCT and CIT) remained unchanged, the ratio of the percent viable to percent nonviable CD34+ cells would decrease by a factor of 2%, to 98% of its previous value. We previously calculated pCD34*=0.905, in Equation [B.3]. Thus, a one-hour increase in WIT would reduce pCD34* to 0.98× 0.903=0.885, a 2% reduction. Equivalently, this would reduce the predicted pCD34 from 0.913 to 0.893, approximately a 2% reduction. The multiplicative factor, 0.98, is a constant applicable to any unit change along the continuous range of warm ischemia times. Factors for the other predictors can be obtained in the same way to estimate the impact of a unit change in BCT and CIT on pCD34*.

TECHNICAL APPENDIX C—UNADJUSTED (BASE) ISCHEMIA-TIME REGRESSION MODELS

In initial (base) regression models we used only WIT, BCT, and CIT as predictors (no adjustments for other covariates). Results of these models for % CD34+, CFU-TOTAL, and CFU-GM are shown in Tables S4-S6. Model results are shown in the left panels of the tables; averaged results of 200 cross-validated models (each estimated with one observation omitted from the full dataset) are shown in the right panels.

Beta regression models for % CD34+ are shown in FIG. 27. The relationship of WIT to % CD34+ was not statistically significant, however, BCT (linear component, p=0.001 and second-order polynomial component, p=0.01), and CIT (linear component, p=0.001 and second-order polynomial component, p=0.004) were both curvilinearly related to % CD34+. In both cases the CD34+ yield declines in response to increasing BCT and CIT, but then slightly increases at the upper extremes of BCT and CIT. The odds ratios in FIG. 27 are continuous-variable ratios of viable CD34+ cells to total CD34+ cells and depict the impact of a one-unit change in a given predictor. These quantities are obtained via exponentiation of the regression coefficient associated with the particular predictor under consideration. For example, the coefficient associated with WIT is β1=−0.01996. (FIG. 27) Exponentiation produces the following result:

eβ=e−0.01996=0.9802 or 98.02%, which is the value of the continuous odds ratio for Warm Ischemia shown in FIG. 27. This result says that with BCT and CIT held constant, each one unit (one hour) increase in WIT reduces the ratio of viable to nonviable CD34+ to 98.02% of its previous value. The multiplicative factor, 0.9802, is a constant applicable to a one-unit change anywhere along the continuous range of WIT. Factors for the other predictors are provided in FIG. 27 and can be used to estimate the effect of a one-unit change in BCT or CIT holding other variables in the equation constant. The beta-regression prediction equation is statistically significant (p=0.0009).

The right half of FIG. 27 shows the averaged results of bootstrapped cross-validations, which provide estimates of the original model's validity in predicting future observations [2]. If the original model was mis-specified the parameters of the re-estimated bootstrapped models would differ from the parameters of the original model. However, as revealed in FIG. 27, model parameters (regression coefficients, standard errors, and 95% confidence intervals) associated with the original model (left panel) are nearly the same as the corresponding parameters generated through bootstrap re-sampling (right panel), providing evidence of the original model's predictive validity when applied to future data drawn from the same population. [Technical details regarding beta-regression and example calculations are provided in Technical Appendix B, above].

FIG. 28 shows linear regression results for CFU-TOTAL. The coefficients in linear regressions are direct estimates of the impact of a unit change in the associated predictor. BCT is the only statistically significant predictor in FIG. 28. WIT and CIT are not significant. The relationship of BCT to CFU-TOTAL is curvilinear, indicating that each one-hour increase in BCT decreases CFU-TOTAL by $-95.03639/10^5$ cells (p<0.0001) while simultaneously increasing CFU-TOTAL$^2$ by $3.45603/10^5$ (p=0.0008). Together, the linear and second-order polynomial components combine to produce a decreasing trend in CFU-TOTAL that decays at a decelerating rate. The model parameters (left panel of FIG. 28) are similar to the averaged parameters of the bootstrapped models (right panel), providing evidence of the original model's predictive validity. The model is statistically significant (p=0.00002) and explains 35% of the variance in CFU-TOTAL.

FIG. 29 shows linear regression results for CFU-GM. In this model the influences of WIT and BCT are statistically significant, while the influence of CIT is not significant. With CIT and BCT held constant, each hour of WIT reduces CFU-GM by $-8.11295/10^5$ (p=0.01). With WIT and CIT constant, each hour of BCT reduces CFU-GM by $-5.52927/10^5$ (p<0.000009).

The right side of FIG. 29 shows that the estimated parameters of the bootstrapped models are similar to those of the original model, again providing evidence of the original model's predictive validity when applied to future data. The model is statistically significant (p=0.00002) and accounts for 32% of the total variation in CFU-GM counts.

REFERENCES

1. Ferrari S L P, Cribari-Neto F. Beta regression for modeling rates and proportions. *Journal of Applied Statistics*. 2004, 31(7):799-815
2. Harrel Jr, F., *Regression modeling strategies with applications to linear models, logistic regression, and survival analysis*. 2nd ed. Springer Series in Statistics. 2001, New York: Springer. 582

What is claimed is:

1. A method for manipulating environmental conditions of a cadaver such that stem cells obtained from bone explanted from the cadaver comprise stem cells, among which at least 70% of recovered stem cells are viable, the method comprising steps of:
    (1) identifying a human who is nearing death;
    (2) recording the time of death of the human, at this time the human becomes a cadaver;
    (3) placing the cadaver or an explanted bone from the cadaver into a cooling environment;
    (4) recording the time when step (3) occurs;
        wherein the period of time from step (2) to step (3) is referred to as the warm ischemia time (WIT) and step (3) is performed from no less than one-half to no more than about eight hours after step (2); and
    (5) processing the cadaver bone for extraction of stem cells; and
    (6) recording the time when step (5) begins;
        wherein the period of time from step (3) to step (5) is referred to as the cold ischemia time (CIT) and step (5) is performed from no less than about seven hours to no more than about thirty-nine and one-half hours after step (3),
    wherein the total ischemia time, comprising the sum of WIT and CIT, is less than about forty hours such that:
        when the WIT is more than one-half hour, the CIT is no more than thirty-nine and one-half hours; and
        when the WIT is about eight hours, the CIT is no more than thirty-two hours;
    wherein when the sum of WIT and CIT is greater than forty hours and/or WIT is greater than eight hours and/or CIT is greater than about thirty-nine and one-half hours, fewer recovered stem cells will be viable when compared to when the sum of WIT and CIT is forty hours or less and/or WIT is from no less than about one-half to no more than about eight hours and/or CIT is from no less than about seven hours to no more than about thirty-nine and one-half hours.

2. The method of claim 1, wherein the method provides at least about 80% viable CD34+ cells.

3. The method of claim 1, wherein the method provides at least about 10 to about 350 CFU-Total, wherein, CFU-Total is the total number of colony forming units (CFUs) per $10^5$ nucleated cells detected.

4. The method of claim 1, wherein the method provides at least about 10 to about 100 CFU-GM, wherein CFU-GM is the number of CFU granulocyte macrophages detected per $10^5$ nucleated cells.

5. The method of claim 1, wherein the Body Cooling Time (BCT) is less than about four hours, wherein the BCT begins when the cadaver is placed in a cooling environment and ends when cadaver bone is placed in a cooling environment or condition;
    wherein BCT only occurs when a cadaver is placed into a cooling environment and an explanted bone is extracted from the cooled cadaver.

6. The method of claim 5, wherein the BCT is less than about 1 hour.

7. The method of claim 6, wherein the BCT is about zero hours.

8. The method of claim 1, wherein the total ischemia time comprising the sum of WIT, CIT, and Body Cooling Time (BCT) is less than about forty hours, wherein the BCT begins when the cadaver is placed in a cooling environment and ends when cadaver bone is placed in a cooling environment or condition;
    wherein BCT only occurs when a cadaver is placed into a cooling environment and an explanted bone is extracted from the cooled cadaver.

9. The method of claim 8, wherein the BCT is less than one hour.

10. The method of claim 9, wherein the BCT is about zero hours.

11. The method of claim 1, wherein the recovered stem cells comprise hematopoietic stem cells.

12. The method of claim 11, wherein the recovered stem cells comprise CD34+ cells.

13. The method of claim 12, wherein at least 80% of the recovered CD34+ cells are viable.

14. The method of claim 13, wherein at least 85% of the recovered CD34+ cells are viable.

15. The method of claim 11, wherein the recovered stem cells comprise mesenchymal stem cells (MSCs).

16. The method of claim 1, wherein the recovered stem cells comprise mesenchymal stem cells (MSCs).

17. The method of claim 1, wherein the cadaver bone is derived from a vertebral body, an ileum, or a combination thereof.

18. The method of claim 1, wherein the cadaver bone is derived from a plurality of cadaver bones from the same donor.

19. The method of claim 1, wherein the cadaver bone is obtained from a human donor.

20. The method of claim 1, wherein:
when the WIT is more than one hour, the CIT is no more than thirty-nine hours,
when the WIT is more than one and one-half hours, the CIT is no more than thirty-eight and one-half hours,
when the WIT is more than two hours, the CIT is no more than thirty-eight hours,
when the WIT is more than two and one-half hours, the CIT is no more than thirty-seven and one-half hours,
when the WIT is more than three hours, the CIT is no more than thirty-seven hours,
when the WIT is more than three and one-half hours, the CIT is no more than thirty-six and one-half hours,
when the WIT is more than four hours, the CIT is no more than thirty-six hours,
when the WIT is more than four and one-half hours, the CIT is no more than thirty-five and one-half hours,
when the WIT is more than five hours, the CIT is no more than thirty-five hours,
when the WIT is more than five and one-half hours, the CIT is no more than thirty-four and one-half hours,
when the WIT is more than six hours, the CIT is no more than thirty-four hours,
when the WIT is more than six and one-half hours, the CIT is no more than thirty-three and one-half hours,
when the WIT is more than seven hours, the CIT is no more than thirty-three hours, and
when the WIT is more than seven and one-half hours, the CIT is no more than thirty-two and one-half hours.

21. The method of claim 1, wherein:
when the sum of WIT and CIT is forty hours or greater, fewer recovered stem cells will be viable when compared to when the sum of WIT and CIT is about thirty hours or less;
when the sum of WIT and CIT is thirty hours or greater, fewer recovered stem cells will be viable when compared to when the sum of WIT and CIT is about twenty hours or less; and
when the sum of WIT and CIT is twenty hours or greater, fewer recovered stem cells will be viable when compared to when the sum of WIT and CIT is about ten hours or less.

* * * * *